(12) United States Patent
Ganjam

(10) Patent No.: US 11,359,234 B2
(45) Date of Patent: Jun. 14, 2022

(54) BARCODING SEQUENCES FOR IDENTIFICATION OF GENE EXPRESSION

(71) Applicant: Microsoft Technology Licensing, LLC, Redmond, WA (US)

(72) Inventor: Kris K. Ganjam, Seattle, WA (US)

(73) Assignee: MICROSOFT TECHNOLOGY LICENSING, LLC, Redmond, WA (US)

(*) Notice: Subject to any disclaimer, the term of this patent is extended or adjusted under 35 U.S.C. 154(b) by 454 days.

(21) Appl. No.: 15/626,021

(22) Filed: Jun. 16, 2017

(65) Prior Publication Data

US 2018/0002748 A1 Jan. 4, 2018

Related U.S. Application Data

(60) Provisional application No. 62/357,828, filed on Jul. 1, 2016, provisional application No. 62/399,190, filed on Sep. 23, 2016, provisional application No. 62/487,671, filed on Apr. 20, 2017.

(51) Int. Cl.
| | |
|---|---|
| *C12Q 1/6869* | (2018.01) |
| *G16B 25/00* | (2019.01) |
| *G06N 3/12* | (2006.01) |
| *C12Q 1/6897* | (2018.01) |
| *C12N 15/90* | (2006.01) |
| *G06F 21/62* | (2013.01) |
| *G06F 21/60* | (2013.01) |
| *G16B 25/10* | (2019.01) |
| *C12Q 1/6806* | (2018.01) |
| *G06F 9/448* | (2018.01) |

(52) U.S. Cl.
CPC ......... *C12Q 1/6869* (2013.01); *C12N 15/902* (2013.01); *C12Q 1/6806* (2013.01); *C12Q 1/6897* (2013.01); *G06F 9/4498* (2018.02); *G06F 21/602* (2013.01); *G06F 21/6218* (2013.01); *G06N 3/123* (2013.01); *G16B 25/00* (2019.02); *G16B 25/10* (2019.02); *C12Q 2563/179* (2013.01)

(58) Field of Classification Search
None
See application file for complete search history.

(56) References Cited

U.S. PATENT DOCUMENTS

| | | | |
|---|---|---|---|
| 7,056,724 | B2 | 6/2006 | Wong et al. |
| 7,659,590 | B2 | 2/2010 | Boland et al. |
| 9,384,320 | B2 | 7/2016 | Church |
| 9,957,526 | B2 * | 5/2018 | Holmes ................ C12N 15/907 |
| 2002/0061528 | A1 | 5/2002 | Gardner et al. |
| 2005/0053968 | A1 | 3/2005 | Bharadwaj et al. |
| 2010/0047805 | A1 | 2/2010 | Wang |
| 2012/0003630 | A1 | 1/2012 | Collins et al. |
| 2012/0296857 | A1 | 11/2012 | Burns et al. |
| 2014/0273231 | A1 | 9/2014 | Zhang et al. |
| 2014/0315310 | A1 | 10/2014 | Lu et al. |
| 2015/0133315 | A1 | 5/2015 | Jacobson et al. |
| 2015/0225801 | A1 | 8/2015 | Cai et al. |
| 2015/0261664 | A1 | 9/2015 | Goldman et al. |
| 2015/0269313 | A1 | 9/2015 | Church |
| 2015/0368639 | A1 | 12/2015 | Gill et al. |
| 2015/0376650 | A1 | 12/2015 | Auerbach et al. |
| 2016/0024524 | A1 | 1/2016 | Joung et al. |
| 2016/0040155 | A1 | 2/2016 | Maizels et al. |
| 2016/0053274 | A1 | 2/2016 | D'halluin |
| 2016/0168592 | A1 | 6/2016 | Church et al. |
| 2016/0312313 | A1 | 10/2016 | Kotula et al. |
| 2016/0317677 | A1 | 11/2016 | Bhatia et al. |
| 2016/0333363 | A1 | 11/2016 | Srivastava |
| 2017/0096680 | A1 | 4/2017 | Lu et al. |
| 2017/0211099 | A1 | 7/2017 | Auerbach et al. |
| 2017/0369870 | A1 | 12/2017 | Gill et al. |
| 2018/0002725 | A1 | 1/2018 | Ganjam |
| 2018/0004537 | A1 | 1/2018 | Ganjam |

(Continued)

FOREIGN PATENT DOCUMENTS

| | | |
|---|---|---|
| AU | 2017257225 A1 | 11/2018 |
| CA | 2963080 A1 | 4/2016 |

(Continued)

OTHER PUBLICATIONS

Findlay et al., "Saturation editing of genomic regions by multiplex homology-directed repair" 513 Nature 120-123 and Methods (2014).*
Paquet et al., "Efficient introduction of specific homozygous and heterozygous mutations using CRISPR/Cas9" 533 Nature 125-129 and Methods (Apr. 27, 2016).*
"International Application Serial No. PCT/US2017/039063, Invitation to Pay Additional Fees and Partial Search Report dated Oct. 5, 2017", 14 pgs.
"International Application Serial No. PCT/US2017/039976, International Search Report dated Oct. 18, 2017", 5 pgs.
"International Application Serial No. PCT/US2017/039976, Written Opinion dated Oct. 18, 2017", 6 pgs.
"International Application Serial No. PCT/US2017/040046, International Search Report dated Oct. 10, 2017", 5 pgs.

(Continued)

*Primary Examiner* — Nancy J Leith
(74) *Attorney, Agent, or Firm* — Newport IP, LLC; Benjamin A. Keim

(57) ABSTRACT

Gene expression can be identified by analyzing a DNA sequence. The DNA sequence can include a barcode sequence that corresponds to a particular gene. The barcode sequence can be produced during the expression of a gene by first adding a Homologous Directed Repair (HDR) template including the barcode sequence into the DNA sequence of the gene and then splicing the barcode sequence out of an RNA precursor during the expression of the gene. As the barcode sequence is made available from the RNA precursor, it can be added to the DNA strand using HDR. The resulting DNA strand can be sequenced and the sequence data can be analyzed to identify the barcode sequence within the DNA sequence, which provides an indicator of the expression of the gene in DNA rather than RNA.

6 Claims, 13 Drawing Sheets

Specification includes a Sequence Listing.

(56) References Cited

U.S. PATENT DOCUMENTS

| | | | |
|---|---|---|---|
| 2018/0004890 | A1 | 1/2018 | Ganjam |
| 2019/0119701 | A1 | 4/2019 | Liang et al. |

FOREIGN PATENT DOCUMENTS

| | | | |
|---|---|---|---|
| CN | 1628174 | A | 6/2005 |
| CN | 101889088 | A | 11/2010 |
| CN | 105473773 | A | 4/2016 |
| CN | 105492611 | A | 4/2016 |
| CN | 105602993 | A | 5/2016 |
| CN | 105683379 | A | 6/2016 |
| CN | 106795521 | A | 5/2017 |
| CN | 109415724 | A | 3/2019 |
| CN | 109415725 | A | 3/2019 |
| CN | 109415726 | A | 3/2019 |
| CN | 109477130 | A | 3/2019 |
| CN | 111344403 | A | 6/2020 |
| EP | 2313515 | A1 | 4/2011 |
| EP | 3597748 | B1 | 4/2021 |
| KR | 20150027756 | A | 3/2015 |
| KR | 20160001455 | U | 1/2016 |
| WO | 2013169867 | A1 | 11/2013 |
| WO | 2015116969 | A2 | 8/2015 |
| WO | 2015176990 | A1 | 11/2015 |
| WO | 2015199614 | A1 | 12/2015 |
| WO | 2016025719 | A1 | 2/2016 |
| WO | 2016028682 | A1 | 2/2016 |
| WO | 2016040594 | A1 | 3/2016 |
| WO | 2016059610 | A1 | 4/2016 |
| WO | 2016183438 | A1 | 11/2016 |
| WO | WO-2016/205728 | A1 | 12/2016 |
| WO | 2018005117 | A1 | 1/2018 |
| WO | 2018005289 | A2 | 1/2018 |
| WO | 2018005289 | A3 | 1/2018 |
| WO | 2018005782 | A1 | 1/2018 |
| WO | 2018005824 | A1 | 1/2018 |

OTHER PUBLICATIONS

"International Application Serial No. PCT/US2017/040046, Written Opinion dated Oct. 10, 2017", 8 pgs.

Ben-Aroya, Shay, et al., "Making temperature-sensitive mutants", NIH Public Access, Author Manuscript, Published in final edited form as: *Methods Enzymo.*, 470, (2010), 181-204, (2010), 23 pgs.

Chu, Van Trung, et al., "Increasing the efficiency of homology-directed repair for CRISPR-Cas9-induced precise gene editing in mammalian cells", *Nature Biotechnology*, (2015), 543-548.

Danino, Tal, et al., "A synchronized quorum of genetic clocks", *Nature*, vol. 463, (2010), 326-330.

Dow, Lucas E., et al., "Inducible in vivo genome editing with CRISPR-Cas9", *Nature Biotechnology*, 33(4), (Apr. 2015), 390-394.

Dow, Lukas E., et al., "Inducible in vivo genome editing with CRISPR-Cas9", Supplemental Material, *Nature Biotechnology*, 33(4), (Apr. 2015), 10 pgs.

Espeso, Eduardo A., et al., "pH regulation is a major determinant in expression of a fungal penicillin biosynthetic gene", *The EMBO Journal*, 12(10), (1993), 3947-3958.

Fan, H. Christina, et al., "Expression profiling. Combinatorial labeling of single cells for gene expression cytometry", *Science*, 347(6222), 1258367, (2015), 9 pgs.

Heid, Christian A., et al., "Real Time Quantitative PCR", *Genome Research*, 6(10), (1996), 986-994.

Hussain, Faiza, et al., "Engineered temperature compensation in a synthetic genetic clock", *Proc. Natl. Acad. Sci.*, 111(3), (2014), 972-977.

Kulkarni, A. S., et al., "Stimulation of Homology-Directed Repair at I-SceI-Induced DNA Breaks during the Permissive Life Cycle of Human Cytomegalovirus", *Journal of Virology*, 85(12), (Jun. 2011), 6049-6054.

Lafountaine, Justin S., et al., "Delivery and therapeutic applications of gene editing technologies ZFNs, TALENs, and CRISPR/Cas9", *International Journal of Pharmaceutics*, 494(1), (Aug. 2015), 180-194.

Macosko, Evan Z., et al., "Highly Parallel Genome-wide Expression Profiling of Individual Cells Using Nanoliter Droplets", *Cell*, 161(5), (2015), 1202-1214.

McKenna, Aaron, et al., "Whole-organism lineage tracing by combinatorial and cumulative genome editing", *Science*, 353(6298), aaf7907, (2016), 11 pgs.

Neupert, Juliiane, et al., "Design of simple synthetic RNA thermometers for temperature-controlled gene expression in *Escherichia coli*", *Nucleic Acids Research*, 36(19), e124, (2008), 9 pgs.

Nitsche, Andreas, et al., "Different Real-Time PCR Formats Compared for the Quantitative Detection of Human Cytomegalovirus DNA", *Clinical Chemistry*, 45(11), (1999), 1932-1937.

Pierce, Andrew J., et al., "XRCC3 promotes homology-directed repair of DNA damage in mammalian cells", *Genes & Development*, 13, (1999), 2633-2638.

Ryback, Brendan M, et al., "Design and analysis of a tunable synchronized oscillator", *Journal of Biological Engineering*, 7(26), (2013), 1-10.

"Cas9", Retrieved From: https://en.wikipedia.org/wiki/Cas9, Retrieved Date: Sep. 14, 2016, 6 Pages.

"CRISPR interference", Retrieved From: https://en.wikipedia.org/wiki/CRISPR_interference, Retrieved Date Sep. 14, 2016, 4 Pages.

"CRISPR/Cas Tools", Retrieved From: https://en.wikipedia.org/wiki/CRISPR/Cas_Tools, Retrieved Date: Sep. 14, 2016, 3 Pages.

"Editas medicine", Retrieved From: http://www.editasmedicine.com/, Retrieved Date: Sep. 14, 2016, 1 Page.

"Gene drive", Retrieved From: https://en.wikipedia.org/wiki/Gene_drive, Retrieved Date: Sep. 14, 2016, 4 Pages.

McKenna, et al., "Whole organism lineage tracing by combinatorial and cumulative genome editing", Retrieved from http://dx.doi.org/10.1101/052712, May 11, 2016, 34 Pages.

Addgene, "CRISPR/Cas9 Guide", In CRISPR/Cas9 Guide, Retrieved From: https://www.addgene.org/crispr/guide/, Retrieved on: Sep. 14, 2016, 17 Pages.

Bate, Geoggrey, "Bits and genes: A comparison of the natural storage of information in DNA and digital magnetic recording", In Proceedings of the IEEE Transactions on Magnetics, vol. MAG-14, Issue 5, Sep. 1, 1978, pp. 964-965.

Bonnet, et al., "Rewritable Digital Data Storage in Live Cells via Engineered Control of Recombination Directionality", In Proceedings of the National Academy of Sciences, vol. 109, Issue 23, Jun. 5, 2012, 6 Pages.

Byrne, Michael, "Scientists Built a Biological Computer inside a Cell", Retrieved From: https://motherboard.vice.com/en_us/article/jpgdgd/engineers-develop-key-building-block-for-sophisticated-bio-computers, Jul. 22, 2016, 4 Pages.

Caliando, et al., "Targeted DNA Degradation Using a CRISPR Device Stably Carried in the Host Genome", In Proceedings of the Nature Communications, vol. 6, Article No. 6989 (2015), May 19, 2015, 10 Pages.

Chu, et al., "Increasing the Efficiency of Homology-directed Repair for CRISPR-Cas9-induced Precise Gene Editing in Mammalian Cells", In Journal of Nature Biotechnology, vol. 33, Issue 5, Mar. 23, 2015, 9 Pages.

Davis, et al., "Homology-directed repair of DNA icks via pathways distinct from canonical double-strand break repair", In Proceedings of the National Academy of Sciences, Feb. 20, 2014, 9 Pages.

Defrangesco, Ralph M., "Biological Cells as Storage Devices", In Proceedings of the Ninth International Conference on Information Technology—New Generations, Apr. 16, 2012, 3 Pages.

Fan, et al., "Combinatorial labeling of single cells for gene expression cytometry", In Proceedings of the Science, vol. 347, No. 6222, Feb. 5, 2015, 8 Pages.

Farboud, et al., "Dramatic Enhancement of Genome Editing by CRISPR!Cas9 Through Improved Guide RNA Design", In Proceedings of the Genetics, Apr. 1, 2015, 18 Pages.

(56) References Cited

OTHER PUBLICATIONS

Farzadfard, et al., "Genomically Encoded Analog Memory with Precise in Vivo DNA Writing in Living Cell Populations", In Proceedings of the Science, vol. 346, Issue 6211, Nov. 14, 2014, 10 Pages.
Fusi, et al., "In Silico Predictive Modeling of CRISPR/Cas9 Guide Efficiency", Retrieved From: https://www.biorxiv.org/content/biorxiv/early/2015/06/26/021568.full.pdf, Jun. 26, 2015, 31 Pages.
Gao, et al., "DNA-guided genome editing using the Natronobacterium gregoryi Argonaute", In Journal of Nature Biotechnology, vol. 34, May 2, 2016, pp. 768-773.
Gearing, Mary, "Cpf1: A New Tool for CRISPR Genome Editing", Retrieved From: https://blog.addgene.org/cpf1-a-new-tool-for-crispr-genome-editing, Oct. 14, 2015, 5 Pages.
Glaser, et al., "Statistical Analysis of Molecular Signal Recording", In Proceedings of the PLoS computational biology, vol. 9, Issue 7, Jul. 1, 2013, 14 Pages.
He, et al., "Knock-in of large reporter genes in human cells via CRISPR/Cas9-induced homology-dependent and independent DNA repair", In Proceedings of the Nucleic Acids Research, vol. 44, Issue 9, Feb. 4, 2016, 14 Pages.
Heler, et al., "Mutations in Cas9 Enhance the Rate of Acquisition of Viral Spacer Sequences during the CRISPR-Cas Immune Response", In Proceedings of the Molecular cell, vol. 65, Issue 1, Jan. 5, 2017, 17 Pages.
Hossein, et al., "GBlocks Gene Fragments-Related Decoded Articles", Retrieved From: https://web.archive.org/web/20150912022743/http://www.idtdna.com/pages/products/genes/gblocks-gene-fragments/decoded-articles/decoded/2013/12/13/crispr-and-cas9-for-flexible-genome-editing, Sep. 18, 2015, 10 Pages.
Hsiao, et al., "A population based temporal logic gate for timing and recording chemical events", In Proceedings of the Molecular systems biology, vol. 12, Issue 5, May 17, 2016, 14 Pages.
Irving, Michael, "New record for storing digital data in DNA", Retrieved From: https://newatlas.com/dna-data-storage-record/44273/, Jul. 11, 2016, 17 Pages.
Ji, Weiyue, et al., "Specific Gene Repression by CRISPRi System Transferred through Bacterial Conjugation", Retrieved From: https://www.ncbi.nlm.nih.gov/pmc/articles/PMC4277763/, Dec. 19, 2014, 3 Pages.
Jusiak, et al., "Engineering Synthetic Gene Circuits in Living Cells with CRISPR Technology", In Publication of Trends in biotechnology, vol. 34, Issue 7, Jan. 22, 2016, 13 Pages.
Kalhor, et al., "Rapidly evolving homing CRISPR barcodes", In Proceedings of Nature Methods, vol. 14, Issue 2, Feb. 1, 2017, 19 Pages.
Kawane, et al., "DNA Degradation and Its Defects", In Cold Spring Harbor perspectives in biology, vol. 6, Issue 6, Jan. 9, 2018, 15 Pages.
Keskin, et al., "Transcript-RNA-templated DNA recombination and repair", In Nature, vol. 515, Issue 7527, Nov. 20, 2014, 34 Pages.
Khoso, Mikal, "Storing Digital Data in DNA", Retrieved From: https://www.northeastern.edu/levelblog/2016/05/18/storing-data-dna/, May 18, 2016, 3 Pages.
Kim, et al., "Synthetic in vitro transcriptional oscillators", In Molecular Systems Biology, vol. 7, Issue 1, Article No. 465, Feb. 1, 2011, 15 Pages.
Kowalczykowski, "Homologous Recombination Proteins and their Potential Applications in Gene Targeting Technology", Retrieved From: https://web.archive.org/web/20060914085115/http://microbiology.ucdavis.edu/sklab/PDF_files/Kowalczykowski%20and%20Zarling%20(1995)%20Gene%20Targeting%20chapter.pdf, 1995, 44 Pages.
Kowalczykowski, "In vitro reconstitution of homologous recombinaton reactions", In Experientia, vol. 50, Issue 3, Mar. 15, 1994, 13 Pages.
Krejci, et al., "Homologous recombination and its regulation", In Nucleic Acids Research, vol. 40, Issue 13, Mar. 30, 2012, 24 Pages.
Kumar, et al., "Secret data writing using DNA sequences", In Proceedings of the International Conference on Emerging Trends in Networks and Computer Communications (ETNCC), Apr. 22, 2011, pp. 402-405.
Kupferschmidt, Kai "Genome editor CRISPR helps trace growth of embryos and maybe cancer next", Retrieved From: http://www.sciencemag.org/news/2016/05/genome-editor-crispr-helps-trace-growth-embryos-and-maybe-cancer-next, May 26, 2016, 13 Pages.
Lakin, et al., "Modelling, Simulating and Verifying Turing-Power, Strand Displacement Systems", In Proceedings of the 17th International Conference on DNA computing and molecular programming, Sep. 19, 2011, pp. 130-144.
Lebar, et al., "A bistable geneticswitch based on designable DNA-binding domains", In Proceedings of the Nature Communication, Sep. 29, 2014, 13 Pages.
Lee, "Genome editing in vivo with the delivery of Cas9 ribonucleoprotein and donor DNA complexed to gold nanoparticles", In Proceedings of the 5th International Conference and Exhibition on Cell and Gene Therapy, May 19, 2016, 4 Pages.
Lee, et al., "RNA-Guided Genome Editing in *Drosophila* with the Purified Cas9 Protein", Retrieved From: https://www.ncbi.nlm.nih.gov/pubmed/24875628, May 28, 2014, 5 Pages.
Lenz, et al., "Temporal and spatial oscillations in bacteria", In Nature Reviews Microbiology, vol. 9, Issue 8, Aug. 15, 2011, 13 Pages.
Lewin, "Chapters Recombination of DNA", Retrieved From: http://www.bx.psu.edu/~ross/workmg/RecombineDNACh8.pdf, Retrieved Date: Jun. 27, 2017, 30 Pages.
Li, et al., "Harnessing homologous recombination in vitro to generate recombinant DNA via SLIC", In Nat Methods, vol. 4, Issue 3, Mar. 1, 2007, 7 Pages.
Limbachiya, et al., "On optimal family of codes for archival DNA storage", In Proceedings of the Seventh International Workshop on Signal Design and its Applications in Communications (IWSDA), Sep. 14, 2015, pp. 123-127.
Mali, et al., "Supplementary information for RNA-Guided Human Genome Engineering via Cas9", In Journal of Science, vol. 339, Issue 6121, Jan. 3, 2013, 35 Pages.
Marblestone, et al., "Physical Principles for Scalable Neural Recording", In Frontiers in Computational Neuroscience, vol. 7, Article 137, Oct. 21, 2013, 49 Pages.
Marblestone, et al., "Rosetta Brains: A Strategy for Molecularly-Annotated Connectomics", Retrieved From: https://arxiv.org/abs/1404.5103, Apr. 1, 2014, 19 Pages.
Maruyama, et al., "Inhibition of non-homologous end joining increases the efficiency of CRISPR/Cas9-mediated precise [TM: inserted] genome editing", In Nat Biotechnol, Issue 33, Issue 5, May 1, 2015, 17 Pages.
Morrical, "DNA-Pairing and Annealing Processes in Homologous Recombination and Homology-Directed Repair", In Cold Spring Harbor perspectives in biology, vol. 7, Issue 2, Feb. 2, 2015, 20 Pages.
Nelles, et al., "Programmable RNA Tracking in Live Cells with CRISPR/Cas9", Retrieved From: https://www.ncbi.nlm.nih.gov/pmc/articles/PMC4826288/pdf/nihms764827.pdf, Apr. 7, 2016, 19 Pages.
Nielsen, et al., "Multi-Input CRISPR/Cas Genetic Circuits That Interface Host Regulatory Networks", In Journal of Molecular Systems Biology, vol. 10, Issue 11, Nov. 28, 2014, 11 Pages.
McDade, Joel.,"The PAM Requirement and Expanding CRISPR Beyond SpCas9", Retrieved From: https://blog.addgene.org/the-pam-requirement-and-expanding-crispr-beyond-spcas9, Nov. 12, 2015, 6 Pages.
O"Neill, et al., "Circadian rhythms persist without transcription in a eukaryote", In Nature, vol. 469, Issue 7331, Jan. 27, 2011, 11 Pages.
O'Driscoll, et al., "Synthetic DNA :The Next Generation of Big Data Storage", In Journal of Science, vol. 4, Issue 3, May 1, 2013, 4 Pages.
Mali, et al., "RNA-Guided Human Genome Engineering via Cas9", In Journal of Science, vol. 339, Issue 6121, Aug. 15, 2013, 8 Pages.
"International Search Report and Written Opinion Issued in PCT Application No. PCT/US2017/037731", dated Sep. 25, 2017, 12 Pages.

(56) References Cited

OTHER PUBLICATIONS

"International Search Report and Written Opinion Issued in PCT Application No. PCT/US2017/039063", dated Jan. 10, 2018, 21 Pages.

Perli, et al., "Continuous Genetic Recording with Self-Targeting CRISPR-Cas in Human Cells", In Science, vol. 353, Issue 6304, Aug. 18, 2016, 4 Pages.

Petersen, et al., "A strand graph semantics for DNA-based computation", In Theoretical computer science, vol. 632, Jun. 13, 2016, 50 Pages.

Prindle, et al., "A sensing array of radically coupled genetic 'biopixels", In Nature, vol. 481, Issue 7379, Dec. 18, 2011, 6 Pages.

Prindle, et al., "Rapid and tunable post-translational coupling of genetic circuits", Retrieved From: https://www.nature.com/articles/nature13238, Apr. 9, 2014, 16 Pages.

Proudfoot, J. Nick "Ending the message: poly(A) signals then and now", In Proceedings of the Genes & development, vol. 25, Issue 17, 2011, 14 Pages.

Purcell, et al., "A comparative analysis of synthetic genetic oscillators", In Journal of The Royal Society Interface vol. 7, Issue 52, Nov. 6, 2010, 22 Pages.

Qi, et al., "Repurposing CRISPR as an RNA-guided platform for sequence-specific control of gene expression", In Journal of Cell, vol. 152, Issue 5, Feb. 28, 2013, 11 Pages.

Ran, et al., "Double Nicking by RNA-Guided CRISPR Cas9 for Enhanced Genome Editing Specificity", Retrieved From: https://www.ncbi.nlm.nih.gov/pmc/articles/PMC3856256/pdf/nihms516731.pdf, Sep. 12, 2013, 19 Pages.

Raymond, et al., "Deinococcus radiodurans RNA ligase exemplifies a novel ligase Glade with a distinctive N-terminal module that is important for 5'-PO4 nick sealing and ligase adenylylation but dispensable for phosphodiester formation an adenylylated nick", Retrieved From: https://www.ncbi.nlm.nih.gov/pmc/articles/PMC1807946/pdf/gkl1090.pdf, Jan. 4, 2007, 11 Pages.

Reilly, Patrick, "Why is mRNA fed into the CRISPR Cas9 system and not DNA?", Retrieved From: https://www.quora.com/Why-is-mRNA-fed-into-the-CRISPR-Cas9-system-and-not-DNA, Jun. 5, 2015, 3 Pages.

Roquet, et al., "Synthetic recombinase-based state machines in living cells", Retrieved From: http://science.sciencemag.org/content/353/6297/aad8559.long, Jul. 22, 2016, 1 Page.

Sekiguchi, et al., "Ligation of RNA-Containing Duplexes by Vaccinia DNA Ligase", Retrieved From: https://www.ncbi.nlm.nih.gov/pubmed/9220997, Jul. 22, 1997, 1 Page.

Shimanovsky, et al., "Hiding Data in DNA", In Proceedings of the Revised Papers from the 5th International Workshop on Information Hiding, Oct. 7, 2002, pp. 373-386.

Shipman, et al., "Molecular Recordings by Directed CRISPR Spacer Acquisition", In Proceedings of the Science, vol. 353, Issue 6298, Jul. 29, 2016, 22 Pages.

Silas, et al., "Direct CRISPR spacer acquisition from RNA by a natural reverse transcriptase-Cas1 fusion protein", In Proceedings of the Science, vol. 351, Issue 6276, Feb. 26, 2016, 31 Pages.

Sriskanda, et al., "Specificity and fidelity of strand joining by Chlorella virus DNA ligase", In Proceedings of the Nucleic Acids Research, vol. 26, Issue 15, Aug. 1, 1998, 6 Pages.

Stricker, et al., "A fast, robust and tunable synthetic gene oscillator", Retrieved From: https://www.nature.com/articles/nature07389, Nov. 27, 2008, 38 Pages.

Tamsir, et al., "Robust Multicellular Computing Using Genetically Encoded nor Gates and Chemical 'Wires", In Proceedings of the Nature,vol. 469 Issue 7329, Jan. 13, 2011, 9 Pages.

Tigges, et al., "A tunable synthetic mammalian oscillator", Retrieved From: https://www.nature.com/articles/nature07616, Jan. 15, 2009, 4 Pages.

Trafton, Anne, "Engineers program human cells to store complex histories in their DNA", Retrieved From: https://phys.org/news/2016-08-human-cells-complex-histories-dna.html, Aug. 18, 2016, 4 Pages.

Trafton, Anne, Human DNA cells genetically engineered to store memories and "complex histories", Retrieved From: https://futuristech.info/posts/human-dna-cells-genetically-engineered-to-store-memories-and-complex-histories/, Aug. 23, 2016, 3 Pages.

Tsai, et al., "Robust, Tunable Biological Oscillatons from Interlinked Positive and Negative Feedback Loops", In Proceedings of the Science, vol. 321, Issue 5885, Jul. 4, 2008, 19 Pages.

Unciuleac, et al., "Characterization of a novel eukaryal nick-sealing RNA ligase from Naegleria Gruberi", In Proceedings of the RNA, May 1, 2015, 9 Pages.

Vishwakarma, et al., "High Density Data Storage in DNA Using an Efficient Message Encoding Scheme", In International Journal of Information Technology Convergence and Services, vol. 2, Issue 2, Apr. 30, 2012, pp. 41-46.

Waters, Virginia L., "Conjugation between bacterial and mammalian cells", Retrieved From: https://www.nature.com/news/2001/011122/full/news011122-4.html, Nov. 19, 2001, 4 Pages.

Weinberg, et al., "Large-scale design of robust genetic circuits with multiple inputs and outputs for mammalian cells", In Proceedings of the Nature Biotechnology, vol. 35, Issue 5, Mar. 27, 2017, 20 Pages.

Weintraub, Karen, "CRISPR gene-editing system unleashed on RNA", Retrieved From: https://www.nature.com/news/crispr-gene-editing-system-unleashed-on-rna-1.20030, Jun. 3, 2016, 4 Pages.

Williams, Sarah, "DNA tape recorder stores a cell's memories", Retrieved From: http://www.sciencemag.org/news/2014/11/dna-tape-recorder-stores-cells-memories, Nov. 13, 2014, 7 Pages.

Woods, Mae, et al., "A Statistical Approach Reveals Designs for the Most Robust Stochastic Gene Oscillators", In Publication of ACS Synthetic Biology, vol. 5, Issue 6, Jun. 17, 2016, 39 Pages.

Wu, et al., "Target specificity of the CRISPR-Cas9 system", Retrieved From: https://www.ncbi.nlm.nih.gov/pmc/articles/PMC4338555/pdf/nihms657677.pdf, Jun. 1, 2014, 19 Pages.

Yang, et al., "Enrichment of G2/M cell cycle phase in human pluripotent stem cells enhances HDR-mediated gene repair with customizable endonucleases", Retrieved From: https://www.ncbi.nlm.nih.gov/pmc/articles/PMC4757933/pdf/srep21264.pdf, Feb. 18, 2016, 15 Pages.

Yang, et al., "Permanent Genetic Memory with >1-byte Capacity", Nature Methods, vol. 11, Issue 12, Dec. 1, 2014, 18 Pages.

Yazdi, et al., "A Rewritable, Random-Access DNA-Based Storage System", In Journal of Scientific Reports, vol. 5, Sep. 18, 2015, 10 Pages.

Yin, et al., "Thereapeutic genome editing by combined viral and non-viral delivery of CRISPR system components in vivo", In Nat Biotechnol, vol. 34, Issue 3, Mar. 1, 2016, 15 Pages.

Yordanov, et al., "Functional Analysis of Large-scale DNA Strand Displacement Circuits", In Journal of International Conference on DNA Computing and Molecular Programming, vol. 8141, Sep. 1, 2013, pp. 189-203.

Yosef, et al., "Proteins and DNA elements essential for the CRISPR adaptation process in *Escherichia coli*", In Proceedings of the Nucleic Acids Research, vol. 40, Issue 12, Mar. 8, 2012, 8 Pages.

Zuris, et al., "Cationic lipid-mediated delivery of proteins enables efficient protein-based genome editing in vitro and in vivo", In Proceedings of the Nature Biotechnology, vol. 33, Oct. 30, 2014, 49 Pages.

"Non Final Office Action Issued in U.S. Appl. No. 15/623,925", dated Aug. 28, 2018, 13 Pages.

"Non Final Office Action Issued in U.S. Appl. No. 15/626,020", dated Oct. 31, 2018, 17 Pages.

Quetier, Francis, "The CRISPR-Cas9 technology: Closer to the ultimate toolkit for targeted genome editing", In Proceedings of the Plant Science, vol. 242, Sep. 8, 2015, pp. 65-76.

Sorek, et al., "CRISPR-Mediated Adaptive Immune Systems in Bacteria and Archaea", In Proceedings of the Annual Review of Biochemistry, vol. 82, Mar. 11, 2013, pp. 237-266.

Sun, et al., "Recent advances in targeted genome engineering in mammalian systems", In Proceedings of the Biotechnology journal, vol. 7, Issue 9, Jul. 10, 2012, pp. 1074-1087.

Wang, et al., "Genetic screens in human cells using the CRISPR/Cas9 system", Retrieved from: https://www.ncbi.nlm nih.gov/pmc/articles/PMC3972032/, Jan. 3, 2014, pp. 80-84.

(56) References Cited

OTHER PUBLICATIONS

"Final Office Action Issued in U.S. Appl. No. 15/623,925", dated Jan. 22, 2019, 6 Pages.
"Non Final Office Action Issued in U.S. Appl. No. 15/625,998", dated Jul. 18, 2019, 27 Pages.
Andrianantoandro, et al., "Synthetic biology: new engineering rules for an emerging discipline", In Journal of Molecular Systems Biology, EMBO and Nature Publishing Group, May 1, 2006, pp. 1-14.
Schmidt, et al., "Applications of CRISPR-Cas for synthetic biology and genetic recording", In Journal of Current Opinion in System Biology, vol. 5, Oct. 1, 2017, pp. 9-15.
Sheth, et al., "DNA-based memory devices for recording cellular events", In Journal of Nature Reviews Genetics, Sep. 20, 2018, 20 Pages.
Wikipedia, "Homology directed repair", Retrieved From: https://en.wikipedia.org/wiki/Homology_directed_repair, Jul. 15, 2019, 4 Pages.
"Final Office Action Issued in U.S. Appl. No. 15/626,020", dated May 31, 2019, 17 Pages.
Wingler, et al., "Reiterative Recombination for the in vivo assembly of libraries of multigene pathways", In Proceedings of the National Academy of Sciences, Sep. 13, 2011, 6 Pages.
"Non-Final Office Action Issued in U.S. Appl. No. 15/623,925", dated May 8, 2019, 12 Pages.
"Search Report Issued in European Patent Application No. 19185657.4", dated Dec. 9, 2019, 8 Pages.
"Final Office Action Issued in U.S. Appl. No. 15/623,925", dated Nov. 25, 2019, 12 Pages.
"Final Office Action Issued in U.S. Appl. No. 15/625,998", dated Dec. 6, 2019, 15 Pages.
"Non Final Office Action Issued in U.S. Appl. No. 15/625,998", dated Apr. 16, 2020, 7 Pages.
"Non Final Office Action Issued in U.S. Appl. No. 16/450,641", dated Aug. 11, 2021, 14 Pages.
"Office Action Issued in European Patent Application No. 17736842.0", dated May 11, 2020, 3 Pages.
"Office Action Issued in European Patent Application No. 17736842.0", dated Aug. 18, 2020, 5 Pages.
"Office Action Issued in European Patent Application No. 17742885.1", dated Feb. 20, 2020, 7 Pages.
"Extended European Search Report Issued in European Patent Application No. 19185656.6", dated Mar. 13, 2020, 8 Pages.
"First Office Action and Search Report Issued in Chinese Patent Application No. 201780041514.3", dated Aug. 30, 2021, 21 Pages.
"First Office Action and Search Report Issued in Chinese Patent Application No. 201780041175.9", dated Aug. 26, 2021, 11 Pages.
"First Office Action and Search Report Issued in Chinese Patent Application No. 201780041255.4", dated Aug. 16, 2021, 14 Pages.
"First Office Action and Search Report Issued in Chinese Patent Application No. 201780041484.6", dated Sep. 2, 2021, 14 Pages.
Chien, et al., "Multiplexed bioluminescence-mediated tracking of DNA double-strand break repairs in vitro and in vivo". In Journal of Nature Protocols, Jun. 23, 2021, 21 Pages.
Dan, et al., "The Role of BRCA1 in DNA DSB Repair Pathway", In Chinese Journal of Biochemistry and Molecular Biology, vol. 31, Issue 1, Jan. 20, 2015, pp. 28-33.
Ding, et al., "Application of real-time fluorescent quantitative PCR and experimental optimizing", In Journal of Dalian Medical University, vol. 29, Issue 4, Aug. 15, 2007, pp. 404-407.
Lan, et al., "Homologous recombination and gene targeting in Vertebrate Cells", Published in Letters in Biotechnology, vol. 17, Issue 1, Mar. 30, 2006, pp. 88-91.
Lun-Hao, et al., "The principle and applications of binary expression systems in Drosophila melanogaster". Published in Chinese Bulletin of Life Sciences, vol. 27, Issue 5, May 2015, pp. 631-639.
Pierce, et al., "Ku DNA end-binding protein modulates homologous repair ofdouble-strand breaks in mammalian cells", In Journal of Genes and Development, Dec. 15, 2001, pp. 3237-3242.
Run-Chun, et al., "The Development of CRISPR/Cas9 System and Its Application in Crop Genome Editing", In Journal of Scientia Agricultura Sinica, vol. 49, Issue 7, Apr. 15, 2016, 1219-1229.
Si-Min, et al., "Classification and Selection of the Donor DNA in Genome Editing Technologies", In Chinese Journal of Biochemistry and Molecular Biology, vol. 33, Issue 1, Jan. 20, 2017, 10 Pages.
Stark, et al., "Genetic steps of mammalian homologous repair with distinct mutagenic consequences", Published in Molecular and Cell Biology, vol. 24, Issue 21, Nov. 2004, pp. 9305-9316.
Weichang, et al., "High-dimensional Space Digital Coding and Algorithm of DNA Sequence S4-10", In China-Japan Friendship Institute of Clinical Medicine, May 29, 2002, 3 Pages.
Zaboikin, et al., "Non-Homologous End Joining and Homology Directed DNA Repair Frequency of Double-Stranded Breaks Introduced by Genome Editing Reagents", In Journal of Pios One, Jan. 17, 2017, 36 Pages.
Zahir, et al., "Efficient Virus-Mediated Genome Editing in Plants Using the CRISPR/Cas9 System", In Journal of Molecular Plant, Aug. 3, 2015, pp. 1288-1291.
Zi-Zhi, et al., "Pathway choice for DNA double-strand break repair", In Chinese Bulletin of Life Sciences, vol. 26, Issue 11, Nov. 15, 2014, pp. 1172-1175.
"Final Office Action Issued in U.S. Appl. No. 16/450,641", dated Feb. 17, 2022, 6 Pages.
U.S. Appl. No. 16/430,641—Notice of Allowance, dated Jul. 13, 2022, 7 pages.
U.S. Appl. No. 17/724,288, filed Apr. 19, 2022.
U.S. Appl. No. 15/623,925, filed Jun. 15, 2017.
U.S. Appl. No. 15/931,570, filed May 13, 2020.
U.S. Appl. No. 15/625,998, filed Jun. 16, 2017.
"Second Office Action and Search report Issued in Chinese Patent Application No. 201780041514.3", dated Mar. 30, 2022, 14 Pages.

* cited by examiner

BARCODING SEQUENCES FOR IDENTIFICATION OF GENE EXPRESSION

CROSS-REFERENCE TO RELATED APPLICATION

This application claims the benefit of U.S. Provisional Patent Application Ser. No. 62/357,828 filed on Jul. 1, 2016, entitled "Storage Through Iterative DNA Editing," U.S. Provisional Application Ser. No. 62/399,190 filed on Sep. 23, 2016, entitled "Storage Through Iterative DNA Editing," and 62/487,671 filed on Apr. 20, 2017, entitled "Mechanisms for Molecular Event Logging" all of which are expressly incorporated herein by reference in their entirety. This application is related to U.S. patent application entitled "Molecular State Machines" with Ser. No. 15/626,020 and U.S. patent application entitled "Timing of Logged Molecular Events" with Ser. No. 15/625,998 both filed the same day as this application and the entirety of which are both expressly incorporated herein by reference.

BACKGROUND

Cells having the same genes can produce different gene products depending on the environment of the cell. For example, the cells of an organism, such as a human, can have the same genes, but the genes can be expressed in different ways under different conditions. In this way, one cell having the genes of the organism can be expressed as cell having a first function, such as a liver cell, and another cell having the genes of the organism can be expressed as a cell having a second function, such as a muscle cell. Additionally, genes of an organism can be expressed differently in healthy cells versus cells in a diseased state.

Typically, gene expression is monitored through the sequencing of ribonucleic acid (RNA). RNA is produced from deoxyribonucleic acid (DNA) as a template by which a gene product, such as a protein, is made. After the gene product is produced, the RNA used to make the gene product degrades and is no longer detectable after a period of time. RNA sequencing techniques can be used to detect RNA in a cell at a given time and thus, gene expression can be determined from the RNA-sequencing process.

The sequencing of RNA to track gene expression has limitations because, due to the transitory nature of RNA, the expression of genes can only be monitored at a specific point in time. Thus, tracking the expression of a gene over time requires multiple RNA sequencing operations to be performed over a period of time, which can increase the resources and expense of monitoring gene expression via RNA sequencing. Additionally, the RNA sequencing operations destroy the cell being studied and do not provide opportunities for further study of the gene expression of the cell.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

Gene expression can be monitored and identified by analyzing a DNA sequence. The DNA sequence can include a barcode sequence that corresponds to a particular gene. In some cases, the barcode sequence can uniquely identify the gene. When the gene is expressed, the barcode sequence can be produced and added to a DNA strand. In particular, an enzyme can produce a double strand break (DSB) at a cut site in the DNA strand. Homologous Directed Repair (HDR) can be utilized to add the barcode sequence into the DNA strand. The resulting new DNA strand can be sequenced and the sequence data can be analyzed to identify the barcode sequence within the DNA sequence.

The barcode sequence can be produced during the expression of a gene by first adding an HDR template to the DNA sequence of the gene. The HDR template can include the barcode sequence in addition to at least one splicing sequence. The HDR template can be inserted into a coding region of the gene or a non-coding region of the gene, such as the 3' untranslated region (UTR) of the gene. As the gene is expressed, an RNA precursor can be produced that includes the HDR template. A splicing enzyme can remove the non-coding portions included in the RNA precursor, which includes the HDR template. The HDR template is then available to be added to a cut site of a DNA strand through homologous directed repair. DNA sequencing of the DNA strand can then be used to identify the presence of the barcode sequence in the DNA strand as an indicator of the gene being expressed.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
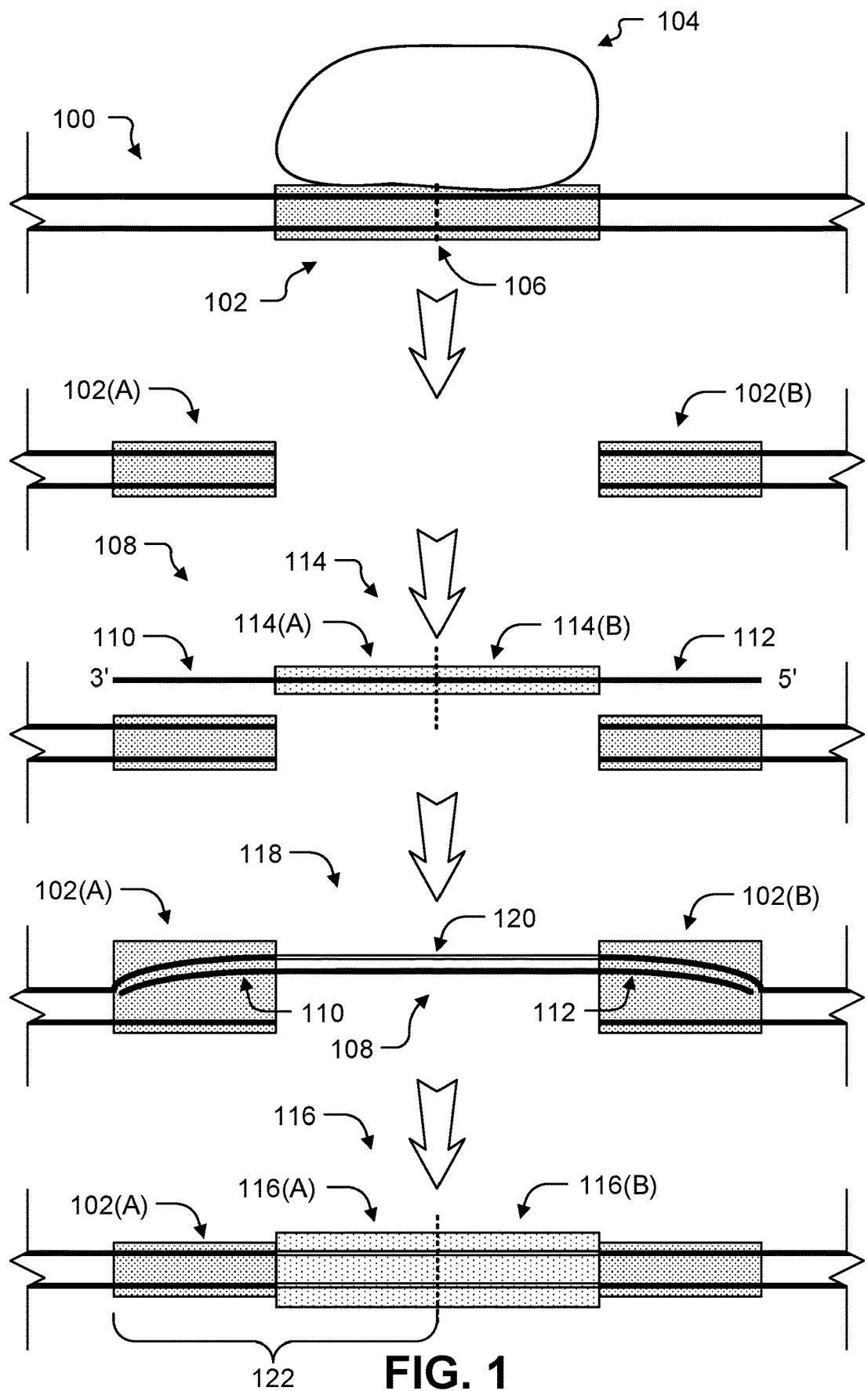
FIG. 1 shows a schematic representation of cutting dsDNA with an enzyme and inserting new DNA by HDR.

This disclosure describes techniques to identify the expression of genes by analyzing DNA sequences rather than RNA sequences. The DNA sequences can include barcode sequences that correspond to the genes being expressed. In some cases, a barcode sequence can be used to uniquely identify a particular gene. In this way, the presence of a barcode sequence in a DNA sequence can indicate the expression of the gene.

Typically, DNA barcoding refers to utilizing relatively short sequences (e.g., less than 800 nucleotides) already found in the genes of an organism in the identification of the organism. Often, DNA barcoding relies on sequences of DNA included in particular locations of a gene to classify organisms within a taxonomy. The barcoding sequences described herein are different from those associated with conventional DNA barcoding because the barcoding sequences described in this application are introduced into the gene through intentional manipulation and are not inherently part of the gene. The barcoding sequences described herein correspond to arbitrary nucleotide sequences added to a particular gene or a particular set of genes and can be utilized to track the expression of the gene(s) in that the availability of the barcoding sequences to be inserted into another polynucleotide is based on the expression of the gene.

In various implementations, a first HDR process can be utilized to insert a first HDR template into a gene for which the expression of that gene is to be tracked. The first HDR template can include a barcoding sequence that corresponds to the gene, as well as at least one splicing sequence. The splicing sequence can correspond to a sequence of nucleotides that is recognized by a splicing enzyme, such as a spliceosome. A spliceosome is a large and complex molecular machine found primarily within the splicing speckles of the cell nucleus of eukaryotic cells. The spliceosome is assembled from snRNAs and protein complexes. The spliceosome removes introns from a transcribed pre-mRNA, a type of primary transcript. This process is generally referred to as splicing. Only eukaryotes have spliceosomes and some organisms have a second spliceosome, the minor spliceosome. In some implementations, the first HDR template can be inserted into a coding region of the gene. The coding region of the gene includes sequences that can directly correlate to a gene product and sequences that do not contribute to the coding of the gene product. The sequences that code for a gene product can be referred to as exons, while the sequences that do not code for a gene product can be referred to as introns. In situations when the first HDR template is inserted into a coding region of the gene, the first HDR template can include two splicing sequences. In other implementations, the first HDR template can be inserted at the end of the 3' untranslated region (UTR). In these instances, the first HDR template can include a single splicing sequence.

As the gene is expressed, the RNA precursor that is produced includes at least a 5' UTR, exons, introns, and a 3' UTR. The first HDR template can be included among the introns of the RNA precursor or in the 3' UTR. As the non-coding sequences are removed from the RNA precursor—to produce messenger RNA (mRNA) that includes the exons, the 5' UTR, and the 3' UTR—the first HDR template is also removed.

In some cases, the non-coding sequences can be removed from the RNA precursor using enzymes, such as spliceosomes. The spliceosomes can recognize specific sequences that are referred to herein as "splicing sequences" and make a cut at certain positions within the specific sequences. Splicing sequences can have a particular arrangement that includes a donor site at the 5' end of the intron, a branch site near the 3' end of the intron, and an acceptor site at the 3' end of the intron. The splice donor site includes a conserved, almost invariant sequence GU at the 5' end of the intron, within a larger, less highly conserved region. The splice acceptor site at the 3' end of the intron terminates the intron with a conserved, almost invariant AG sequence. Upstream (5'-ward) from the AG there is a region high in pyrimidines (C and U), or polypyrimidine tract. Further upstream from the polypyrimidine tract is the branchpoint, which includes an adenine nucleotide involved in lariat formation. An example splicing sequence for an intron in International Union of Pure and Applied Chemistry (IUPAC) nucleic acid notation can include: G-G-[cut]-G-U-R-A-G-U (donor site) . . . intron sequence . . . Y-U-R-A-C (branch sequence 20-50 nucleotides upstream of acceptor site) . . . Y-rich-N-C-A-G-[cut]-G (acceptor site), where Y indicates a pyrimidine, N corresponds to any nucleotide, and R corresponds to a purine.

After the HDR template including the barcode sequence is spliced from the RNA precursor, it is available to be inserted into a double stranded DNA molecule by a second HDR operation. In particular, an enzyme can create a DSB at a target site of the double stranded DNA molecule that is homologous with end portions of the second HDR template. The HDR template can then be inserted into the sequence of the double stranded DNA molecule. The double stranded DNA molecule can then be sequenced and analyzed. The analysis of the sequence data from the double-stranded DNA (dsDNA) molecule can indicate the presence of the barcode sequence, which corresponds to the expression of the gene.

By utilizing the implementations described herein, the expression of a gene can be identified through the sequencing of DNA instead of conventional techniques that operate by sequencing of RNA. In this way, the expression of the gene can be more accurately determined since the analysis is performed with respect to DNA, which is more stable and less transitory than RNA. Thus, rather than obtaining a snapshot of only the RNA that exists at a particular point in time, implementing the techniques described herein can show each of the expressions of the gene that have taken place over a period of time.

Homology Directed Repair

HDR is a mechanism in cells to repair DSBs. The most common form of HDR is homologous recombination. The HDR repair mechanism can be used by the cell when there is a homologous piece of DNA present to repair the DSB. HDR is considered a highly accurate mechanism for DSB repair due to the requirement of sequence homology between the damaged and intact donor strands of DNA. The process is nearly error-free if the DNA template used for repair is identical to the original DNA sequence at the DSB, or it can introduce very specific mutations into the damaged DNA if there are differences between the DNA template use for repair and the original DNA sequence. This disclosure discusses use of a HDR template that adds a new DNA sequence at the point of the DSB as part of the repair process.

HDR includes homologous recombination (HR) and single-strand annealing (SSA) (Lieber. 2010 Annu. Rev. Biochem. 79:181-211). The most common form of HDR is HR which has the longest sequence homology requirements between the donor and acceptor DNA. Other forms of HDR include single-stranded annealing (SSA) and breakage-induced replication, and these require shorter sequence homology relative to HR. HDR at nicks (single-stranded breaks)

can occur via a mechanism distinct from HDR at DSBs (Davis and Maizels. PNAS (0027-8424), 111 (10), p. E924-E932).

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

By "hybridizable" or "complementary" or "substantially complementary" it is meant that a polynucleotide (e.g. DNA or RNA) comprises a sequence of nucleotides that enables it to non-covalently bind, to another polynucleotide in a sequence-specific, antiparallel, manner (i.e., a polynucleotide specifically binds to a complementary polynucleotide) under the appropriate in vitro and/or in vivo conditions of temperature and solution ionic strength. As is known in the art, Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein; and Sambrook, J. and Russell, W., *Molecular Cloning: A Laboratory Manual*, Third Edition, Cold Spring Harbor Laboratory Press, Cold Spring Harbor (2001). The conditions of temperature and ionic strength determine the "stringency" of the hybridization.

It is understood in the art that the sequence of polynucleotide need not be 100% complementary to that of its target polynucleotide to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target site within the target polynucleotide sequence to which they are targeted. For example, an antisense polynucleotide in which 18 of 20 nucleotides of the antisense compound are complementary to a target site, and would therefore specifically hybridize, would represent 90 percent complementarity. In this example, the remaining non-complementary nucleotides may be clustered or interspersed with complementary nucleotides and need not be contiguous to each other or to complementary nucleotides. Percent complementarity between particular stretches of polynucleotide sequences within polynucleotides can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

FIG. 1 shows an illustrative schematic of operations to add a new DNA sequence into dsDNA 100 through HDR. The dsDNA can, in some cases, be included in a gene for which its expression is being monitored. The dsDNA 100 includes a target site 102 that directs an enzyme 104 to create a DSB in the dsDNA 100 within the target site 102 at a specific cut site 106. The DSB may be created with blunt ends or with sticky ends depending on the specific enzyme and technique for making the DSB. The target site 102 is a sequence of DNA recognized by an enzyme that creates DSBs in dsDNA. By "enzyme reactive conditions" it is meant that any necessary conditions are available in an environment (i.e., such factors as temperature, pH, and lack of inhibiting substances) which will permit the enzyme to function. Enzyme reactive conditions can be either in vitro, such as in a test tube, or in vivo, such as within a cell.

The target site 102 may be intentionally introduced into the dsDNA 100 to enable the manipulations described below. Alternatively, a pre-existing portion of the dsDNA 100 may be selected as the target site 102. If a pre-existing portion of the dsDNA 100 is selected as the target site 102, then the sequence of other components of the system will be designed with reference to the sequence of the target site 102. In some implementations, the target site 102 is unique such that there is only one target site 102 in the entire dsDNA strand and/or only one target site 102 throughout all the DNA in the cell. The dsDNA 100 may be genomic DNA inside a living prokaryotic or eukaryotic cell, DNA introduced to a living cell such as a plasmid or vector, or DNA in a cell-free system. The dsDNA 100 may exist as either linear or circular DNA prior to introduction of the DSB.

The enzyme 104 that creates the DSB may be any protein, protein-RNA complex, or protein-DNA complex (including multimeric complexes) that has the property of creating a DSB in dsDNA at the cut site 106. Non-limiting examples of suitable enzymes include restriction enzymes, homing endonucleases, zinc-finger nucleases (ZFNs), transcription activator-like effector nucleases (TALENs), CRISPR/Cas, and NgAgo. These types of enzymes are all examples of site-specific nucleases that are capable of causing a DSB at a cut site 106 within a target site 102. Further details about site-specific nucleases are provided below.

After creating a DSB at the cut site 106, the target site 102 is split into two subsequences 102(A), 102(B) on either side of the DSB. Each of the two subsequences 102(A), 102(B) may, in an implementation, be between 5 and 20 nucleotides (nt) in length. Thus, the target site 102 may, in an implementation, be between 10 and 40 nt in length. In some implementations, the two subsequences 102(A), 102(B) may contain identical DNA sequences. The cut site 106 may be located in the middle of the target site 102 or it may be located elsewhere within the target site 102. The schematic shown in FIG. 1 illustrates a DSB with blunt ends, but as described above DSBs with sticky ends are also covered within the scope of this disclosure.

AN HDR template 108 is brought into proximity of the dsDNA 100 with the DSB. The HDR template 108 is single strand (ss) DNA or ssRNA. The HDR template repairs the DSB and inserts a polynucleotide sequence through the process of homology directed repair. HDR templates used to create specific mutations or insert new elements into a gene require a certain amount of homology surrounding the target site that will be modified. Thus, the HDR template 108 includes a 3'-end sequence 110 complementary to the first subsequence of the target site 102(A) and a 5'-end sequence 112 complementary to a second subsequence of the target site 102(B). Because they are complementary sequences, the length of the 3-end sequence 110 and the 5'-end sequence 112 are the same or about the same as the respective subsequences of the target site 102(A), 102(B). Thus, both 3-end sequence 110 and the 5'-end sequence 112 may be between 5 and 20 nt in length. The middle portion of the HDR template 108 contains a region 114 encoding a second target site 116. This middle region 114 may contain two subsequences 114(A), 114(B) on either side of the point where the second target site 116 will be cut by a second enzyme. The length of the two subsequences 114(A), 114(B) in the middle portion 114 of the HDR template 108 may be different than the lengths of the two subsequences 102(A), 102(B) but may follow the same size range and be between five and 20 nt in length. Thus, the total length of the HDR template 108 may be between about 20 and 80 nt. Because the middle region 114 encodes a second target site 116, the HDR template 108 itself provides the basis for this process to be repeated iteratively. So long as a signal is detected by a cell and the components for creating a DSB and performing HDR are available, this process may continue until the signal ceases. Thus, a length of the inserted DNA may correlate with a duration of the signal.

The HDR template 108 then repairs the DSB through HDR. The efficiency of HDR may be low, and in some conditions, other repair mechanisms can predominate. The efficiency of HDR is determined in part by the concentration of donor DNA present at the time of repair, the length of the homology arms of the donor DNA, the cell cycle, and the activity of the endogenous repair systems. An overabundance of the HDR template 108 may be provided to increase efficiency of HDR. The overabundance of the HDR template 108 may be provided to a cell-free system by adding additional copies of the ssRNA or ssDNA manually or with the use of microfluidics. The HDR template 108 may also be provided, in overabundance if desired, by placing a gene encoding the HDR template 108 under control of a strong promoter and/or by having multiple copies of the gene encoding the HDR template 108 all undergoing transcription. In an implementation, this promoter may be regulated by a signaling pathway that responds to a signal. When the signal is detected, the promoter is turned on and more copies of the HDR template 108 are generated.

The 5'-ended DNA strand is resected at the DSB to create a 3' overhang. This will serve as both a substrate for proteins required for strand invasion and a primer for DNA repair synthesis. The HDR template 108 can then displace one strand of the homologous DNA duplex and pair with the other; this causes formation of hybrid DNA referred to as the displacement loop ("D loop") 118. The recombination intermediates can then be resolved to complete the DNA repair process. As mentioned above, an overabundance of the HDR template 108 may be provided. One of ordinary skill in the art will understand how to perform HDR with dsDNA 100 having a DSB and an HDR template 108. Possible protocols for performing HDR are provided in Jie Liu et al., *In Vitro Assays for DNA Pairing in Recombination-Associated DNA Synthesis*, 745 Methods Mol. Bio. 363 (2011); Gratz, S. et al., *Highly specific and efficient CRISPR/Cas9-catalyzed homology-directed repair in Drosophila*, 196 Genetics 967 (2014); Richardson, C. C. et al., *Enhancing homology-directed genome editing by catalytically active and inactive CRISPR-Cas9 using asymmetric donor DNA*, 34 Nature Biotechnology 399 (2016); and Lin, S. et al., *Enhanced homology-directed human genome engineering by controlled timing of CRISPR/Cas9 delivery*, eLIFE (2014).

After the HDR template 108 invades the dsDNA, the D loop 118 is formed by hybridization of the 3'-end sequence 110 to the first subsequence 102(A) of the target site 102 and hybridization of the 5'-end sequence 112 to the second subsequence 102(B) of the target site 102. DNA polymerase synthesizes new ssDNA 120 complementary to the middle portion 114 of one strand of the dsDNA 100. DNA ligase joins the sugar-phosphate backbone of the newly synthesized ssDNA 120 with the remainder of that strand of the dsDNA 100. This forms one strand of the second target site 116.

Hybridization requires that the two polynucleotides contain complementary sequences, although mismatches between bases are possible. The conditions appropriate for hybridization between two polynucleotides depend on the length of the polynucleotides and the degree of complementation which are variables well known in the art. The greater the degree of complementation between two nucleotide sequences, the greater the value of the melting temperature (Tm) for hybrids of polynucleotides having those sequences. For hybridizations between polynucleotides with short stretches of complementarity (e.g. complementarity over 35 nt or less, 30 nt or less, 25 nt or less, 22 nt or less, 20 nt or less, or 18 nt or less) the position of mismatches becomes important. This is understood by one of ordinary skill in the art and described in Sambrook, J. and Russell, W., *Molecular Cloning: A Laboratory Manual*, Third Edition, Cold Spring Harbor Laboratory Press, Cold Spring Harbor (2001) at sec. 11.7-11.8. Typically, the length for a hybridizable polynucleotide is at least about 10 nt. Illustrative minimum lengths for a hybridizable polynucleotide are: at least about 15 nt; at least about 20 nt; at least about 22 nt; at least about 25 nt; and at least about 30 nt). Furthermore, the skilled artisan will recognize that the temperature, pH, and wash solution salt concentration may be adjusted as necessary according to factors such as length of the region of complementation and the degree of complementation.

Following repair of the first strand of the dsDNA 100, the second strand of the dsDNA 100 is repaired by DNA polymerase and DNA ligase using the sequence of the new ssDNA 120 in the repaired, first strand as a template. This completes the repair of the dsDNA 100 resulting in dsDNA that includes the second target site 116 inserted within the first target site 102.

DNA polymerases are enzymes that synthesize DNA molecules from individual deoxyribonucleotides. During this process, DNA polymerase "reads" an existing DNA strand to create a new, complementary strand. DNA ligase is a specific type of enzyme, a ligase, that facilitates the joining of DNA strands together by catalyzing the formation of a phosphodiester bond. It plays a role in repairing single-strand breaks. The mechanism of DNA ligase is to form two covalent phosphodiester bonds between 3' hydroxyl ends of one nucleotide, ("acceptor") with the 5' phosphate end of another ("donor"). The DNA ligase from bacteriophage T4 is the ligase most-commonly used in laboratory research. It can ligate cohesive or "sticky" ends of DNA, oligonucleotides, as well as RNA and RNA-DNA hybrids, but not single-stranded polynucleotides. It can also ligate blunt-ended DNA.

Note that the HDR template 108 includes two types of regions: end regions and a middle region. The end regions are homologous to one of the strands of the dsDNA 100 on either side of the DSB. Here, the homologous regions are shown by the 3-end sequence 110 and the 5'-end sequence 112. The homology need not be 100% but only to the extent that the 3'-end sequence 110 and the 5'-end sequence 112 hybridize to one strand of the dsDNA 100. The middle region is the middle portion 114 of the HDR template 108 that encodes the sequence of the second target site 116. Independently varying both the end regions and the middle region allows for creation of multiple different HDR templates 108 from a relatively limited set of end regions and middle regions. Thus, the middle region of an inserted HDR template 108 need not have the same target site 102 or cut site 106 as the dsDNA 100 it is being inserted into.

Following HDR, the dsDNA 100 includes the first subsequence 102(A) of the first target site 102 followed by the first subsequence 116(A) of the second target site 116. The DNA sequence 122 represented by this order of the two subsequences 102(A), 116(A) of the two target sites may represent a particular signal combination (e.g., temperature above 30° C. followed by pH under 5). As mentioned above, a length of the subsequence 102(A) is from five to 20 nt and the length of the subsequence 114(A) is also from five to 20 nt. Thus, in an implementation, the total length of the DNA sequence 122 is from 10 to 40 nt.

HDR, however, is not the only way to repair a DSB. Non-Homologous End-Joining (NHEJ) is a pathway that repairs double-strand breaks in DNA and may be favored over HDR in many conditions. NHEJ is referred to as "non-homologous" because the break ends are directly ligated without the need for a homologous template. NHEJ is active throughout the cell cycle and has a higher capacity for repair, as there is no requirement for a repair template (sister chromatid or homologue) or extensive DNA synthesis. NHEJ also finishes repair of most types of breaks in tens of minutes—an order of magnitude faster than HDR. Thus, in many cells there is competition between HDR and NHEJ. If the ratio of HDR to NHEJ is high enough, HDR will continue. However, in the presence of NHEJ some of the DSBs formed by the enzyme 104 will rejoin without an insert.

NHEJ is consequently the principle means by which DSBs are repaired in natural cells. NHEJ-mediated repair is prone to generating indel errors. Indel errors generated in the course of repair by NHEJ are typically small (1-10 nt) but extremely heterogeneous. There is consequently about a two-thirds chance of causing a frameshift mutation. Thus, it may be desirable to minimize NHEJ and increase the probability that a DSB will be repaired by HDR. The likelihood of HDR being used may be improved by inhibiting components of the NHEJ process. Addition of small molecules such as NU7441 and KU-0060648 is one technique for inhibiting NHEJ through inhibition of DNA-dependent protein kinase, catalytic subunit ("DNA-PKcs").

Techniques for enhancing HDR efficiency in this way are described in Maruyama, et al., *Increasing the efficiency of precise genome editing with CRISPR-Cas9 by inhibition of nonhomologous end joining.* 33(5) Nature Biotechnology, 538 (2015) and Robert, et. al., *Pharmacological inhibition of DNA-PK stimulates Cas9-mediated genome editing.* 7 Genome Medicine 93 (2015). In an implementation, HDR efficiency may be improved by suppressing the molecules KU70, KU80, and/or DNA ligase IV, which are involved in the NHEJ pathway. In addition to the suppression, the Cas9 system, E1B55K, and/or E4orf6 may be expressed to further increase HDR efficiency and reduce NHEJ activity. Techniques for enhancing HDR efficiency in this way are described in Chu et al., *Increasing the efficiency of homology-directed repair for CRISPR-Cas9-induced precise gene editing in mammalian cells.* 33(5) Nature Biotechnology, 543 (2015). Further, use of a single-stranded DNA oligo donor (ssODN) has been shown to improve the rate of HDR and knockin efficiency by up to 60% in Richardson et al., *Enhancing homology-directed genome editing by catalytically active and inactive CRISPR-Cas9 using asymmetric donor DNA,* 34(3) Nature Biotechnology 339 (2016).

Figure 2:
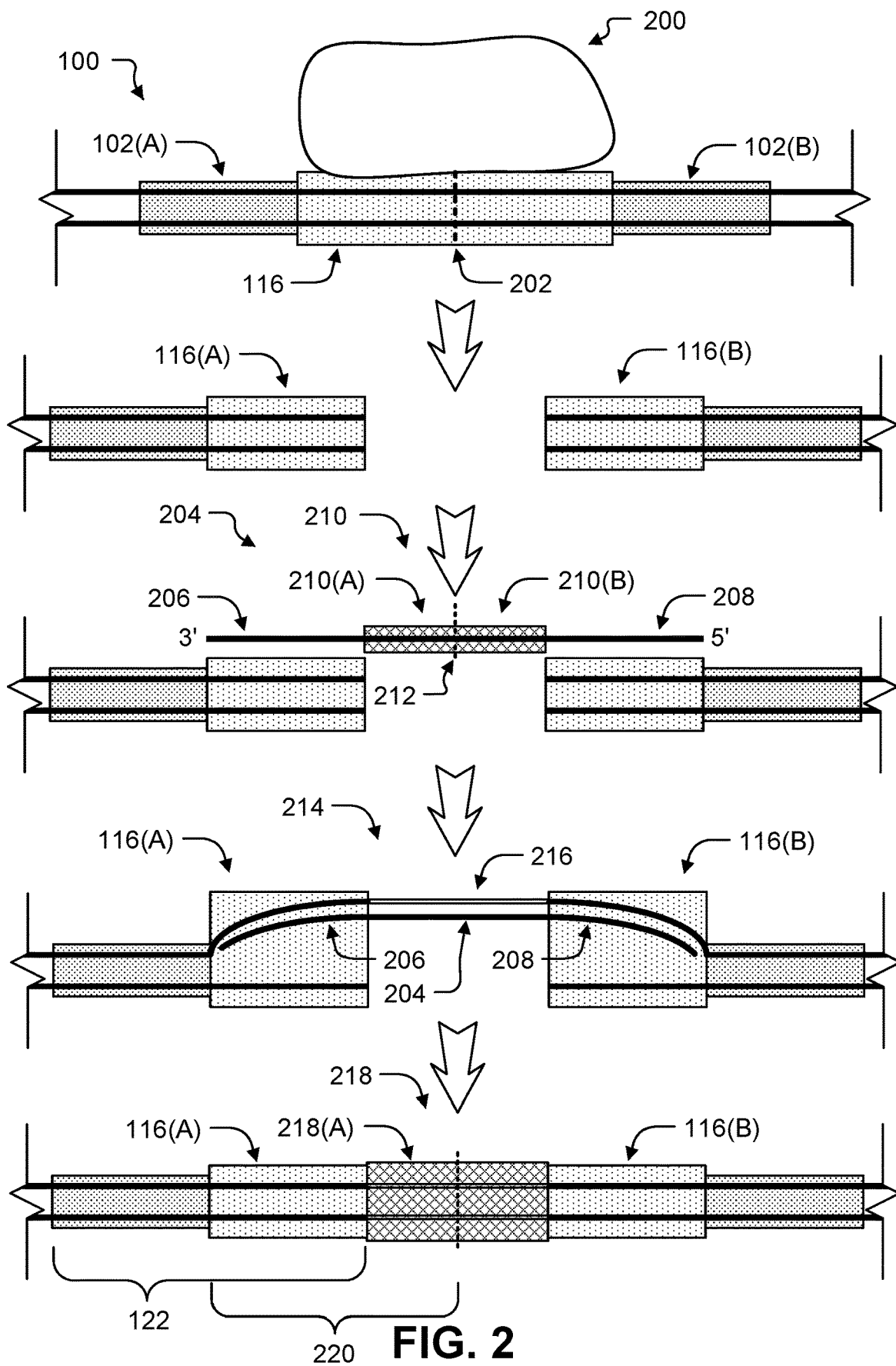
FIG. 2 shows a schematic representation of cutting the dsDNA of FIG. 1 and inserting additional DNA by HDR.

FIG. 2 shows schematic illustrations of further manipulations performed on the dsDNA 100 molecule of FIG. 1. A second enzyme 200 creates a second DSB at a second cut site 202 in the second target site 116. The second target site 116 has a different sequence than the first target site 102, and thus, the second enzyme 200 recognizes a different DNA sequence than the first enzyme 104. Creating a DSB in the second target site 116 at the cut site 202 creates the first subsequence 116(A) of the second target site 116 on one side of the cut site 202 and a second subsequence 116(B) of the second target site 116 on the other side of the cut site 202. In some implementations, the first subsequence 116(A) and the second subsequence 116(B) may have the same sequence. Thus, the first subsequence 116(A) and a second subsequence 116(B) may have the same nucleotide length. Also, if the first subsequence 116(A) and the second subsequence 116(B) are the same sequence, the second target site 116 may be thought of as having a single subsequence repeated once with a cut site 202 in the middle.

A second HDR template 204 contacts the dsDNA 100 to provide a template for HDR of the DSB. The second HDR template 204 includes a 3'-end region 206 that is homologous to one strand of the dsDNA 100 within the first subsequence 116(A) of the second target site 116. The second HDR template 204 also includes a 5'-end region 208 that is homologous to one strand of the dsDNA 100 within the second subsequence 116(B) of the second target site 116. The second HDR template 204 also includes a portion in the middle region 210 that encodes a third target site for a third enzyme. The middle region 210 includes a first subsequence 210(A) on one side of a third cut site 212 and a second subsequence 210(B) on other side of the third cut site 212.

Annealing of the second HDR template 204 to one strand of the dsDNA 100 creates a D loop 214 by hybridization of the 3'-end sequence 206 to the subsequence 116(A) and hybridization of the 5'-end sequence 208 to the subsequence 116(B). DNA polymerase and DNA ligase repair the strand of the dsDNA 100 to which the second HDR template 204 is hybridized by creating new DNA 216. The second strand of the dsDNA 100 is then repaired using the first strand as a template.

The dsDNA 100 now includes the third target site 218 inserted into the middle of the second target site 116 (which is itself inserted in the middle of the first target site 102). The order of the subsequence 116(A) followed by the subsequence 218(A) form a DNA sequence 220 that may create a record of a second combination of detected signals. Thus, the growing string of inserted DNA sequences can provide an ordered log of molecular events experienced by a cell. This process can repeat to record any number of molecular events.

Addition of HDR templates into existing DNA using the mechanisms described above may be regulated by signaling pathways as described in detail below. The encoding scheme described herein allows for insertion of DNA sequences representing an unbounded length. AN HDR template that does not include a cut site may be added once, end the process of HDR, and create a record that a specified signal was detected. The dsDNA in a cell may have multiple different target sites at different locations that include different cut sites and are homologous to different HDR templates. This provides for orthogonal recording of signals without any linkage between the signals. For example, a first target site may be configured to integrate a first HDR template if the cell is exposed to radiation, a second target site may be configured to integrate a second HDR template if the cell is exposed to hydrocarbons, and a third target site may be configured to integrate a third HDR template if the cell is exposed to light. Each cell configured in this way will create independent logs of the signals (e.g., radiation, hydrocarbons, and light) that it was exposed to. A cell may be modified to have any number of orthogonal target sites.

The three target sites may be represented as $X_1X_2$, $Y_1Y_2$, and $Z_1Z_2$. The first portion of the target site (e.g., $X_1$, $Y_1$, or $Z_1$) corresponds to subsequence 102(A) or subsequence 116(A) shown in FIG. 1. The remaining portion of the target site (e.g., $X_2$, $Y_2$, or $Z_2$) corresponds to subsequence 102(B) or subsequence 116(B) shown in FIG. 1. Thus, each X, Y, and Z represents a DNA sequence of about 5 to 20 nt such as, for example only, ACTGAA, GCCTCAT, TGACG, etc. In some implementations $X_1=X_2$, etc., but in other implementations the first portion of a target site may be different in sequence and/or length from the remaining portion of the target site.

The HDR templates all have end regions that are homologous to one of the target sites. Thus, the HDR templates will have sequences of the structure: $X_1aX_2$, $Y_1bY_2$, and $Z_1cZ_2$ where "a," "b," and "c" represent DNA sequences of the middle regions. Recall that the middle region of the HDR templates may itself encode a target site. Thus, for example, a may represent $X_1X_2$, b may represent $Z_1Z_2$, and c may represent a different target site $W_1W_2$. If the middle region does encode a target site, integration of an HDR template into dsDNA may be followed by further integration of the same or a different HDR template. Insertion of an HDR template into dsDNA that has been itself created by integration of an HDR template is referred to in this disclosure as "iterative integration."

Thus, a design using iterative integration of a single HDR template may record the presence of a signal and the length of the signal. For example, the HDR template may be XaXXaX and the initial insertion site may be XX. Iterative integration will result in a sequence that is represented by:

```
XXaXaXaXaX...XaXaXaXaXX
```

This sequence can keep growing continuously while the signal is detected. A potential problem is that the HDR templates may be cut by the same enzyme that creates a DSB at the insertion site because both include the sequence XX which is recognized by the enzyme used for this logging. Physical separation, splicing, self-excising elements, homologous bridges, or methylation may be used to prevent or decrease the amount of HDR templates that are cut before integration into the dsDNA.

In one configuration, the continued detection of multiple signals may be recorded by appropriately designed HDR templates and insertion sites. AN HDR template with a sequence XaYYaX is expressed when a first signal "a" is detected. Similarly, an HDR template YbXXbY is expressed when a second signal "b" is detected. Initially, the cell may include a target site XX or YY. If the cell only includes the target site XX, presence of signal "b" will not be recorded until the HDR template associated with signal "a" is first integrated into the DNA of the cell. As each HDR template provides the target site for the other, alternating exposure to signals "a" and "b" or continued exposure to both signals leads to continued integration of the HDR templates. This alternating, iterative addition will result in a sequence represented by:

```
XaYbXaYbX...XaYbXaYbX
```

This provides sequential recording of signals "a" and "b" independent of the relative concentrations of the HDR templates XaYYaX and YbXXbY. This technique for logging multiple signals at the same location in DNA may be expanded to cover three, four, or even more different signals.

In one configuration, multiple signals may be associated with HDR templates that have the same target sites. For example, a first signal "a" and a second signal "b" may be associated respectively with the HDR templates XaXXaX and XbXXbX. Either HDR template may be integrated into the target site XX. Once integrated, both HDR templates also include the target site XX allowing for iterative addition of either or both. In most conditions, the level of relative incorporation of the two HDR templates will be proportional to the relative concentrations of HDR templates. The amount of each HDR template present in the cell may be designed to be proportional to the strength, frequency, and/or duration of the corresponding signal. For example, if signal "a" is strong and constant the cell may produce a relatively large amount of the XaXXaX template. When signal "b" is present, the amount of the XbXXbX template may increase and then that HDR template is also integrated into the DNA of the cell. So long as all components are present, iterative insertion of these two templates depends on relative strengths of signals "a" and "b" and will result in a sequence represented by:

```
X[a|b]X[a|b]X...X[a|b]X[a|b]X
``` where [a|b] is a or b. The relative amount of "a" vs. "b" in the DNA provides a record of which signal was strongest and changes from a period of "a" dominance to a period of "b" dominance indicates a temporal change in the relative signal strengths. This configuration may be expanded to include three, four, or more different signals and HDR templates. Analysis of the DNA sequence created by this iterative and competitive integration of multiple HDR templates may be performed over defined lengths of nucleotides which represent periods of time. The lengths of nucleotides may be analyzed by considering a series of sliding windows (e.g., a 10,000 nt stretch of the DNA) and determining the relative level of Xa vs. Xb in a given window. This provides information about the relative strength of signals "a" and "b" during a given period of time.

One way of using this configuration is in a cell that has constitutive expression (rather than in response to a signal) of the first HDR template XaXXaX. This template will be expressed and present in the cell at a constant level. It may be thought of as a background signal. The level of the second HDR template XbXXbX will vary depending on the strength of signal "b." Thus, the amount of the XbXXbX template integrated into the DNA indicates the relative strength of signal "b" as compared to the baseline established by expression of XaXXaX.

Another way of using the configuration described above is to use the presence of one of the HDR templates in the DNA of the cell as a temporal indication like a time stamp. For example, the concentration of the first HDR template may respond to the detection of a signal. If the signal is continually present, then the HDR template XaXXaX will be iteratively introduced into the DNA of the cell. As described above, the length of the insertion will depend on the duration that the signal "a" is present. Intentionally exposing the cell to signal "b" at known time points provides references point in the DNA that can be correlated to the known times of exposure to signal "b." When exposed to signal "b," the expression of the second HDR template XbXXbX increases to a level greater than the expression of XaXXaX (e.g., the second HDR template may be regulated by a stronger promoter or present in more copies than the first HDR template). Thus, each point in the DNA that has an insertion of XbXbXb . . . indicates a time when the cell was exposed to "b" For example, if the cell is exposed to signal "b" every 24 hours, each string of DNA between XbXbXb . . . sequences represents the activity of signal "a" during that 24-hour period.

The above configurations may be combined to record multiple signals sequentially regardless of relative strength and also to record the strongest signal based on competing HDR templates. There may be multiple classes of HDR templates with each class having multiple different HDR templates transcribed in response to different signals. For example, there may be two classes of HDR templates XaYYaX and YbXXbY. Because these two HDR templates integrate into the target site created by addition of the other (i.e., the template that integrates into XX adds the target site YY and the template that integrates into YY adds the target site XX) they will alternate. Thus, the DNA will incorporate first an HDR template from the "a" class then an HDR template from the "b" class. Each class of HDR template includes two (but may include any number) HDR templates with partially different sequences that correspond to different signals. Thus, a signal "$a_1$" may cause increased expression of the HDR template $Xa_1YYa_1X$ and a signal "$a_2$" may cause increased expression of the HDR template $Xa_2YYa_2X$. Similarly, a signal "$b_1$" may cause increased expression of the HDR template $Yb_1XXb_1Y$ and a signal "$b_2$" may cause increased expression of the HDR template $Yb_2XXb_2Y$. If the cell begins with DNA that includes the insertion site XX, then first one of the "a" HDR templates will be integrated based on the relative concentrations of the $Xa_1YYa_1X$ and of the $Xa_2YYa_2X$ HDR templates. Doing so creates a YY insertion site and is followed by integrating one of the "b" HDR templates again based on relative concentrations.

In one implementation, each class of the HDR template may record values associated with a particular type of molecular event. For example, the "a" class of HDR templates may indicate temperature experienced by the cell with $Xa_1Ya_1X$ expressed if the temperature is below 32° C. and $Xa_2YYa_2X$ expressed if the temperature is above 42° C. Thus, integration of the "a" class of HDR templates creates a record of relative temperature. The "b" class of HDR templates may be associated with a different type of signal such as salinity. The HDR template $Yb_1XXb_1Y$ may be expressed when the cell is in an environment with salinity below 0.600 M and $Yb_2XXb_2Y$ may be expressed when the cell is in an environment with salinity above 0.700 M. Thus, the record created in the DNA of this cell shows temperature high/low and salinity high/low. Each is recorded in turn so there is a log created over time showing changes in two different signals. Of course, any number of different gradations or levels of variables may be tracked by having distinct HDR templates under the control of appropriate promoter.

In one example implementation, using Cas9 as the nuclease with a PAM sequence of NNNNGATT as the enzyme, three target sites may be:

```
X₁ = TAGCCGTATCGAGCATCGATG|CGCNNNNGATT = X₂

Y₁ = GATCGATGGACTCTGCATCTA|TCGNNNNGATT = Y₂

Z₁ = CGGGACGATCGATCGGGCTAG|ACTNNNNGATT = Z₂
```

Where the PAM sequence is indicated by bold, $X_1$ is (SEQ ID NO: 1), $X_2$ is (SEQ ID NO: 2), $Y_1$ is (SEQ ID NO: 3), $Y_2$ is (SEQ ID NO: 4), $Z_1$ is (SEQ ID NO: 5), and $Z_2$ is (SEQ ID NO: 6). Note that each of $X_1$, $Y_1$, and $Z_1$ are 21 nt long.

Each of the target sites is recognized by a corresponding guide ssDNA that cuts the dsDNA at the location indicated by the "^" below. They should have a trans-activating crRNA (tracrRNA) that is a small trans-encoded RNA for attaching to Cas9 appended to the end. The crRNAs are incorporated into effector complexes, where the crRNA guides the complex to the target site and the Cas proteins create a DSB in the polynucleotide. The respective ssDNA sequences are:

```
gX₁ = TAGCCGTATCGAGCATCGATG^CGC (SEQ ID NO: 1)

gY₁ = GATCGATGGACTCTGCATCTA^TCG (SEQ ID NO: 3)

gZ₁ = CGGGACGATCGATCGGGCTAG^ACT (SEQ ID NO: 5)
```

Then a homology directed repair sequence of $X_1Y_1Y_2X_2$ is: TAGCCGTATCGAGCATCGATG|GATCGATGGACTCTGCATCTA|TCGNNNNGAT-T|CGCNNNNGATT (SEQ ID NO: 7) and a homology directed repair sequence of $Y_1X_1X_2Y_2$ is: GATCGATGGACTCTGCATC-TA|TAGCCGTATCGAGCATCGATG|CGCNNNNGATT|TCGNNNNGATT (SEQ ID NO: 8). Other homology directed repair sequences can be designed according to the same pattern.

An initial cut of the target site $X_1X_2$ will create a DSB that appears as (only one strand of the dsDNA is shown):

```
. . .TAGCCGTATCGAGCATCGATG (SEQ ID NO: 1)
   CGCNNNNGATT. . . (SEQ ID NO: 2)
```

After HDR with $X_1Y_1Y_2X_2$, one strand of the dsDNA will have the following sequence that now includes the target site $Y_1Y_2$ indicated by italics:

```
                                          (SEQ ID NO: 7)
TAGCCGTATCGAGCATCGATG|GATCGATGGACTCTGCATCTA||
TCGANNNNGATT|CGCNNNNGATT.
```

The dsDNA is now able to be cut by a Cas9 that has $Y_1$ creating a DSB at the location represented by "||". HDR may be performed with $Y_1X_1X_2Y_2$, for example, further adding to the dsDNA and completing another iteration of encoding.

This may be continued with various sequences of cuts and HDR templates to record any series of molecular events.

Signaling Pathways

Figure 3:
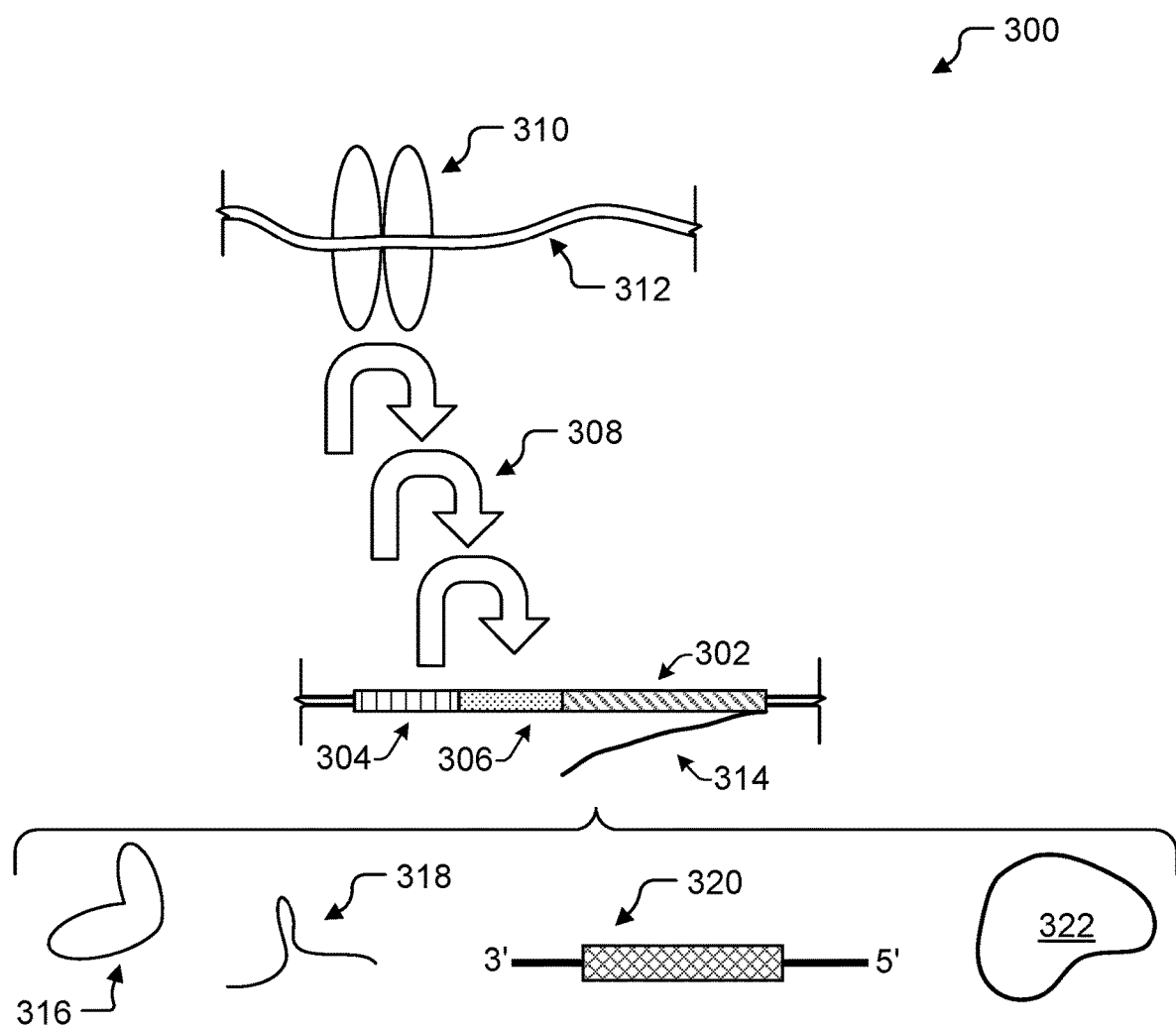
FIG. 3 shows illustrative components for controlling expression of a gene product based on a signaling pathway.

FIG. 3 shows a diagram 300 of an illustrative signaling pathway that regulates expression of a gene. The signaling pathway may be an engineered signaling pathway that is created or modified in some way to be different from a wild-type signaling pathway. The signaling pathway controls the expression of a gene 302 that is under the control of a promoter 304 and may also be under the control of an operator 306. A promoter is a region of DNA that initiates transcription of a particular gene. Promoters are located near the transcription start sites of genes, on the same strand and upstream on the DNA (towards the 5' region of the sense strand). Illustrative promoters are described below. The sequence of the promoter region controls the binding of the RNA polymerase and transcription factors. An operator is a segment of DNA to which a repressor binds to decrease or stop gene expression. A "transcription factor" is a protein that binds near the beginning of the coding sequence (transcription start site) for a gene or functional mRNA. Transcription factors are necessary for recruiting DNA polymerase to transcribe DNA. A transcription factor can function as a repressor, which can bind to the operator to prevent transcription. The gene 302, the promoter 304, and the operator 306 are on a dsDNA molecule that may be genomic DNA of a cell or other DNA such as a plasmid or vector. In some implementations, the promoter 304 may respond to signals such as temperature or pH and thus the promotor 304 itself may be the signaling pathway.

The repressor (and/or "knockdown") may be a protein or mRNA (small hairpin loops (shRNA), interfering mRNA (RNAi or siRNA)) that binds to DNA/RNA and blocks either attachment of the promoter, blocks elongation of the polymerase during transcription, or blocks mRNA from translation. In addition to repressors, the CRISPR/Cas9 system itself may be used for sequence-specific repression of gene expression in prokaryotic and eukaryotic cells. Specifically, the technique of CRISPR interference (CRISPRi) uses catalytically dead Cas9 lacking endonuclease activity to regulate genes in an RNA-guided manner. Catalytically inactive Cas9 may be created by introducing point mutations into the Cas9 protein such as at the two catalytic residues (D10A and H840A) of the gene encoding Cas9. In doing so, dCas9 is unable to cleave dsDNA but retains the ability to target DNA. Targeting specificity for CRISPRi is determined by complementary base pairing of a guide RNA (gRNA) to the genomic loci. The gRNA may be designed to target a specific promoter. The complex catalytically dead Cas9 and the gRNA will block activation of the promoter and turn off expression of any gene regulated by that promoter.

The signaling pathway may include a signaling cascade 308 that carries a signal from a first messenger (i.e., the initial signal) and eventually results in activation, or alternatively suppression, of either the promoter 304 or the operator 306. The initial signal that sets the signaling cascade 308 into action may be an internal or external signal. The signaling pathway may be a trans-membrane signaling pathway that includes an external receptor 310 which detects extracellular signals and communicates the signal across a membrane 312. The membrane 312 may be a cell wall, lipid bilayer, artificial cell wall, or synthetic membrane.

In one implementation, the external receptor 310 may be a G protein-coupled receptor (GPCR). GPCRs constitute a large protein family of receptors, that sense molecules outside the membrane 312 and activate the signaling cascade 308 and, ultimately, cellular responses. The GPCR is activated by an external signal in the form of a ligand or other signal mediator. This creates a conformational change in the GPCR, causing activation of a G protein. Further effect depends on the type of G protein. G proteins are subsequently inactivated by GTPase activating proteins, known as RGS proteins. The ligands that bind and activate these GPCRs include light-sensitive compounds, odors, pheromones, hormones, neurotransmitters, etc. and vary in size from small molecules to peptides to large proteins. When a ligand binds to the GPCR it causes a conformational change in the GPCR, which allows it to act as a guanine nucleotide exchange factor (GEF). The GPCR can then activate an associated G protein by exchanging its bound GDP for a GTP. The G protein's α subunit, together with the bound GTP, can then dissociate from the β and γ subunits to further affect intracellular signaling proteins or target functional proteins directly depending on the α subunit type.

In one implementation, the external receptor 310 may be a photosensitive membrane protein. Photoreceptor proteins are light-sensitive proteins involved in the sensing and response to light in a variety of organisms. Photoreceptor proteins typically consist of a protein moiety and a non-protein photopigment that reacts to light via photoisomerization or photoreduction, thus initiating a change of the receptor protein that triggers the signaling cascade 308. Pigments found in photoreceptors include retinal (retinylidene proteins, for example rhodopsin in animals), flavin (flavoproteins, for example cryptochrome in plants and animals) and bilin (biliproteins, for example phytochrome in plants). One example of engineered use of light-sensitive proteins is found in Tamsir, A. et al., *Robust Multicellular Computing Using Genetically Encoded NOR Gates and Chemical 'Wires'*, 469 Nature 214 (2011).

The external receptor 310, in some implementations, may also be a membrane-bound immunoglobulin (mIg). A membrane-bound immunoglobulin is the membrane-bound form of an antibody. Membrane-bound immunoglobulins are composed of surface-bound IgD or IgM antibodies and associated Ig-α and Ig-β heterodimers, which are capable of signal transduction through the signaling cascade 308 in response to activation by an antigen.

In one implementation, the external receptor 310 may be a Notch protein. The Notch protein spans the cell membrane, with part of it inside and part outside. Ligand proteins binding to the extracellular domain induce proteolytic cleavage and release of the intracellular domain, which enters the cell to modify gene expression. The receptor may be triggered via direct cell-to-cell contact, in which the transmembrane proteins of the cells in direct contact form the ligands that bind the notch receptor. Signals generated by the Notch protein may be carried to an operon by the Notch cascade which consists of Notch and Notch ligands as well as intracellular proteins transmitting the notch signal.

In one implementation, temperature may activate the signaling pathway. Thus, by altering the temperature, expression of the gene 302 may be up or down regulated. Temperature sensing molecules that occur naturally in single celled organisms include heat shock proteins and certain RNA regulatory molecules, such as riboswitches. Heat shock proteins are proteins that are involved in the cellular response to stress. One example of a heat shock protein that responds to temperature is the bacterial protein DnaK. Temperatures elevated above normal physiological range can cause DnaK expression to become up-regulated. DnaK and other heat shock proteins can be utilized for engineered pathways that respond to temperature. Riboswitches are a type of RNA molecule that can respond to temperature in order to regulate protein translation. An example of a temperature-regulated engineered pathway that has utilized a riboswitch can be found in Neupert, J. et al., *Design of simple synthetic RNA thermometers for temperature-controlled gene expression in Escherichia coli.*, 36(19) Nucleic Acids Res., e124, (2008). Another example of a temperature-sensitive molecule that can be utilized to regulate engineered cell pathways is a temperature-sensitive mutant protein. Single mutations can be made to proteins, which cause the proteins to become unstable at high temperatures, yet remain functional at lower temperatures. Methods for synthesizing temperature-sensitive mutant proteins can be found in Ben-Aroya, S. et al., *Making Temperature-Sensitive Mutants*, 470 Methods Enzymology 181 (2010). An example of a temperature-controlled engineered pathway that utilizes a temperature-sensitive mutant can be found in Hussain, F. et al., *Engineered temperature compensation in a synthetic genetic clock*, 111(3) PNAS 972 (2014).

In one implementation, ion concentration or pH may activate the signaling pathway. With signaling pathways of this type, placing a cell in a different ionic environment or altering pH surrounding the cell may be used to control the availability of a given HDR template or enzyme. Examples of cellular sensing molecular mechanisms that detect ionic strength or pH include many viral proteins, such as herpes simplex virus gB, rubella virus envelope protein, influenza hemagglutinin, and vesicular stomatitis virus glycoprotein. An example of a natural cellular pathway that is regulated by pH is penicillin production by *Aspergillus nidulans* as described in Espeso, E. et al., *pH Regulation is a Major Determinant in Expression of a Fungal Penicillin Biosynthetic Gene*, 12(10) EMBO J. 3947 (1993). Another example of a pH-sensitive molecule that can be utilized to regulate engineered cell pathways is a pH-sensitive mutant protein. Single mutations can be made to proteins, which can cause the proteins to become less stable in either acidic or basic conditions. For example, pH-sensitive antibodies can bind to an antigen at an optimal pH, but are unable to bind to an antigen at a non-optimal pH. A technique for creating pH-sensitive antibodies that can be used for engineered signaling pathways can be found in Schroter, C. et al., *A generic approach to engineer antibody pH-switches using combinatorial histidine scanning libraries and yeast display*, 7(1) MAbs 138 (2015). These and other similar sensing mechanisms may be engineered to affect the behavior of a promoter 304 or operator 306.

The gene 302 encodes for gene product 314 that may ultimately be the basis for a number of components in an HDR system. For example, the gene product 314 may be translated into protein, used directly as RNA, or reverse transcribed into DNA. In one implementation, the gene product 314 may be translated into a nuclease 316 that creates DSBs such as, for example, enzyme 104 shown in FIG. 1, or enzyme 200 shown in FIG. 2. The nuclease 316 may be a Cas enzyme such as Cas9, Cas1, or Cas2.

For example, the *S. pyogenes* Cas9 system from the Clustered Regularly-Interspaced Short Palindromic Repeats-associated (CRISPR-Cas) family is an effective genome engineering enzyme that catalyzes double-stranded breaks and generates mutations at DNA loci targeted by a gRNA. The native gRNA is comprised of a 20 nt Specificity Determining Sequence (SDS), which specifies the DNA sequence to be targeted, and is immediately followed by a 80 nt scaffold sequence, which associates the gRNA with Cas9. In addition to sequence homology with the SDS, targeted DNA sequences possess a Protospacer Adjacent Motif (PAM) (5'-NGG-3') immediately adjacent to their 3'-end in order to be bound by the Cas9-sgRNA complex and cleaved. When a double-stranded break is introduced in the target DNA locus in the genome, the break is repaired by either homologous recombination (when a repair template is provided) or error-prone non-homologous end joining (NHEJ) DNA repair mechanisms, resulting in mutagenesis of targeted locus. Even though the normal DNA locus encoding the gRNA sequence is perfectly homologous to the gRNA, it is not targeted by the standard Cas9-gRNA complex because it does not contain a PAM.

In a wild-type CRISPR/Cas system, gRNA is encoded genomically or episomally (e.g., on a plasmid). Following transcription, the gRNA forms a complex with Cas9 endonuclease. This complex is then "guided" by the specificity determining sequence (SDS) of the gRNA to a DNA target sequence, typically located in the genome of a cell. For Cas9 to successfully bind to the DNA target sequence, a region of the target sequence must be complementary to the SDS of the gRNA sequence and must be immediately followed by the correct protospacer adjacent motif (PAM) sequence (e.g. "NGG"). Thus, in a wild-type CRISPR/Cas9 system, the PAM sequence is present in the DNA target sequence but not in the gRNA sequence (or in the sequence encoding the gRNA).

The PAM sequence is typically a sequence of nucleotides located adjacent to (e.g., within 10, 9, 8, 7, 6, 5, 4, 3, 3, or 1 nt of) an SDS sequence). A PAM sequence is "immediately adjacent to" an SDS sequence if the PAM sequence is contiguous with the SDS sequence (that is, if there are no nucleotides located between the PAM sequence and the SDS sequence). In some implementations, a PAM sequence is a wild-type PAM sequence. Examples of PAM sequences include, without limitation, NGG, NGR, NNGRR(T/N), NNNNGATT, NNAGAAW, NGGAG, and NAAAAC, AWG, CC. In some implementations, a PAM sequence is obtained from *Streptococcus pyogenes* (e.g., NGG or NGR). In some implementations, a PAM sequence is obtained from *Staphylococcus aureus* (e.g., NNGRR(T/N)). In some implementations, a PAM sequence is obtained from *Neisseria meningitidis* (e.g., NNNNGATT). In some implementations, a PAM sequence is obtained from *Streptococcus thermophilus* (e.g., NNAGAAW or NGGAG). In some implementations, a PAM sequence is obtained from *Treponema denticola* NGGAG (e.g., NAAAAC). In some implementations, a PAM sequence is obtained from *Escherichia coli* (e.g., AWG). In some implementations, a PAM sequence is obtained from *Pseudomonas auruginosa* (e.g., CC). Other PAM sequences are contemplated. A PAM sequence is typically located downstream (i.e., 3') from the SDS, although in some embodiments a PAM sequence may be located upstream (i.e., 5') from the SDS.

In one implementation, the gene product 314 encodes for gRNA 318 that is used by the Cas enzyme 316 to target a specific DNA sequence. The system may be designed to have all components needed for performing HDR other than the gRNA 318. Thus, transcription of the gRNA in response to a signal provides the last component needed to perform HDR and results in incorporation of an HDR template thereby creating a log of the molecular event. Alternatively, the gRNA 318 may be used not to cut dsDNA but to turn off a promoter through use of CRISPRi guide RNA. CRISPRi guide RNA directs the Cas enzyme 316 to bind to the promoter 304 and prevent transcription of the gene 302. In this design, the presence of a signal would stop the insertion of a particular HDR template.

A gRNA is a component of the CRISPR/Cas system. A "gRNA" (guide ribonucleic acid) herein refers to a fusion of a CRISPR-targeting RNA (crRNA) and a trans-activation crRNA (tracrRNA), providing both targeting specificity and scaffolding/binding ability for Cas9 nuclease. A "crRNA" is a bacterial RNA that confers target specificity and requires tracrRNA to bind to Cas9. A "tracrRNA" is a bacterial RNA that links the crRNA to the Cas9 nuclease and typically can bind any crRNA. The sequence specificity of a Cas DNA-binding protein is determined by gRNAs, which have nucleotide base-pairing complementarity to target DNA sequences. Thus, Cas proteins are "guided" by gRNAs to target DNA sequences. The nucleotide base-pairing complementarity of gRNAs enables, in some embodiments, simple and flexible programming of Cas binding. Nucleotide base-pair complementarity refers to distinct interactions between adenine and thymine (DNA) or uracil (RNA), and between guanine and cytosine. In some embodiments, a gRNA is referred to as a stgRNA. A "stgRNA" is a gRNA that complexes with Cas9 and guides the stgRNA/Cas9 complex to the template DNA from which the stgRNA was transcribed.

The length of a gRNA may vary. In some embodiments, a gRNA has a length of 20 nucleotides to 200 nucleotides, or more. For example, a gRNA may have a length of 20 to 175, 20 to 150, 20 to 100, 20 to 95, 20 to 90, 20 to 85, 20 to 80, 20 to 75, 20 to 70, 20 to 65, 20 to 60, 20 to 55, 20 to 50, 20 to 45, 20 to 40, 20 to 35, or 20 to 30 nt.

In one implementation, the gene product 314 may itself be or may encode for an HDR template 320. The HDR template 320 may be, for example, the HDR template 108 shown FIG. 1 or the HDR template 204 shown in FIG. 2. The gene product 314, although it is a ssRNA, may be capable of functioning as an HDR template 320 due to the ability of RNA to hybridize with DNA. RNA transcript-mediated HDR has been shown to function successfully in eukaryotic cells. See Keskin, H., Shen., Y. et al. *Transcript-RNA-templated DNA recombination and repair,* 515 Nature 436 (2014) and Storici, F. et al., *RNA-templated DNA repair,* 447 Nature 338 (2007). If RNA is used as the HDR template, the cell may be further modified to reduce or remove enzymes that degrade RNA-DNA hybrids. In one implementation, the cell using RNA as the HDR template may be *S. cerevisiae*. Additionally, complementary DNA (cDNA), resulting from reverse-transcription of mRNA, and/or transcript RNA itself may aid DSB repair via HDR. Moreover, splicing of both expressed RNA and potentially of mRNA can change the sequence of RNA that serves as a template for reverse transcriptase to synthesize cDNA. Thus, the cDNA used as an HDR template may have a different sequence, due to splicing, than genomic or other DNA encoding the initial RNA transcript. The gene product 314 may also be converted to ssDNA by reverse transcriptase and used as the HDR template 320 in the form of DNA.

The gene product 314 may also be translated into some other enzyme product 322. The other enzyme product 322 represents another enzyme that may be used for logging of molecular events through HDR. Both DNA Taq polymerase and DNA ligase are examples of other enzyme products used for performing HDR. In a system that lacks one or both of these enzymes, regulated addition through control of gene expression is a way to regulate the ability to perform HDR. Other enzymes such as transcription factors are another type of other enzyme products 322. Transcription factors expressed from a first gene may be used to activate the promoter or operator of a second gene. There may be greater need for addition of other enzyme products 322 in a cell-free system or in a minimal cell than in a biological cell that includes wild-type cellular machinery.

Figure 4:
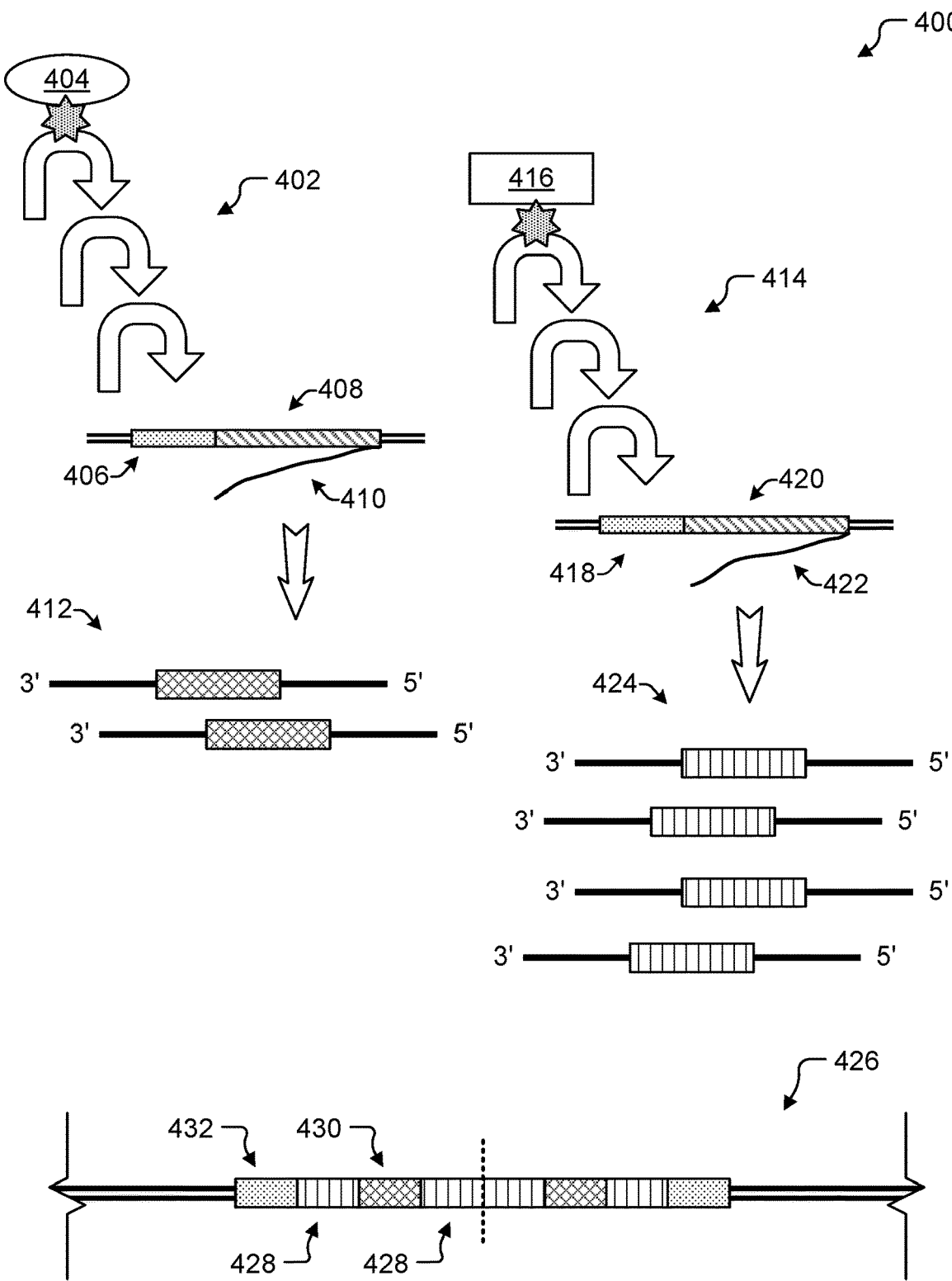
FIG. 4 shows illustrative components for creating a log of multiple signals in a way that records relative signal strength.

FIG. 4 shows a diagram 400 of two illustrative signaling pathways that create different gene products at levels responsive to strengths of the respective signals. A first signaling pathway 402 responds to a first signal 404 by increasing activity of a first promoter 406 which controls transcription of a first gene 408. The first signaling pathway 402 and the first signal 404 may be any of the signaling pathways or types of signals discussed in this disclosure. The first gene 408 creates a first gene product 410 that may be any of the types of gene products shown in FIG. 3. For purposes of illustration, the first gene product 410 is shown as encoding a first HDR template 412. Thus, an increase in the first signal 404 leads to an increase in the synthesis of the first HDR template 412.

Similarly, a second signaling pathway 414 is responsive to a second signal 416 by increasing activity of a second promoter 418 which controls transcription of a second gene 420. The second gene 420 encodes a second gene product 422. The second gene product 422 may be any of the types of gene products discussed in FIG. 3. The second gene product 422 may be the same or a different type of gene product than the first gene product 410. In this diagram 400, the second gene product 422 is shown as a second HDR template 424. The amount of the second HDR template 424 is thus regulated by the strength of the second signal 416.

If, for example, the second signal 416 is stronger and/or more frequent than the first signal 404, the cell will create a greater number of copies of the second HDR template 424 than of the first HDR template 412. The respective signaling pathways 402, 414 and the promoters 406, 418 may be selected to maintain a similar ratio of correspondence between respective signal strengths and synthesis of HDR templates 412, 424. For example, the respective signaling pathways 402, 414 may be the same except for the portion of the signaling pathway directly involved in sensing the primary signal. The promoters 406, 418 may also be similar and different only in one aspect such as the specific transcription factor used to activate the promoter.

In this example, the second HDR template 424 is present at a concentration that is twice as much as the first HDR template 412. This indicates that the second signal 416 is approximately twice as strong as the first signal 404. Because the concentration of the second HDR template 424 is twice that of the first HDR template 412, for each HDR event it is twice as likely that the second HDR template 424 will be integrated into a section of dsDNA 426. Thus, over a prolonged period of iterative integration of HDR templates, it is likely that a sequence 428 from the second HDR template 424 will be twice as common as a sequence 430 from the first HDR template 412. The dsDNA 426 may include, for example, a target site 432 into which either the first HDR template 412 or the second HDR template 424 may be inserted. The relative amount of integration of the sequence 428 from the second HDR template 424 and the sequence 430 of the first HDR template 412 into the dsDNA 426 reflects the relative concentrations of the first HDR template 412 and the second HDR template 424. Specifically, in this example, the sequence 428 of the second HDR template 424 is present twice as often as the sequence 430 from the first HDR template 412. Thus, the first HDR template 412 and the second HDR template 424 integrate into the dsDNA 426 in proportion to their respective concentrations.

If the strength of one or more of signals 404, 416 in this example system changes over time then the relative concentrations of the corresponding HDR templates 412, 424 will also change. This change over time may be observed by analyzing the sequence of the dsDNA 426 and observing throughout different portions of that sequence how the ratio of the sequence 428 of the second HDR template 424 to the sequence 430 of the first HDR template 412 varies. This temporal analysis may be implemented, for example, by analyzing a sliding window of nucleotides of the dsDNA 426 and counting the number of times the sequence 428 from the second HDR template 424 is found and the number of times the sequence 430 of the first HDR template 412 is found. The sliding window may be any length such as, for example 500 nt, 1000 nt, 5000 nt, etc.

Figure 5:
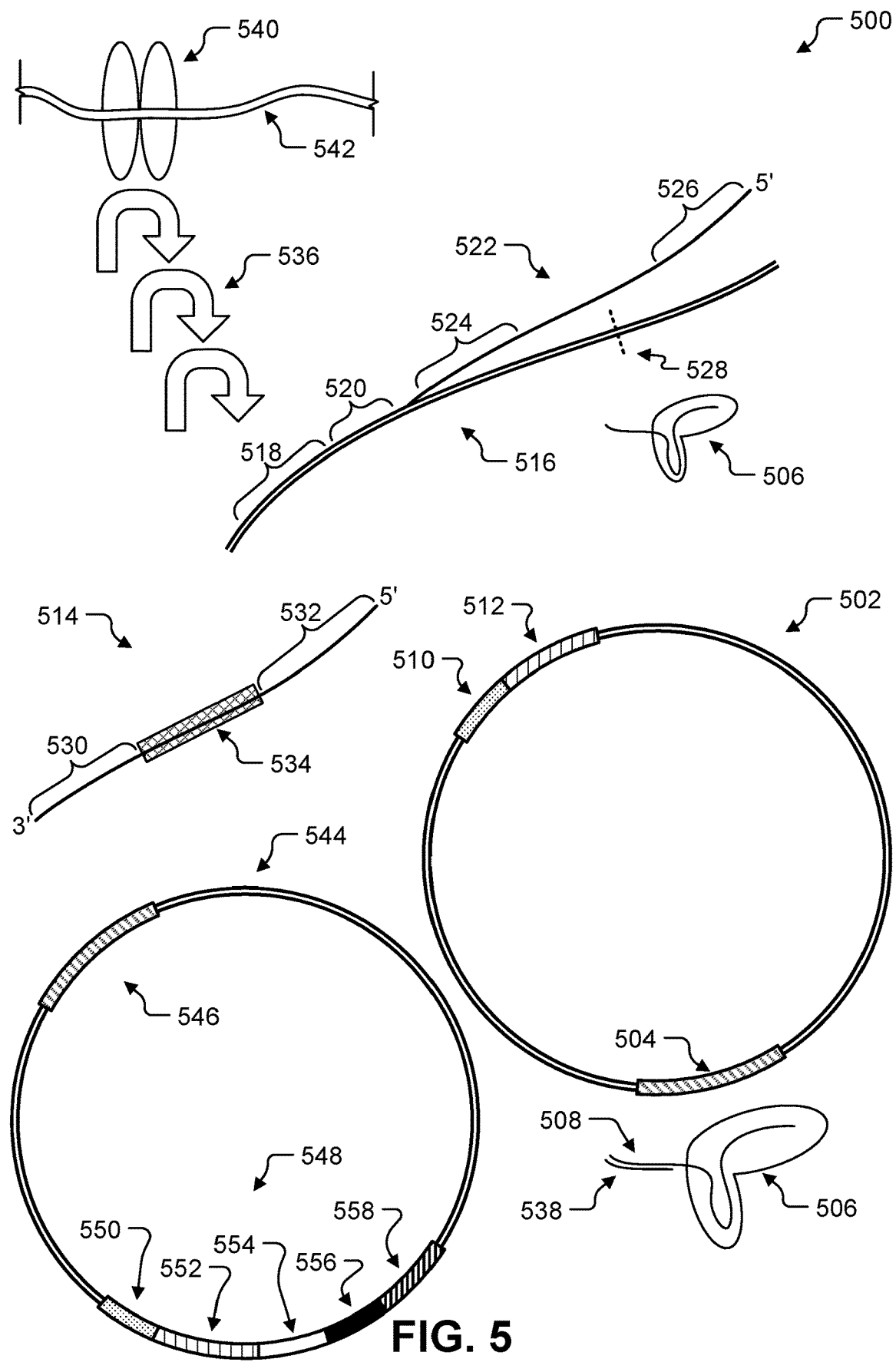
FIG. 5 show illustrative components of a cell for inserting new DNA into existing dsDNA.

FIG. 5 shows an illustrative cell 500 that is capable of heritability storing a log of events experienced by the cell 500. The cell 500 may be an *E. coli* cell, a *Saccharomyces cerevisiae* cell, or a cell from another single-celled organism. It may also be a cell from a multicellular organism grown in culture. Some human cell lines that may be used for cell culture include DU145, H295R, HeLa, KBM-7, LNCaP, MCF-7, MDA-MB-468, PC3, SaOS-2, SH-SY5Y, T47D, THP-1, U87, and National Cancer Institute's 60 cancer cell line panel (NCI60).

The cell 500 may contain a dsDNA molecule 502 that has a first target site 504. The cell 500 may also contain a first enzyme 506 that is configured to create a DSB at a cut site within the first target site 504. For example, the first enzyme 506 may be a CRISPR/Cas system comprising a gRNA 508 that includes a spacer region (also called a proto-spacer element or targeting sequence) of about 20 nt that is complementary to one strand of the dsDNA 502 at the first target site 504.

The dsDNA molecule 502 may also include a promoter 510 and a gene encoding a HDR template 512 such as HDR template 514 shown in this figure.

The dsDNA molecule 502 may be a vector or plasmid introduced to the cell 500 by any suitable method. A "vector" is a polynucleotide molecule, such as a DNA molecule derived, for example, from a plasmid, bacteriophage, yeast or virus, into which a polynucleotide can be inserted or cloned. One type of vector is a "plasmid," which refers to a circular double-stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, lentiviruses, replicative defective lentiviruses, adenoviruses, replication defective adenoviruses, and adeno-associated viruses). Viral vectors also include polynucleotides carried by a virus for transfection into a host cell. Moreover, certain vectors are capable of directing the expression of genes to which they are operatively-linked. Such vectors are referred to herein as "expression vectors." Common expression vectors of utility in recombinant DNA techniques are often in the form of plasmids. Plasmids suitable for expressing embodiments of the present invention, methods for inserting nucleic acid sequences into a plasmid, and methods for delivering recombinant plasmids to cells of interest are known in the art.

A vector may contain one or more unique restriction sites and can be capable of autonomous replication in a defined host cell including a target cell or tissue or a progenitor cell or tissue thereof (e.g. bacterial vectors having a bacterial origin of replication and episomal mammalian vectors), or be integrable with the genome of the defined host such that the cloned sequence is reproducible (e.g., non-episomal mammalian vectors). Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector may comprise specific sequences that allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

Several aspects of the invention relate to vector systems comprising one or more vectors, or vectors as such. Vectors can be designed for expression of transcripts (e.g. nucleic acid transcripts, proteins, or enzymes) in prokaryotic or eukaryotic cells. For example, transcripts can be expressed in bacterial cells such as *Escherichia coli*, insect cells (using baculovirus expression vectors), yeast cells, or mammalian cells. Suitable host cells are discussed further in Goeddel, *Gene Expression Technology: Methods In Enzymology*, 185, Academic Press. San Diego, Calif. (1990). Alternatively, the recombinant expression vector can be transcribed and translated in vitro, for example using T7 promoter regulatory sequences and T7 polymerase.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). Expression of proteins in prokaryotes is most often carried out in *E. coli* with vectors containing constitutive or inducible promoters directing the expression of proteins. Examples of suitable inducible *E. coli* expression vectors include pTrc (Amrann et al., (1988) Gene 69:301-315) and pET 11d (Studier et al., *Gene Expression Technology: Methods In Enzymology* 185, Academic Press, San Diego, Calif. (1990) 60-89).

In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). For other suitable expression systems for both prokaryotic and eukaryotic cells see, e.g., Chapters 16 and 17 of Sambrook, et al., *Molecular Cloning: A*

*Laboratory Manual.* 2nd ed., Cold Spring Harbor Laboratory, Cold Spring Harbor Laboratory Press, Cold Spring Harbor, N.Y., 1989.

Appropriate DNA segments may be inserted into a vector by a variety of procedures. In general, DNA sequences may be inserted into an appropriate restriction endonuclease site(s) by procedures known in the art, which may be performed without undue experimentation by a skilled artisan. A DNA segment in an expression vector may be operatively linked to an appropriate expression control sequence(s) (i.e., a promoter such as 510) to direct synthesis. As used herein, a "promoter" is a DNA regulatory region capable of binding RNA polymerase and initiating transcription of a downstream (3' direction) coding or non-coding sequence. For purposes of defining the present invention, the promoter sequence is bounded at its 3' terminus by the transcription initiation site and extends upstream (5'direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention. A promoter may also contain sub-regions at which regulatory proteins and molecules may bind, such as RNA polymerase and other transcription factors. Promoters may be constitutive, inducible, activatable, repressible, tissue-specific or any combination thereof.

Promoters may include any promoter known in the art for expression either in vivo or in vitro. Promoters which may be used in embodiments of the present invention may include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). The promoters which may be used in embodiments of the present invention may also be inducible, such that expression may be decreased or enhanced or turned "on" or "off." For example, promoters which respond to a particular signal (e.g., small molecule, metabolite, protein, molecular modification, ion concentration change, electric charge change, action potential, radiation, UV, and light) may also be used. Additionally, a tetracycline-regulatable system employing any promoter such as, but not limited to, the U6 promoter or the H1 promoter, may be used. By way of example and not of limitation, promoters which respond to a particular stimulus may include, e.g., heat shock protein promoters, and Tet-off and Tet-on promoters.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter is referred to as an "endogenous promoter."

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR). Contemplated herein, in some embodiments, are RNA pol II and RNA pol III promoters. Promoters that direct accurate initiation of transcription by an RNA polymerase II are referred to as RNA pol II promoters. Examples of RNA pol II promoters for use in accordance with the present disclosure include, without limitation, human cytomegalovirus promoters, human ubiquitin promoters, human histone H2A1 promoters and human inflammatory chemokine CXCL 1 promoters. Other RNA pol II promoters are also contemplated herein. Promoters that direct accurate initiation of transcription by an RNA polymerase III are referred to as RNA pol III promoters. Examples of RNA pol III promoters for use in accordance with the present disclosure include, without limitation, a U6 promoter, a H1 promoter and promoters of transfer RNAs, 5S ribosomal RNA (rRNA), and the signal recognition particle 7SL RNA.

Illustrative promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc. Cells, such as cells in culture, may be transfected or transformed with the dsDNA molecule 502. Transfection is the process of deliberately introducing naked or purified polynucleotides into eukaryotic animal cells. Transformation refers to DNA transfer in bacteria and non-animal eukaryotic cells, including plant cells. Transfection may be performed using viruses or mechanical methods. Viral transfection introduces foreign DNA into a cell by a virus or viral vector. Transfection with a virus may introduce the DNA into the genome of the host cell. Mechanical transfection typically involves opening transient pores or "holes" in the cell membrane to allow the uptake of material. Transfection can be carried out using calcium phosphate (i.e. tricalcium phosphate), by electroporation, microinjection, gene gun, impalefection, hydrostatic pressure, continuous infusion, sonication, lipofection, nanoparticles containing the dsDNA molecule 502 (e.g., mesoporous silica nanoparticles or gold nanoparticles) or by mixing a cationic lipid with the material to produce liposomes which fuse with the cell membrane and deposit their cargo inside. Nanoparticles used to introduce foreign DNA may be ionically charged or have targeting ligands to deliver to specific cells or sites.

One viral transfection technique for transferring genetic material to hard-to-transfect cells is recombinant adeno-associated virus (AAV) delivery. This is a type of viral transduction that does not integrate into the host genome. AAV-based systems have been used successfully to introduce the gene for *S. pyogenes* Cas9 (SpCas9) together with its optimal promoter and polyadenylation signal using the AAVpro CRISPR/Cas9 Helper Free System (AAV2) available from Takara Bio USA, Inc.

Conjugation may also be used to introduce the dsDNA molecule 502 into a cell. Although conjugation in nature occurs more frequently in bacteria, transfer of genetic material from bacterial to mammalian cells is also possible. See Waters V. L., *Conjugation between bacterial and mammalian cells.* 29 (4) Nature Genetics 375 (2001).

The cell 500 may also include a gene 516 under the control of a promoter 518 and an operator 520. The gene 516 may encode a ssRNA sequence 522 comprising a 3'-end sequence 524 and a 5'-end sequence 526. AN HDR template 514 may be generated from the gene 516. In one implementation, the HDR template 514 is the ssRNA sequence 522 itself. The 3'-end sequence 524 and the 5'-end sequence 526 are complementary to one strand of a dsDNA molecule 502 over at least part of a target site 504. Homology between the 3'-end sequence 524 and the 5'-end sequence 526 allows the ssRNA sequence 522 to hybridize with portions of the dsDNA on either side of a DSB created at a cut site in the target site 504.

In implementations in which the gene 516 directly encodes the HDR template 514, the gene 516 will encode a cut site 528 that may be cut by an enzyme such as the first enzyme 506. Unless protected from the enzyme, the cut site 528 in the gene 516 may be unintentionally cut when the enzyme contacts the gene 516.

One technique for protecting the cut site 528 from the first enzyme 506 is physical separation. In a cell-free system, such as one that uses microfluidics, the gene 516 may be maintained in one chamber and the ssRNA sequence 522 may be moved from the chamber containing the gene 516 into a different chamber where the enzyme 506 is present.

Physical separation may also be used in cellular implementations. The gene 516 and the enzyme 506 may be contained in different cellular chambers. In one implementation, the gene 516 may be in the nucleus and the enzyme may be outside the nucleus in the cytoplasm or in another cellular chamber. The gene 516 may remain in the nucleus if it is part of the cell's genome. A nuclear export signal (NES) may be used to keep the enzyme, or other component of the system, out of the nucleus. A NES is a short amino acid sequence of four hydrophobic residues in a protein that targets it for export from the cell nucleus to the cytoplasm through the nuclear pore complex using nuclear transport. Similarly, a nuclear localization signal (NLS) may be used to keep the enzyme in the nucleus. A NLS is an amino acid sequence that tags a protein for import into the cell nucleus by nuclear transport. Typically, a NLS consists of one or more short sequences of positively charged lysines or arginines exposed on the protein surface. Different nuclear localized proteins may share the same NLS. An NLS has the opposite function of a NES. Persons of ordinary skill in the art will be able to modify or engineer a protein such as a nuclease or other enzyme to include a NES or a NLS.

The physical location of RNA in a cell may also be controlled. The ssRNA sequence 522 may be exported from its site of transcription in the nucleus to the cytoplasm or other destination outside the nucleus where the enzyme is present. RNA export is described in Sean Carmody and Susan Wente, *mRNA Nuclear Export at a Glance,* 122 J. of Cell Science 1933 (2009) and Alwin Köhler and Ed Hurt, *Exporting RNA from the Nucleus to the Cytoplasm,* 8 Nature Reviews Molecular Cell Biology 761 (2007).

Splicing may be used in place of or in addition to physical separation to protect the gene 516 from being cut by the enzyme 506. In one implementation, the gene 516 may include a sequence with a portion that is later removed by splicing. This additional portion changes the sequence of nucleotides in the gene 516 so that there is no cut site 528 present. The ssRNA sequence 522 will becomes an HDR template 514 through splicing, which also introduces the cut site 528.

Alternative splicing, or differential splicing, is a regulated process during gene expression that results in a single gene coding for multiple proteins. In this process, particular exons of a gene may be included within or excluded from the final, processed mRNA produced from that gene. Consequently, the proteins translated from alternatively spliced mRNAs will contain differences in their amino acid sequence and, often, in their biological functions. The production of alternatively spliced mRNAs is regulated by a system of trans-acting proteins that bind to cis-acting sites on the primary transcript itself. Such proteins include splicing activators that promote the usage of a particular splice site, and splicing repressors that reduce the usage of a particular site. There are multiple types of alternative splicing including exon skipping, mutually exclusive exons, alternative donor sites, alternative acceptor sites, and intron retention. Exon skipping is one way to cause splicing in the ssRNA sequence 522; in this case, an exon may be spliced out of the primary transcript. Persons having ordinary skill in the art will understand how to design the gene 516 so that it includes a splice site at a specified location. Alternative splicing may be implemented as a technique to prevent creation of a DSB in the gene 516 even if the gene 516 and enzyme 506 are not physically separated.

Self-excising elements may function similarly to splicing. The gene 516 may be designed to include a region that, when transcribed into RNA, includes one or more self-excising elements. Inclusion of the self-excising elements, for example in a way that disrupts the cut site 528, prevents the gene 516 from being recognized by the enzyme and the excision converts the ssRNA sequence 522 into the HDR template 514. One type of self-excising elements are ribozymes, which are RNA enzymes that function as reaction catalysts. Ribozymes are RNA sequences that catalyze a (trans-esterification) reaction to remove the ribozyme sequence itself from the rest of the RNA sequence. Essentially these are considered introns, which are intragenic regions spliced from mRNA to produce mature RNA with a continuous exon (coding region) sequence. Self-excising introns/ribozymes consist of group I and group II introns. Many group I introns in bacteria are known to self-splice and maintain a conserved secondary structure comprised of a paired element which uses a guanosine (GMP, GDP, or GTP) cofactor. An example of a group I intron is the *Staphylococcus* phage twort.ORF143. Group I and group II introns are considered self-splicing because they do not require proteins to initialize the reaction. Self-excising sequences are known and one of ordinary skill in the art will understand how to include a self-excising sequence in the gene 516. Aspects of self-excising ribozymes are shown in *In Vivo Protein Fusion Assembly Using Self Excising Ribozyme* available at 2011.igem.org/Team:Waterloo (last visited Mar. 3, 2017).

A series of homologous bridges may also be used to generate a recombinant sequence that is the gene template for the ssRNA sequence 522. The homologous bridges may be present in the DNA at various, separate locations so that the gene 516 does not include a cut site 528. This technique is also known as multi-fragment cloning or extension cloning. The final HDR template 514 is made up of transcripts of the multiple overlapping segments. One suitable technique for combining the multiple-overlapping fragments into the HDR template 514 is Sequence and Ligation-Independent Cloning (SLIC). This technique is described in Mamie Li and Stephen Elledge, *Harnessing Homologous Recombination in vitro to Generate Recombinant DNA Via SLIC*, 4 Nature Methods 250 (2007). Another suitable technique for joining multiple-overlapping fragments is provided by Jiayuan Quan and Jingdong Tian, *Circular Polymerase Extension of Cloning of Complex Gene Libraries and Pathways*, 4(7) PLoS ONE e6441 (2009).

Methylation may be used to protect HDR templates from premature cutting by restriction enzymes because some restriction enzymes do not cut methylated DNA. Other nucleases such as Cas9 may also be prevented from cutting by methylation of a cutting region or PAM recognition site. DNA methylation is a process by which methyl groups are added to the DNA molecule. Methylation can change the activity of a DNA segment without changing the sequence. Two of DNA's four bases, cytosine and adenine, can be methylated. A methylase is an enzyme that recognizes a specific sequence and methylates one of the bases in or near that sequence. Methylation may be controlled by epigenetic editing using a targeting device that is a sequence-specific DNA binding domain which can be redesigned to recognize desired sequences. The targeting device may be fused to an effector domain, which can modify the epigenetic state of the targeted locus. Techniques for using epigenetic editing will be understood by one of ordinary skill in the art. Epigenome manipulations are described in Park, et al., *The epigenome: the next substrate for engineering.* 17 Genome Biology 183 (2016). HDR templates made of RNA may also be modified by methylation. S. Lin and R. Gregory, *Methyltransferases modulate RNA stability in embryonic stem cells,* 16(2) Nature Cell Biology 129 (2014).

In one implementation, the HDR template 514 is a ssDNA sequence complementary to the ssRNA sequence 522. The ssDNA sequence may be created by reverse transcriptase reading (RT) the ssRNA sequence 522 and synthesizing a complementary ssDNA sequence. RT is an enzyme used to generate cDNA from an RNA template, a process termed reverse transcription. RT is widely used in the laboratory to convert RNA to DNA for use in procedures such as molecular cloning, RNA sequencing, PCR, and genome analysis. RT enzymes are widely available from multiple commercial sources. Procedures for use of RT is well known to those of ordinary skill in the art.

The 3'-end sequence 530 and the 5'-end sequence 532 of the HDR template 514 are homologous to one strand of the dsDNA 502 over at least a portion of the first target site 504. The HDR template 514, in both ssDNA and ssRNA implementations, includes a middle portion 534 that, when incorporated into the dsDNA 502, acts as a record on a signal detected by the engineered signaling pathway 536. In an implementation, the middle portion 534 also introduces another target site as described elsewhere in this disclosure.

Enzyme 506 is illustrated here as a CRISPR/Cas complex with gRNA 508. Other types of enzymes discussed above may be used instead of the CRISPR/Cas complex. The single-stranded tail of the gRNA 508 may be extended with a sequence complementary to all or part of the HDR template 514. The HDR template 514 may partially hybridize to the tail of the gRNA 508 forming a double-stranded region 538. This brings a copy of the HDR template 514 into close physical proximity with the location of the DSB created by the CRISPR/Cas complex 506 which can increase HDR efficiency.

The extended tail of the gRNA 508 may also be designed so that it matches the binding domain of a transcription activator-like effector (TALE) protein. The TALE protein may also have a binding domain complementary to the HDR template 514. This will also bring the HDR template into close proximity with the location of the DSB. The tail of the gRNA 508 may be extended to create regions for attachment of multiple copies of the HDR template 514 or TALE proteins.

TALE proteins are proteins secreted by *Xanthomonas* bacteria via their type III secretion system when the bacteria infect various plant species. These proteins can bind promoter sequences in the host plant and activate the expression of plant genes that aid bacterial infection. They recognize plant DNA sequences through a central repeat domain consisting of a variable number of about 34 amino acid repeats. There appears to be a one-to-one correspondence between the identity of two critical amino acids in each repeat and each DNA base in the target site. The most distinctive characteristic of TAL effectors is a central repeat domain containing between 1.5 and 33.5 repeats that are usually 34 nt in length (the C-terminal repeat is generally shorter and referred to as a "half repeat"). A typical repeat sequence may be shared across many TALE proteins but the residues at the $12^{th}$ and $13^{th}$ positions are hypervariable (these two amino acids are also known as the repeat variable diresidue or RVD). This simple correspondence between amino acids in TAL effectors and DNA bases in their target sites makes them useful for protein engineering applications.

Subsequent to creation of a DSB in the target site 504, the molecule 538 that has hybridized to the tail of the gRNA 508 may be released. In some implementations, introduction of a nucleotide sequence complementary to the tail of the gRNA 508 or binding domain of the TALE protein may compete with the attached molecule 538 and cause disassociation of the HDR template 514, TALE protein, or other molecule. This competition may cause the HDR template 514 to become available for binding to the dsDNA 502 on either side of the DSB.

The cell 500 may also include one or more engineered signaling pathways 536. As used herein, "engineered signaling pathway" includes any pathway in which at least one portion of the pathway is intentionally modified with molecular biology techniques to be different from the wild type pathway and a signal (intracellular or extracellular) causes a change in a rate of transcription of a gene. The engineered signaling pathway 536 may induce a promoter such as the promoter 510 described above. The engineered signaling pathway 536 may also cause a transcription factor to bind to an operator such as the operator 520 described above and prevent transcription. In one implementation, the gene affected by the engineered signaling pathway 536 may be the gene 516 that encodes for the ssRNA sequence 522. Thus, the engineered signaling pathway 536 may function to control an amount of the HDR template 514 available in the cell 500. In one implementation, the gene affected by the engineered signaling pathway 536 may encode for an enzyme that creates DSBs in dsDNA such as enzyme 506. Thus, the number of enzymes which create DSBs in the target sites 504 may be regulated by the engineered signaling pathway 536. The engineered signaling pathway 536 may control the transcription of genes that encode other proteins associated with HDR.

The cell 500 may include multiple different engineered signaling pathways 536 each responding to a unique signal and each promoting or repressing expression of genes responsible for the creation of the HDR templates 522 and/or enzymes 506. Thus, intracellular or extracellular signals may be used to vary the levels of HDR templates 514 and/or enzymes 506 in the cell 500 thereby changing which target sites 504 are cut and which sequences are used to repair DSBs through HDR. Responding by up or down regulating any of multiple promoters and/or operators allows the cell 500 to record a log in its DNA of events and complex interactions of events sensed by engineered signaling pathways. In one implementation, the engineered signaling pathway 536 may include an external receptor 540 that can detect extracellular signals across a membrane 542. The membrane 542 may be a cell wall, lipid bilayer, artificial cell wall, or synthetic membrane.

The cell 500 may also include one or more additional dsDNA molecules 544 that may include a second target site 546. Similar to the first dsDNA molecule 502, the additional dsDNA molecule 544 may include only a single instance of the second target site 546. Alternatively, the additional dsDNA molecule 544 may include multiple copies of the same target site or multiple different target sites. The additional dsDNA molecule 544 may be introduced to the cell 500 by any of the techniques described above. In some implementations, the first dsDNA molecule 502 and the additional dsDNA molecule 544 may be introduced by the same procedure. A ratio of the first dsDNA molecule 502 and the additional dsDNA molecule 544 in the cell 500 may be controlled by regulating the respective copies of the dsDNA molecules added to the cell 500.

The additional dsDNA molecule 544 and the second target site 546 may have identical or similar sequences to the first dsDNA molecule 502 and the first target site 504. Thus, the additional dsDNA molecule 544 may be thought of as a "copy" of the first dsDNA molecule 502 in some implementations. This additional copy of an identical or similar molecule may provide redundancy by creating a second log that, absent errors, will record the same series of events in both dsDNA molecules 502, 544. In one implementation, the additional dsDNA molecule 544 may include a target site 546 with a different sequence than the first target site 504 in the first dsDNA molecule 502. Having different target sites 504, 546 in different dsDNA molecules 502, 544 allows for simultaneous, or alternating, encoding of binary data in two different encoding schemes. The two different encoding schemes may be non-overlapping or "orthogonal" so that the enzymes and HDR templates associated with one encoding scheme do not interact with the dsDNA molecule used for the other encoding scheme. For example, insertion of DNA into the first target site 504 may record the presence of signals related to temperature and insertion of DNA into the second target site 546 may record the presence of signals related to light levels. It is understood, that in actual implementation there may be many hundreds or thousands of dsDNA molecules with respective target sites. There may also be a corresponding number of different encoding schemes and different sequences for the respective target sites for creating a detailed log of multiple different signals.

In an implementation, the additional dsDNA molecule 544 may include an operon 548 that encodes components used for logging molecular events. An operon is a contiguous region of DNA that includes cis-regulatory regions (e.g., repressors, promoters) and the coding regions for one or more genes or functional mRNAs (e.g., siRNA, tracrRNA, gRNA, shRNA, etc). The operon 548 may be delivered in a circular vector, such as the additional dsDNA molecule 544, or may be inserted into genomic DNA of the cell 500 through gene editing techniques known to those of skill in the art. In an implementation, the operon 548 may include genes encoding all of the components used by the cell 500 for performing HDR. Thus, addition of a vector such as the dsDNA molecule 544 may enable a cell 500 that includes the necessary engineered signaling pathway 536 to respond to detected signals by adding HDR templates 522 into a target site 546 on the added dsDNA molecule 544. In this implementation, the HDR template 514, the enzyme 506, and any accessory proteins may be supplied by genes included in the operon 548. The genes in the operon 548 may be under the control of a single promoter 550 and operator 552.

In an implementation, the operon 548 may include any or all of a gene encoding an HDR template 554, a gene encoding an enzyme configured to make DSBs 556, and a gene that encodes a tracking molecule 558 (e.g., RNA, DNA, or protein) for monitoring "state" as described below. An operon 548 that includes genes encoding all of the products for performing HDR may be added to a cell-free system on a circular dsDNA molecule 544 that also includes a target site 546 to provide complete instructions for a molecular event logging system on one molecule.

The term "operably linked" as used herein means placing a gene under the regulatory control of a promoter, which then controls the transcription and optionally the translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived. "Constitutive promoters" are typically active, i.e., promote transcription, under most conditions. "Inducible promoters" are typically active only under certain conditions, such as in the presence of a given molecule factor (e.g., IPTG) or a given environmental condition (e.g., particular $CO_2$ concentration, nutrient levels, light, heat). In the absence of that condition, inducible promoters typically do not allow significant or measurable levels of transcriptional activity. For example, inducible promoters may be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters are known to one of skill in the art.

Illustrative eukaryotic promoters known to one of skill in the art are listed below.

| Promoter | Primarily used for | Description | Additional considerations |
|---|---|---|---|
| CMV | General expression | Strong mammalian expression promoter from the human cytomegalovirus | May contain an enhancer region. Can be silenced in some cell types. |
| EF1a | General expression | Strong mammalian expression from human elongation factor 1 alpha | Tends to give consistent expression regardless of cell type or physiology. |
| SV40 | General expression | Mammalian expression promoter from the simian vacuolating virus 40 | May include an enhancer. |
| PGK1 (human or mouse) | General expression | Mammalian promoter from phosphoglycerate kinase gene. | Widespread expression, but may vary by cell type. Tends to resist promoter down regulation due to methylation or deacetylation. |
| Ubc | General expression | Mammalian promoter from the human ubiquitin C gene | As the name implies, this promoter is ubiquitous. |
| human beta actin | General expression | Mammalian promoter from beta actin gene | Ubiquitous. Chicken version is commonly used in promoter hybrids. |
| CAG | General expression | Strong hybrid mammalian promoter | Contains CMV enhancer, chicken beta actin promoter, and rabbit beta-globin splice acceptor. |
| TRE | General expression | Tetracycline response element promoter | Typically contains a minimal promoter with low basal activity and several tetracycline operators. Transcription can be turned on or off depending on what tet transactivator is used. |
| UAS | General expression | Drosophila promoter containing Gal4 binding sites | Requires the presence of Gal4 gene to activate promoter. |
| Ac5 | General expression | Strong insect promoter from Drosophila Actin 5c gene | Commonly used in expression systems for Drosophila. |
| Polyhedrin | General expression | Strong insect promoter from baculovirus | Commonly used in expression systems for insect cells. |
| CaMKIIa | Gene expression for optogenetics | Ca2+/calmodulin-dependent protein kinase II promoter | Used for neuronal/CNS expression. Modulated by calcium and calmodulin. |
| GAL1, 10 | General expression | Yeast adjacent, divergently transcribed promoters | Can be used independently or together. Regulated by GAL4 and GAL 80. |
| TEF1 | General expression | Yeast transcription elongation factor promoter | Analogous to mammalian EF1a promoter. |
| GDS | General expression | Strong yeast expression promoter from glyceraldehyde 3-phosphage dehydrogenase | Very strong, also called TDH3 or GAPDH. |
| ADH1 | General expression | Yeast promoter for alcohol dehydrogenase I | Full length version is strong with high expression. Truncated promoters are constitutive with lower expression. |
| CaMV35S | General expression | Strong plant promoter from the Cauliflower Mosaic Virus | Active in dicots, less active in monocots, with some activity in animal cells. |
| Ubi | General expression | Plant promoter from maize ubiquitin gene | Gives high expression in plants. |
| H1 | small RNA expression | From the human polymerase III RNA promoter | May have slightly lower expression than U6. May have better expression in neuronal cells. |
| U6 | small RNA expression | From the human U6 small nuclear promoter | Murine U6 is also used, but may be less efficient. |

Illustrative prokaryotic promoters known to one of skill in the art are listed below.

| Promoter | Primarily used for | Description | Expression | Additional considerations |
|---|---|---|---|---|
| T7 | in vitro transcription/ general expression | Promoter from T7 bacteriophage | Constitutive, but requires T7 RNA polymerase. | When used for in vitro transcription, the promoter drives either the sense OR antisense transcript depending on its orientation to your gene. |
| T7lac | High levels of gene expression | Promoter from T7 bacteriophage plus lac operators | Negligible basal expression when not induced. Requires T7 RNA polymerase, which is also controlled by lac operator. Can be induced by IPTG. | Commonly found in pET vectors. Very tightly regulated by the lac operators. Good for modulating gene expression through varied inducer concentrations. |
| Sp6 | in vitro transcription/ general expression | Promoter from Sp6 bacteriophage | Constitutive, but requires SP6 RNA polymerase. | SP6 polymerase has a high processivity. When used for in vitro transcription, the promoter drives either the sense OR antisense transcript depending on its orientation to your gene. |
| araBAD | General expression | Promoter of the arabinose metabolic operon | Inducible by arabinose and repressed catabolite repression in the presence of glucose or by competitive binding of the anti-inducer fucose | Weaker. Commonly found in pBAD vectors. Good for rapid regulation and low basal expression; however, not well-suited for modulating gene expression through varied inducer concentrations. |
| trp | High levels of gene expression tryptophan operon | Promoter from E. coli | Repressible | Gets turned off with high levels of cellular tryptophan. |
| lac | General expression | Promoter from lac operon | Constitutive in the absence of lac repressor (lacI or lacIq). Can be induced by IPTG or lactose. | Leaky promoter with somewhat weak expression. lacIq mutation increases expression of the repressor 10x, thus tightening regulation of lac promoter. Good for modulating gene expression through varied inducer concentrations. |
| Ptac | General expression | Hybrid promoter of lac and trp | Regulated like the lac promoter | Contains −35 region from trpB and −10 region from lac. Very tight regulation. Good for modulating gene expression through varied inducer concentrations. Generally better expression than lac alone. |
| pL | High levels of gene expression | Promoter from bacteriophage lambda | Can be temperature regulatable | Often paired with the temperature sensitive cI857 repressor. |

Figure 6:
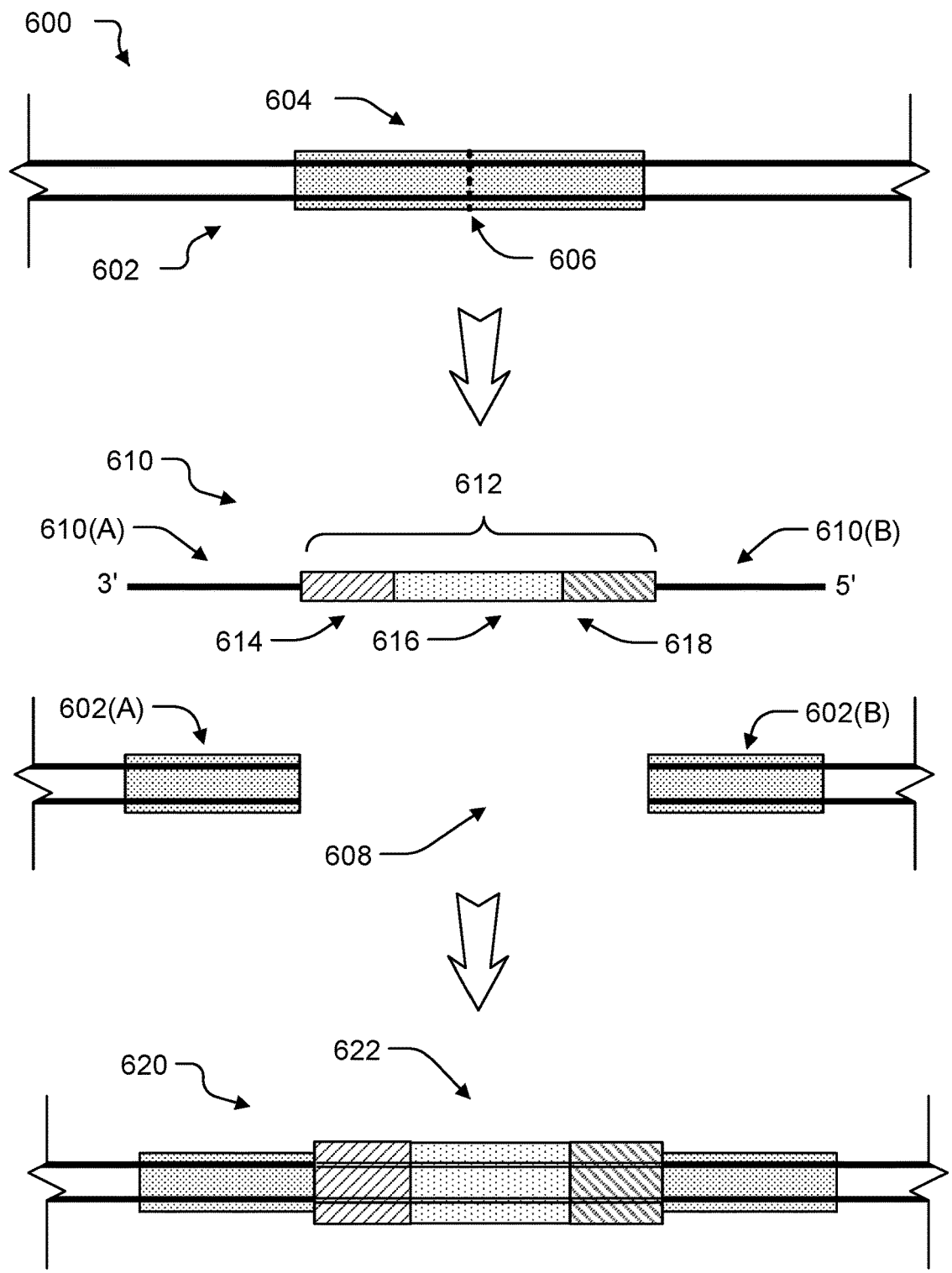
FIG. 6 shows a diagram illustrating insertion of a first HDR template into a gene.

FIG. 6 shows a diagram 600 illustrating insertion of a first HDR template into a gene 602. The gene 602 can include a target site 604. The target site 604 can include a sequence of nucleotides that can direct an enzyme (not shown) to create a DSB in the gene 602 within the target site 604 at a cut site 606. The target site 604 can, in some cases, be part of a pre-existing sequence of nucleotides that is recognized by one or more enzymes to create the DSB. In other situations, the target site 604 can be added to the gene 602 by conventional genetic engineering techniques such that the DSB can be produced by one or more enzymes. Additionally, the gene 602 can include a single target site 604 in some implementations, while in other cases (not shown), the gene 602 can include multiple target sites 604. The enzyme used to create the DSB can include enzymes described previously in this application, such as restriction enzymes, homing endonucleases, zinc-finger nucleases, transcription activator-like effector nucleases, CRISPR/Cas, and NgAgo.

The DSB produced by the enzyme in the target site 604 produces a gap 608 and two subsequences 602(A) and 602(B) on either side of the gap 608. In various implementations, the target site 604 can include from about 10 nucleotides to about 40 nucleotides with each of the subsequences 602(A) and 602(B) having from about 5 nucleotides to about 20 nucleotides depending on the location of the cut site 606 within the target site 604. In some examples, the cut site 604 can be located in a middle portion of the target site 604. Alternatively, the cut site 604 can be included closer to the 3' end of the target site 604 or closer to the 5' end of the target site 604. The subsequences 602(A) and 602(B) can include the same sequences of nucleotides in particular implementations, but different sequences of nucleotides in additional implementations.

After the gap 608 is created by the DSB, a first HDR template 610 moves into proximity with the subsequences 602(A) and 602(B) and the gap 608. As described previously in this application, the first HDR template 610 can be a single strand of DNA or a single strand of RNA that is used to repair the DSB through homologous directed repair. A 3'-end sequence 610(A) of the first HDR template 610 can be complementary to the first subsequence 602(A) and a 5'-end sequence 610(B) of the first HDR template 610 can be complementary to the second subsequence 602(B). The 3'-end 610(A) and the 5'-end 610(B) can also have a length that is similar to or the same as the lengths of the first subsequence 602(A) and the second subsequence 602(B). Accordingly, the 3'-end sequence 610(A) and the 5'-end sequence 610(B) can include about 5 nucleotides to about 20 nucleotides.

Between the 3'-end sequence 610(A) and the 5'-end sequence 610(B), the first HDR template 610 can include middle portion 612 that includes a first splicing region 614, a barcode sequence 616, and a second splicing region 618. The first splicing region 614 can include a sequence of nucleotides that is recognized by an enzyme that can create a cut within the first splicing region 614. Additionally, the second splicing region 618 can include a sequence of nucleotides that is recognized by an enzyme that can create a cut within the second splicing region 618. In some implementations, the first splicing region 614 and the second splicing region 618 can include sequences of nucleotides that are recognized by a spliceosome. The spliceosome can create cuts at specific locations within the first splicing region 614 and the second splicing region 618. In an illustrative example, the first splicing region 614 can be an acceptor site of an intron and include an AG sequence that indicates a first cut site for a spliceosome. The first splicing region 614 can include a region that is high in pyrimidines, such as a polypyrimidine region. Additionally, the first splicing region 614 can include a branch sequence. The branch sequence can be from 20 to 50 nucleotides away (i.e., toward the 5'-end) from the 3'-end of the HDR template and include at least one adenine along with pyrimidines, and at least one additional purine. The second splicing region 618 can be a donor site of an intron and include a GU sequence that indicates a second cut site for a spliceosome in addition to additional purines and pyrimidines.

The barcode sequence 616 can include a number of nucleotides that comprise a sequence that corresponds to the gene 602. In some implementations, the barcode sequence 616 can uniquely correspond to the gene 602. That is, for each gene for which its expression is being analyzed within a given group of genes, a unique barcode sequence can be identified. The barcode sequence 616 can include any number of nucleotides that allows for identification of the gene such as, for example, at least 20 nucleotides, at least 50 nucleotides, at least 75 nucleotides, or at least 100 nucleotides. In some illustrative examples, the barcode sequence 616 can include from about 20 nucleotides to about 250 nucleotides, from about 20 nucleotides to about 100 nucleotides, from about 50 nucleotides to about 150 nucleotides, or from about 100 nucleotides to about 200 nucleotides.

As the first HDR template 610 moves into proximity with the first subsequence 602(A) and the second subsequence 602(B), HDR can repair the DSB and produce a modified gene 620 from the gene 602. As explained previously with respect to FIG. 1 and FIG. 2, the first HDR template 610 can displace one strand of the first subsequence 602(A) and the second subsequence 602(B) and pair with the other strand of the first subsequence 602(A) and the second subsequence 602(B) through the formation of a D loop and using DNA ligase. Once the first HDR template 610 is used to repair the DSB of a first strand of the gene 602, DNA polymerase can be utilized to produce a number of nucleotides complementary to those of the middle portion, thus repairing the second strand of the gene 602 at the DSB to produce dsDNA that is the modified gene 620. The middle portion 612 of the first HDR template 610 can be used to produce a gene expression region 622 of the modified gene 620 that includes at least the first splicing region 614, the barcode sequence 616, and the second splicing region 618.

Figure 7:
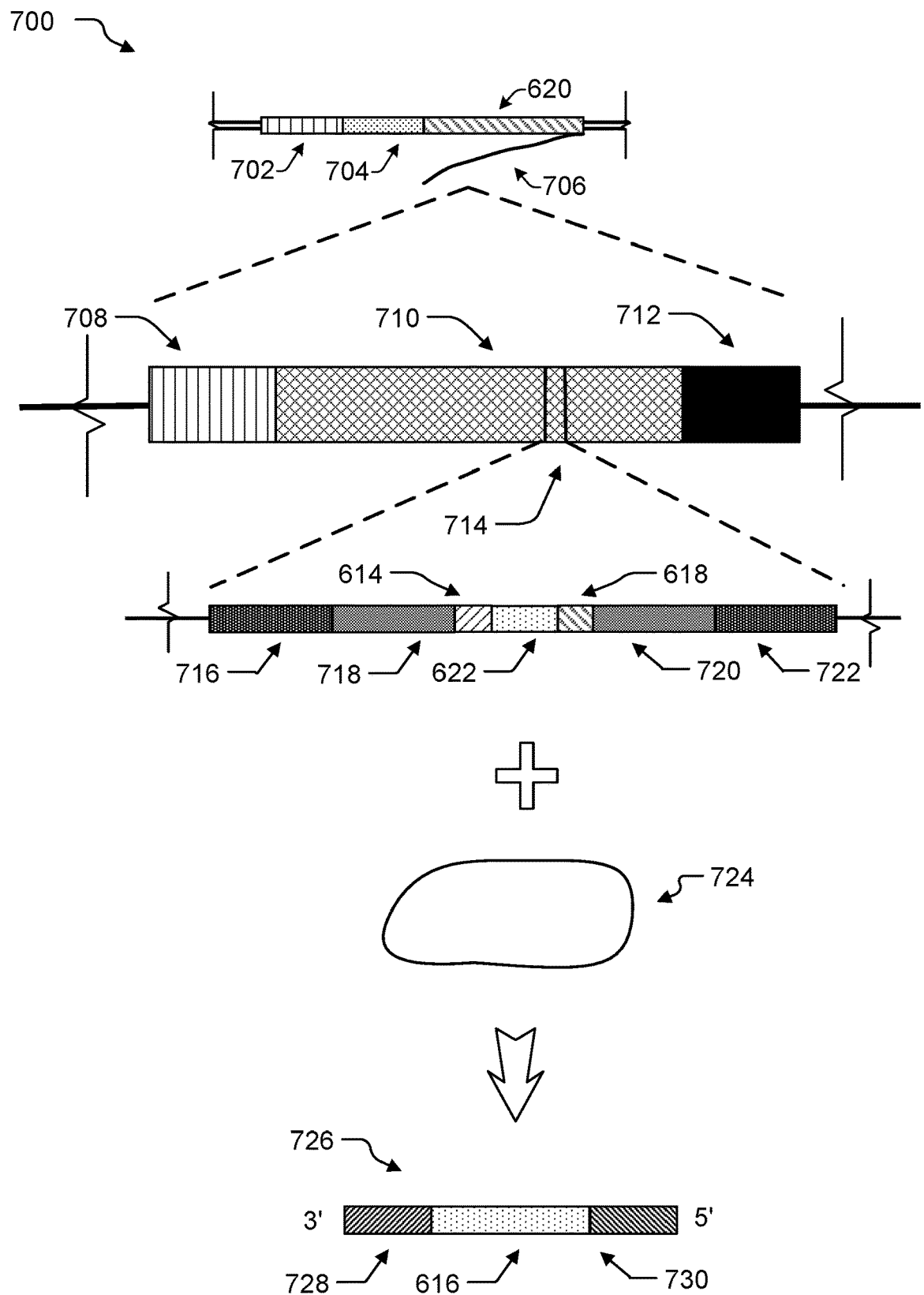
FIG. 7 shows a diagram illustrating the splicing of a second HDR template including a barcode sequence from an RNA precursor produced from the gene.

FIG. 7 shows a diagram 700 illustrating the splicing of a second HDR template including a barcode sequence from an RNA precursor produced from the modified gene 620. The modified gene 620 can be under the control of a promoter 702 and an operator 704. As explained previously with respect to FIG. 3, the promoter 702 can be used to implement the expression of the modified gene 620 and the operator 704 can turn off the expression of the modified gene 620. The operator 704 can be deactivated and the promoter 702 can be activated using a signaling pathway that is activated in response to a stimulus. The stimulus can include one or more of the presence of a molecule, such as a protein or enzyme, the absence of a molecule, or a condition to which the modified gene 620 is exposed. In some cases, the modified gene 620 can be exposed to a condition that affects the activation of the promoter 702 and/or the operator 704, such as a temperature range, a pH range, exposure to a range of electromagnetic radiation, and the like.

In response to being activated, the modified gene 620 can produce a gene product 706. In the illustrative example of FIG. 7, the gene product 706 is an RNA precursor. In some implementations, the RNA precursor can be an mRNA precursor. The gene product 706 can have a structure that includes a 5' UTR 708, a coding region 710, and a 3' UTR 712. An example portion 714 of the coding region 710 can include a first intron 716, a first exon, 718, the gene expression region 622, a second exon 720, and a second intron 722.

The gene product 706 can be contacted with an enzyme 724 that removes portions of the sequence of the gene product 706. For example, the enzyme 724 can include a spliceosome that removes introns from an mRNA precursor. In the illustrative example of FIG. 7, the enzyme 724 is used to remove the gene expression region 622 from the gene product 706. In various implementations, the gene expression region 622 can include a sequence of nucleotides that is recognized by the enzyme 724. In particular implementations, the first splicing region 614 and the second splicing region 618 can include nucleotide sequences that are recognized by the enzyme 724 such that the enzyme 724 can cut the gene expression region 622 at both the first splicing region 614 and the second splicing region 618. In an illustrative example, the gene expression region 622 can be designed so that the first splicing region 614 and the second splicing region 618 are the same as or similar to splicing regions that are recognized by one of the many spliceosomes utilized to splice introns from mRNA precursors. Additionally, the barcode region 616 of the gene expression region 622 can also include a nucleotide sequence that does not interfere with the splicing actions performed by the enzyme 724. In certain situations, the gene expression region 622 can include a nucleotide sequence that corresponds partially to one or more sequences of known introns that can be spliced by the enzyme 724.

The splicing of the gene expression region 622 by the enzyme 724 can produce a second HDR template 726. The second HDR template 726 can include a first end region 728, the barcode sequence 616, and a second end region 730. In some cases, the first end region 728 can include at least part of the nucleotide sequence that comprises the first splicing region 614 and the second end region 730 can include at least part of the nucleotide sequence that comprises the second splicing region 618. In particular implementations, the first end region 728 can include the nucleotide sequence of the first splicing region 614 minus one or more nucleotides removed by the enzyme 724. Additionally, the second end region 730 can include the nucleotide sequence of the second splicing region 618 minus one or more nucleotides removed by the enzyme 724.

Figure 8:
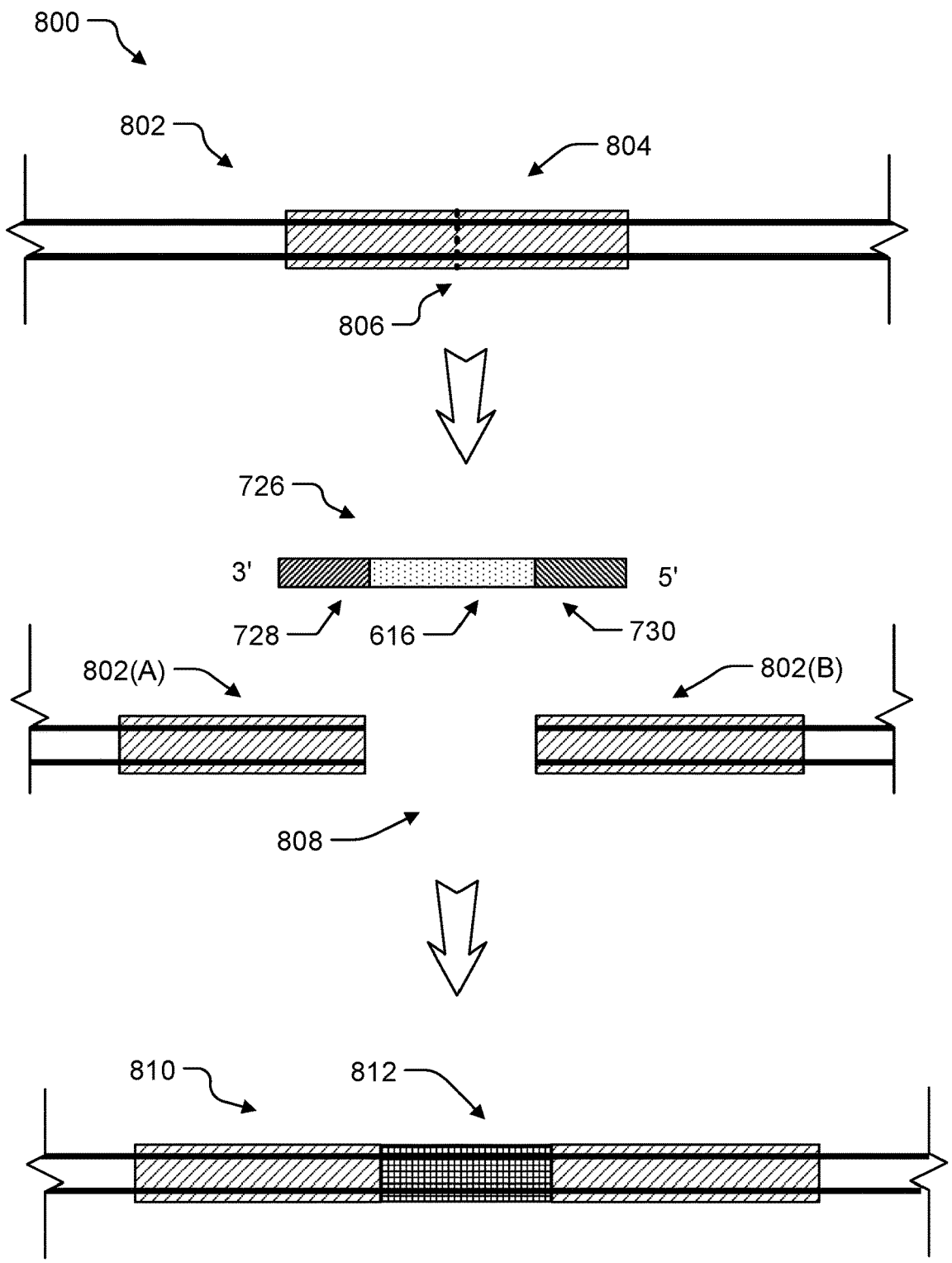
FIG. 8 shows a diagram illustrating insertion of the second HDR template into an additional polynucleotide.

FIG. 8 shows a diagram 800 illustrating insertion of the second HDR template 726 into an additional polynucleotide 802. The additional polynucleotide 802 can be dsDNA. In some cases, the additional polynucleotide 802 can include genomic DNA inside a living prokaryotic or eukaryotic cell. In other situations, the additional polynucleotide 802 can include dsDNA introduced into a living cell, such as a plasmid or vector. In still other examples, the additional polynucleotide 802 can include dsDNA in a cell-free system. The additional polynucleotide 802 can include linear or circular dsDNA prior to undergoing an HDR operation. The additional polynucleotide 802 can have a sequence that is different from the sequence of the gene 602.

The additional polynucleotide 802 can include a target site 804. The target site 804 can include a sequence of nucleotides that can direct an enzyme (not shown) to create a DSB in the additional polynucleotide 802 within the target site 804 at a cut site 806. The target site 804 can, in some cases, be part of a pre-existing sequence of nucleotides that is recognized by one or more enzymes to create the DSB. In other situations, the target site 804 can be added to the additional polynucleotide 802 by conventional genetic engineering techniques such that the DSB can be produced by one or more enzymes. Additionally, the additional polynucleotide 802 can include a single target site 804 in some implementations, while in other cases (not shown), the additional polynucleotide 802 can include multiple target sites 804. The enzyme used to create the DSB can include enzymes described previously in this application, such as restriction enzymes, homing endonucleases, zinc-finger nucleases, transcription activator-like effector nucleases, CRISPR/Cas, and NgAgo.

The DSB produced by the enzyme in the target site 804 produces a gap 808 and two subsequences 802(A) and 802(B) on either side of the gap 808. In various implementations, the target site 804 can include from about 10 nucleotides to about 40 nucleotides with each of the subsequences 802(A) and 802(B) having from about 5 nucleotides to about 20 nucleotides depending on the location of the cut site 806 within the target site 804. In some examples, the cut site 806 can be located in a middle portion of the target site 804. Alternatively, the cut site 806 can be included closer to the 3'-end of the target site 804 or closer to the 5'-end of the target site 804. The subsequences 802(A) and 802(B) can include the same sequences of nucleotides in particular implementations, but different sequences of nucleotides in additional implementations.

After the gap 808 is created by the DSB, the second HDR template 726 moves into proximity with the subsequences 802(A) and 802(B) and the gap 808. As described previously in this application, the second HDR template 726 can be a single stranded polynucleotide sequence that is used to repair the DSB through homologous directed repair. The first end region 728 can be complementary to the first subsequence 802(A) and the second end region 730 can be complementary to the second subsequence 802(B). The first end region 728 and the second end region 730 can also have a length that is similar to or the same as the lengths of the first subsequence 802(A) and the second subsequence 802(B). Accordingly, the first end region 728 and the second end region 730 can include about 5 nucleotides to about 20 nucleotides. Between the first end region 728 and the second end region 730, the second HDR template 726 includes the barcode region 616 that includes a sequence of nucleotides that corresponds to the gene 602.

As the second HDR template 726 moves into proximity with the first subsequence 802(A) and the second subsequence 802(B), HDR can be used to repair the DSB. In some cases, uptake of the second HDR template 726 by the additional polynucleotide 802 can depend on the length of time that the second HDR template 726 remains viable in the cell and on the concentration of the additional polynucleotide 802 in the cell. The length of time that the second HDR template 726 remains viable in the cell can be based on certain conditions of the cell, such as pH, temperature, and the presence or absence of enzymes or proteins that may facilitate the degradation of the second HDR template 726. As one of ordinary skill in the art will appreciate, the conditions and constituents of a cell can be optimized such that the concentration of the additional polynucleotide 802 and the length of time that the second HDR template 726 remains viable in the cell enable the second HDR template 726 to move into proximity with the first subsequence 802(A) and the second subsequence 802(B). Additionally, the sequence of the second homologous template 726 and the environment in which the second homologous template 726 and the additional polynucleotide are located can be designed such that the second homologous template 726 can remain viable in a cell for a length of time to move into proximity with an additional polynucleotide 802 that has undergone a DSB as understood by those of ordinary skill in the art and described in Clement, Jade Q., Sourindra Maiti, and Wilkinson, Miles F., *Localization and Stability of Introns Spliced from the* Pem *Homeobox Gene,* 276 The Journal of Biological Chemistry, 16919-16930 (May 18, 2001) and Hesselberth Jay R., *Lives that introns lead after splicing,* WIREs RNA 2013, 4: 677-691. doi: 10.1002/wrna.1187.

Performing HDR with the second HDR template 726, the first subsequence 802(A) and the second subsequence 802(B) can produce a new double stranded polynucleotide 810. As explained previously with respect to FIG. 1 and FIG. 2, the second HDR template 726 can displace one strand of the first subsequence 802(A) and the second subsequence 802(B) and pair with the other strand of the first subsequence 802(A) and the second subsequence 802(B) through the formation of a D loop and using DNA ligase. Once the second HDR template 726 is used to repair the DSB of a first strand of the additional polynucleotide 802, DNA polymerase can be utilized to produce a number of nucleotides complementary to those of the barcode sequence 616, thus repairing the second strand of the additional polynucleotide 802 at the DSB to produce the new double stranded polynucleotide 810. The new double stranded polynucleotide 810 can include a middle portion 812 that includes at least the barcode sequence 616. In some cases, the middle portion 812 can also include a number of nucleotides corresponding to the first end region 728 and/or the second end region 730. After producing the new double stranded polynucleotide 810, the new double stranded polynucleotide 810 can be sequenced. The sequencing of the new double stranded polynucleotide 810 can reveal the barcode sequence 616 in the middle portion 812 of the new double stranded polynucleotide 810 indicating the expression of the gene 602.

Figure 9:
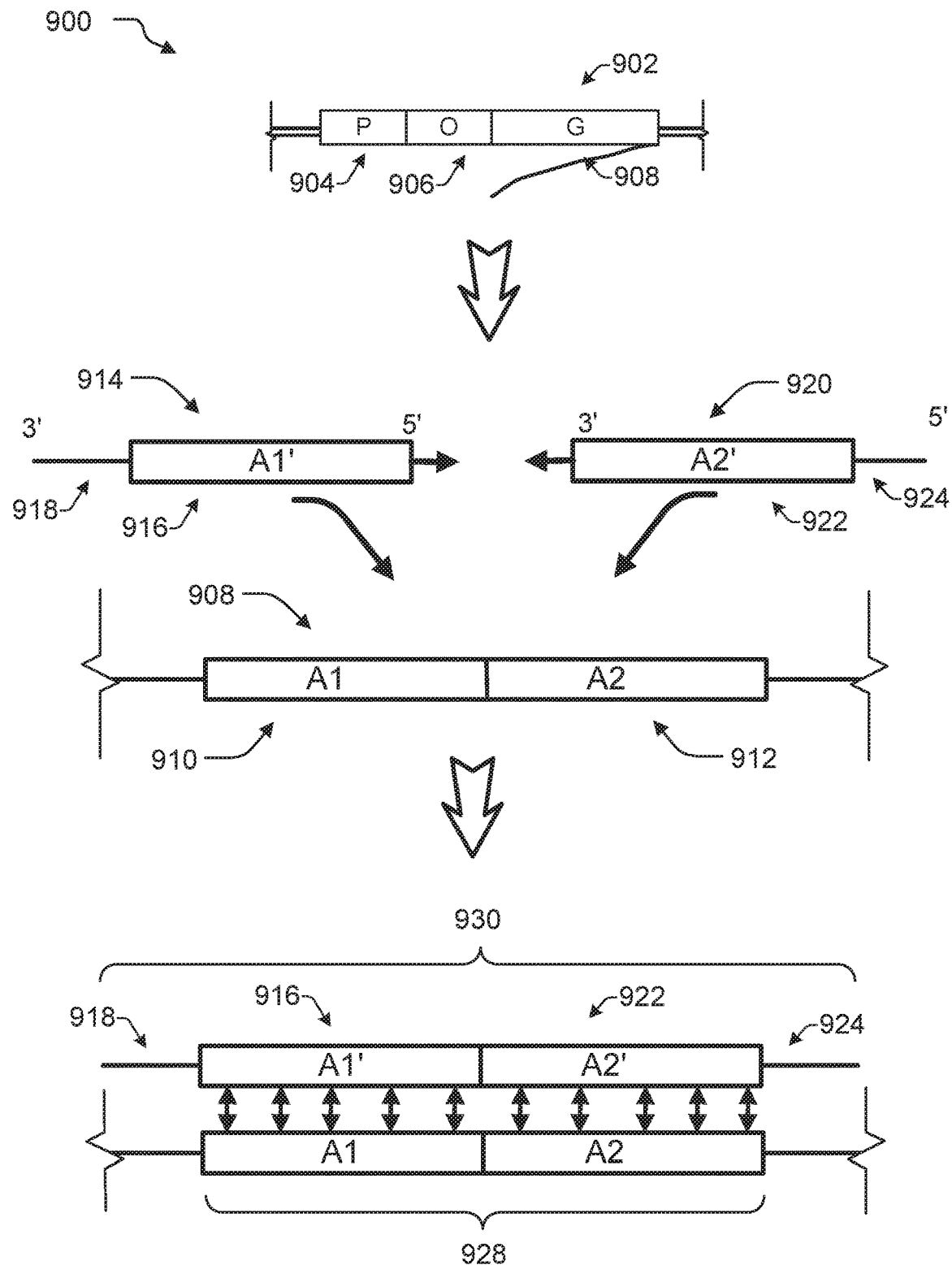
FIG. 9 shows a diagram illustrating joining a first HDR template and a second HDR template to produce a third HDR template using an RNA substrate.

FIG. 9 shows a diagram 900 illustrating joining a first HDR template and a second HDR template to produce a third HDR template using an RNA substrate. In particular, a gene 902 can be under the control of a promoter 904 and an operator 906. As explained previously with respect to FIG. 3, the promoter 904 can be used to implement the expression of the gene 902 and the operator 906 can turn off the expression of the gene 902. The operator 906 can be deactivated and the promoter 904 can be activated using a signaling pathway that is activated in response to a stimulus. The stimulus can include one or more of the presence of a molecule, such as a protein or enzyme, the absence of a molecule, or a condition to which the gene 902 is exposed. In some cases, the gene 902 can be exposed to a condition that affects the activation of the promoter 904 and/or the operator 906, such as a temperature range, a pH range, exposure to a range of electromagnetic radiation, and the like.

In response to being activated, the gene 902 can produce a gene product. In the illustrative example of FIG. 9, the gene product is an mRNA strand 908. The mRNA strand 908 can include a first portion 910, labeled as 'A1' in FIG. 9, and a second portion 912, labeled as 'A2' in FIG. 9. Additionally, a first HDR template 914 can be provided that includes a first region 916 that is homologous to the first portion 910 of the mRNA strand 908. The first region 916 of the first HDR template 914 is labeled "A1'" in FIG. 9. The first region 916 of the first HDR template 914 can have from 5 nucleotides to 75 nucleotides, from 10 nucleotides to 40 nucleotides, or from 20 nucleotides to 50 nucleotides. The first HDR template 914 can also include a remainder region 918. The remainder region 918 of the first HDR template 914 can have from 10 nucleotides to 40 nucleotides. In addition, the remainder region 918 can include a section that can be used in an HDR process. That is, in some cases, at least a portion of the remainder region 918 can be homologous to a target site of a polynucleotide utilized in HDR.

Further, a second HDR template 920 can be provided that includes a first region 922 that is homologous to the second portion 912 of the mRNA strand 908. The first region 922 of the of the second HDR template 920 is labeled as "A2'" in FIG. 9. The first region 922 of the second HDR template 920 can have from 5 nucleotides to 75 nucleotides, from 10 nucleotides to 40 nucleotides, or from 20 nucleotides to 50 nucleotides. The second HDR template 920 can also include a remainder region 924. The remainder region 924 of the second HDR template 920 can have from 10 nucleotides to 40 nucleotides. In addition, the remainder region 924 can include a section that can be used in an HDR process. That is, in some cases, at least a portion of the remainder region 924 can be homologous to a target site of a polynucleotide utilized in HDR. In some particular implementations, at least one of the first remainder region 918 or the second remainder region 924 can include a target region that can serve as an insertion site for an HDR operation.

In the illustrative example of FIG. 9, the first HDR template 914 can move to be proximate to the first portion 910 of the mRNA strand 908 and the second HDR template 920 can move to be proximate to the second portion 912 of the mRNA strand 908. Additionally, a 5' end of the first HDR template 914 can move to be proximate to a 3' end of the second HDR template 920. As the first region 916 of the first HDR template 914 becomes close enough to the first portion 910 of the mRNA strand 908, the first region 916 can anneal to the first portion 910. Also, as the first region 922 of the second HDR template 920 becomes close enough to the first portion 912 of the mRNA strand 908, the first region 922 can anneal to the first portion 912. Further, the 5' end of the first HDR template 914 can be joined to the 3' end of the second HDR template 920. In particular implementations, a ligase can be utilized to join the 5' end of first HDR template 914 with the 3' end of the second HDR template 920. Thus, a modified mRNA strand 918 can be produced that includes a double stranded region 928. Further, joining the 5' end of the first HDR template 914 to the 3' end of the second HDR template 920 can produce a third HDR template 930. The third HDR template 930 can include the first region 916 and the remainder region 918 of the first HDR template 914 and the first region 922 and the remainder region 924 of the second HDR template 920.

Figure 10:
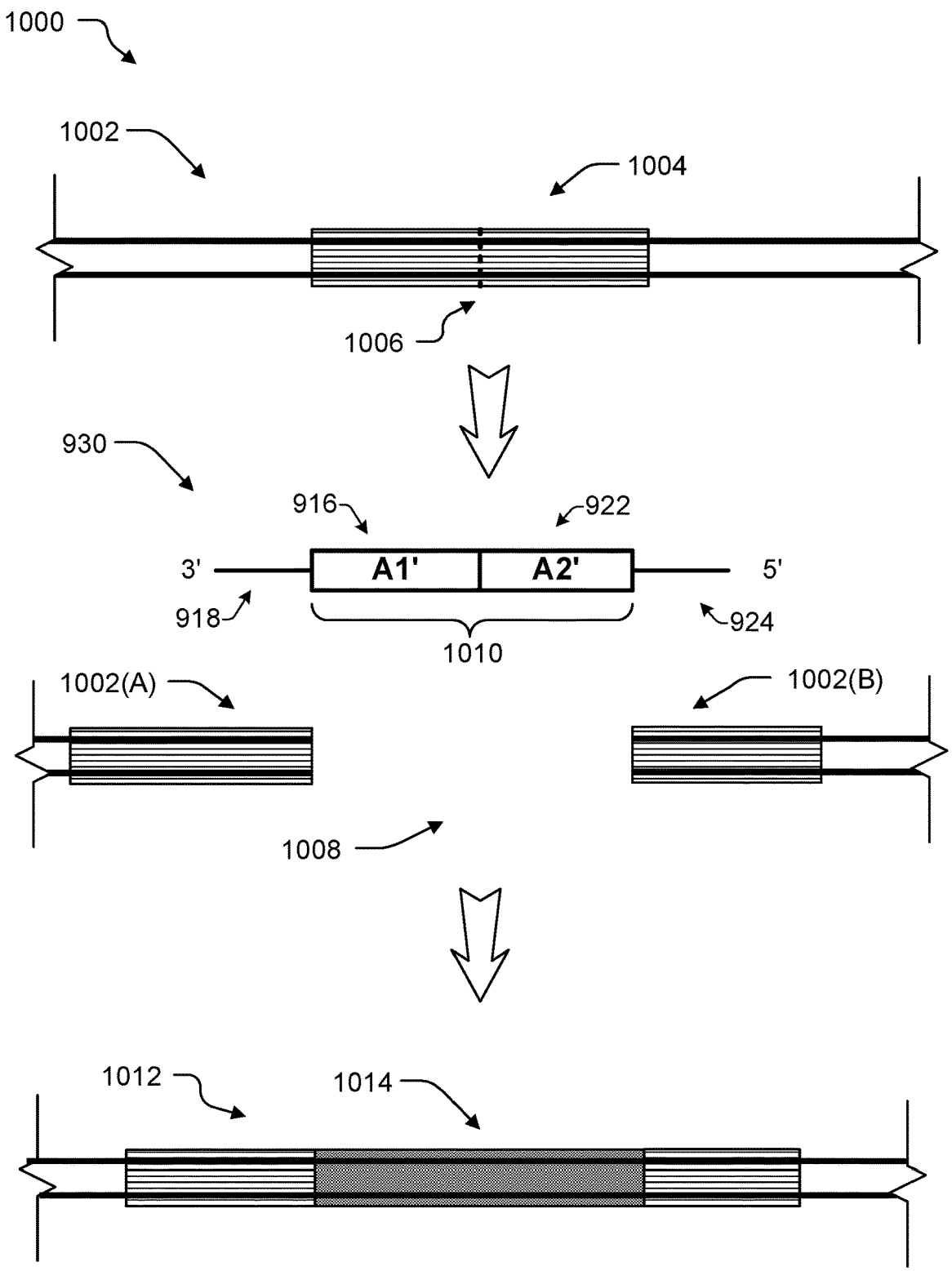
FIG. 10 shows a diagram illustrating insertion of a portion of the third HDR template into an additional polynucleotide.

FIG. 10 shows a diagram 1000 illustrating insertion of a portion of the third HDR template 930 into an additional polynucleotide 1002. The additional polynucleotide 1002 can be dsDNA. In some cases, the additional polynucleotide 1002 can include genomic DNA inside a living prokaryotic or eukaryotic cell. In other situations, the additional polynucleotide 1002 can include dsDNA introduced into a living cell, such as a plasmid or vector. In still other examples, the additional polynucleotide 1002 can include dsDNA in a cell-free system. The additional polynucleotide 1002 can include linear or circular dsDNA prior to undergoing an HDR operation.

The additional polynucleotide 1002 can include a target site 1004. The target site 1004 can include a sequence of nucleotides that can direct an enzyme (not shown) to create a DSB in the additional polynucleotide 1002 within the target site 1004 at a cut site 1006. The target site 1004 can, in some cases, be part of a pre-existing sequence of nucleotides that is recognized by one or more enzymes to create the DSB. In other situations, the target site 1004 can be added to the additional polynucleotide 1002 by conventional genetic engineering techniques such that the DSB can be produced by one or more enzymes. Additionally, the additional polynucleotide 1002 can include a single target site 1004 in some implementations, while in other cases (not shown), the additional polynucleotide 1002 can include multiple target sites 1004. The enzyme used to create the DSB can include enzymes described previously in this application, such as restriction enzymes, homing endonucleases, zinc-finger nucleases, transcription activator-like effector nucleases, CRISPR/Cas, and NgAgo.

The DSB produced by the enzyme in the target site 1004 produces a gap 1008 and two subsequences 1002(A) and 1002(B) on either side of the gap 1008. In various implementations, the target site 1004 can include from about 10 nucleotides to about 40 nucleotides with each of the subsequences 1002(A) and 1002(B) having from about 5 nucleotides to about 20 nucleotides depending on the location of the cut site 1006 within the target site 1004. In some examples, the cut site 1006 can be located in a middle portion of the target site 1004. Alternatively, the cut site 1006 can be included closer to the 3'-end of the target site 1004 or closer to the 5'-end of the target site 1004. The subsequences 1002(A) and 1002(B) can include the same sequences of nucleotides in particular implementations, but different sequences of nucleotides in additional implementations.

After the gap 1008 is created by the DSB, the third HDR template 930 moves into proximity with the subsequences 1002(A) and 1002(B) and the gap 1008. As described previously in this application, the third HDR template 930 can be a polynucleotide sequence that is used to repair the DSB through homologous directed repair. The remainder region 918 can be complementary to the first subsequence 1002(A) and the remainder region 922 can be complementary to the second subsequence 1002(B). The remainder region 918 and the remainder region 922 can also have a length that is similar to or the same as the lengths of the first subsequence 1002(A) and the second subsequence 1002(B). Between the remainder region 918 and the remainder region 922, the third HDR template 922 includes a barcode region 1010 that includes a sequence of nucleotides that corresponds to the gene 902. In some cases, the barcode region 1010 can uniquely identify the gene 902. The barcode region 1010 can be comprised of the first region 916 of the first HDR template 914 and the first region 922 of the second HDR template 920.

As the third HDR template 930 moves into proximity with the first subsequence 1002(A) and the second subsequence 1002(B), HDR can be used to repair the DSB. In some cases, uptake of the third HDR template 930 by the additional polynucleotide 1002 can depend on the length of time that the third HDR template 930 remains viable in the cell and on the concentration of the additional polynucleotide 1002 in the cell. The length of time that the third HDR template 930 remains viable in the cell can be based on certain conditions of the cell, such as pH, temperature, and the presence or absence of enzymes or proteins that may facilitate the degradation of the third HDR template 930. As one of ordinary skill in the art will appreciate, the conditions and constituents of a cell can be optimized such that the concentration of the additional polynucleotide 1002 and the length of time that the third HDR template 930 remains viable in the cell enable the third HDR template 930 to move into proximity with the first subsequence 1002(A) and the second subsequence 1002(B). Additionally, the sequence of the third HDR template 930 and the environment in which the third HDR template 930 and the additional polynucleotide 1002 are located can be designed such that the third HDR template 930 can remain viable in a cell for a length of time to move into proximity with an additional polynucleotide 1002 that has undergone a DSB as understood by those of ordinary skill in the art and described in Clement, Jade Q., Sourindra Maiti, and Wilkinson, Miles F., *Localization and Stability of Introns Spliced from the* Pem *Homeobox Gene*, 276 The Journal of Biological Chemistry, 16919-16930 (May 18, 2001) and Hesselberth Jay R., *Lives that introns lead after splicing*, WIREs RNA 2013, 4: 677-691. doi: 10.1002/wrna.1187.

Performing HDR with the third HDR template 930, the first subsequence 1002(A) and the second subsequence 1002(B) can produce a new double stranded polynucleotide 1012. As explained previously with respect to FIG. 1 and FIG. 2, the third HDR template 930 can displace one strand of the first subsequence 1002(A) and the second subsequence 1002(B) and pair with the other strand of the first subsequence 1002(A) and the second subsequence 1002(B) through the formation of a D loop and using DNA ligase. Once the third HDR template 930 is used to repair the DSB of a first strand of the additional polynucleotide 1002, DNA polymerase can be utilized to produce a number of nucleotides complementary to those of the barcode sequence 928, thus repairing the second strand of the additional polynucleotide 1002 at the DSB to produce the new double stranded polynucleotide 1012. The new double stranded polynucleotide 1012 can include a middle portion 1014 that includes at least the barcode sequence 928. In some cases, the middle portion 1014 can also include a number of nucleotides corresponding to the remainder region 918 and/or the remainder region 924. After producing the new double stranded polynucleotide 1012, the new double stranded polynucleotide 1012 can be sequenced. The sequencing of the new double stranded polynucleotide 1012 can reveal the barcode sequence 928 in the middle portion 1014 of the new double stranded polynucleotide 1012 indicating the expression of the gene 902.

Although not shown in the illustrative example of FIG. 10, the third HDR template 930 can still be joined to the first portion 910 and the second portion 912 of the RNA strand 908 as the third HDR template 930 begins to join with portions of the first subsequence 1002(A) and the second subsequence 1002(B). In some cases, the third HDR template 930 can be separated from the RNA strand 908 as the remainder region 918 and the remainder region 924 begin to join with the first subsequence 1002(A) and the second subsequence 1002(B), respectively. In other situations, the third HDR template 930 can be separated from the RNA strand 908 during translation of the RNA strand. In particular instances, the third HDR template 930 can be removed from the RNA strand 908 before the HDR process begins. In still other implementations, the third HDR template 930 can be separated from the RNA strand 908 as a polymerase produces the second strand of the double stranded polynucleotide 1012 that is complementary to the barcode region 1010 of the third HDR template 930.

Illustrative Processes

For ease of understanding, the processes discussed in this disclosure are delineated as separate operations represented as independent blocks. However, these separately delineated operations should not be construed as necessarily order dependent in their performance. The order in which a process is described is not intended to be construed as a limitation, and any number of the described process blocks may be combined in any order to implement the process, or an alternate process. Moreover, it is also possible that one or more of the provided operations may be modified or omitted.

Figure 11:
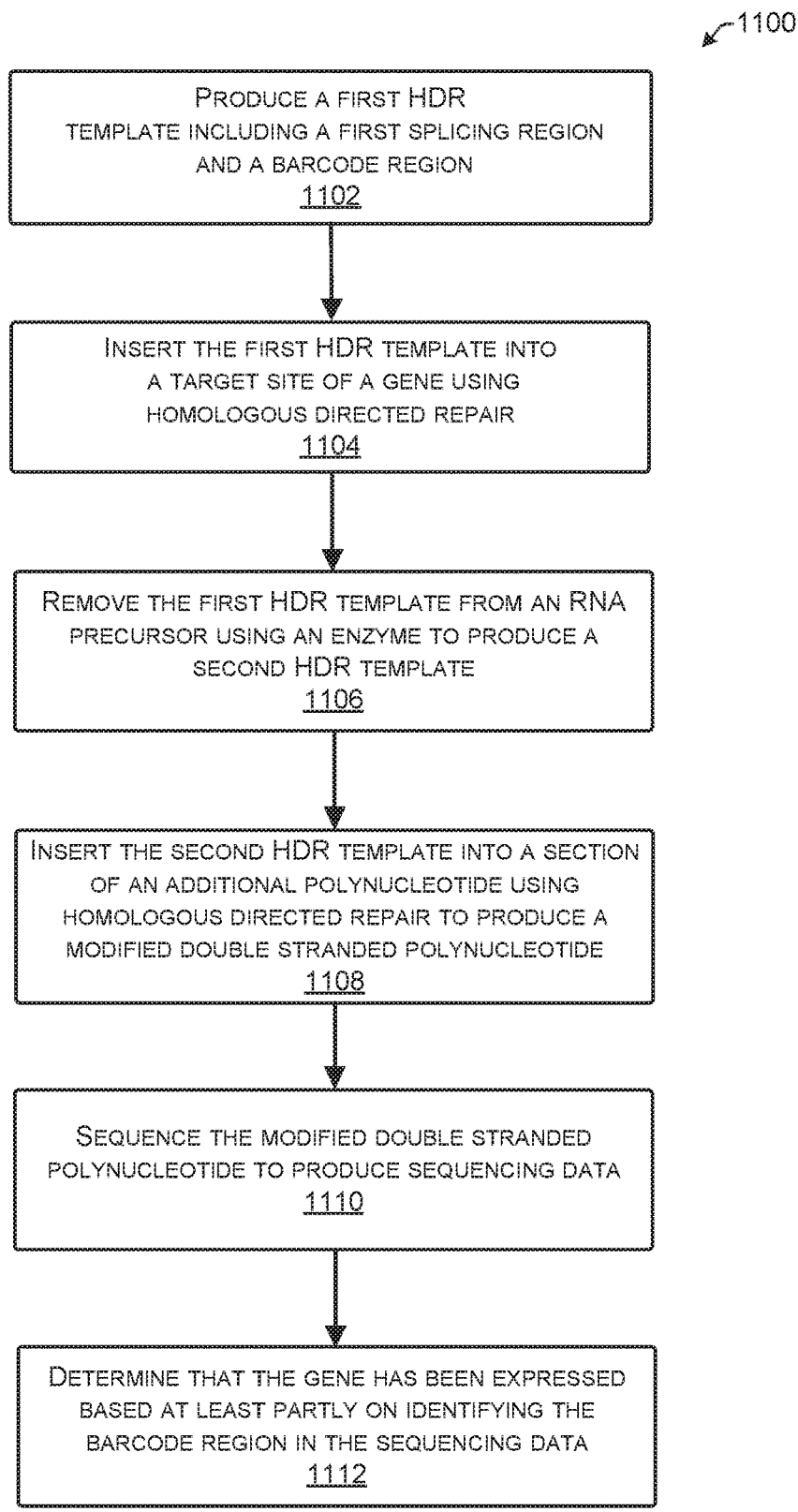
FIG. 11 shows an illustrative process for identifying the expression of a gene by sequencing DNA that includes a barcode sequence corresponding to the gene.

FIG. 11 shows an illustrative process 1100 for identifying the expression of a gene by sequencing DNA that includes a barcode sequence corresponding to the gene.

At 1102, the process 1100 includes producing a first HDR template including a first splicing region and a barcode region. The barcode region can include a nucleotide sequence that corresponds to the gene. For example, the sequence of the barcode can be used to specifically identify the gene. That is, identifying the presence of the barcode sequence in a polynucleotide can provide an indication of the expression of the gene. In some cases, the gene can be one of a plurality of genes and individual barcode sequences can be produced that correspond to the individual genes.

In particular implementations, data can be generated by one or more algorithms implemented by a computing device that indicates a number of barcode sequences and individual barcode sequences can be arbitrarily associated with each gene. The one or more algorithms can take into consideration one or more criteria in order to generate the barcode sequences. To illustrate, the barcode sequences can be generated based on a particular range of lengths for the barcode sequences, such as from 50 nucleotides to 500 nucleotides, from 50 nucleotides to 250 nucleotides, or from 100 nucleotides to 200 nucleotides. In another illustrative example, the barcode sequences can be generated based on the stability of the barcode sequence within an environment. In certain situations, the environment can include a cell subjected to a set of conditions, such as a temperature range, a pH, and the like. In various implementations, the barcode sequences can be generated based on stability of the barcode sequence in a polynucleotide that also includes other sequences, such as one or more splicing regions, in an environment. The barcode sequences can also be generated with consideration of their behavior as single-stranded polynucleotides such the ability to form secondary structures like hairpin loops.

Additionally, the splicing region can include a sequence of nucleotides that is recognized by an enzyme to produce a cut in the splicing region. The enzyme can include a spliceosome that can identify a configuration of nucleotides and produce a cut at a specific location within the splicing region. The sequence of nucleotides for the splicing region can be generated by one or more computer-implemented algorithms. The one or more computer-implemented algorithms can take into consideration information known by one of ordinary skill in the art regarding sequences that are recognized by a number of spliceosomes and utilize the information to generate the sequence of the splicing region. For example, information known to those of ordinary skill in the art can indicate that a particular location of a splicing region can include any purine, and the one or more algorithms can be implemented to include adenine or guanine at the particular location. In another example, the one or more algorithms may not be flexible in determining a nucleotide at a location of a splicing sequence where the information known to those skilled in the art indicates that an adenine is to be present at the location.

In some cases, the first HDR template can include multiple splicing regions. In situations where the first HDR template is located at an end of the gene, such as the 3' UTR, a single splicing region can be included in the first HDR template because a cut at the splicing region can be sufficient to free the first HDR template from a product produced from the gene, such as an mRNA precursor. In other situations, the first HDR template can be located within a coding portion of the gene. In these situations, the first HDR template can include multiple splicing regions. Each of the splicing regions can include a sequence of nucleotides known to those skilled in the art to be recognized by a spliceosome to produce a cut at each of the splicing regions. In particular implementations, the first HDR template can be inserted into the gene as an intron. In an illustrative example, the first HDR template can include two splicing regions with the barcode region located between the splicing regions.

At 1104, the process 1100 includes inserting the first HDR template into a target site of a gene using homologous directed repair. In particular, an enzyme, such as a nuclease can be utilized to create a DSB in a target site of the gene. At least a portion of the splicing region or regions can be homologous to a corresponding portion of the gene at the cut site. In some implementations, a portion of the barcode sequence can be homologous to a corresponding portion of the gene at the cut site. In implementations where the first HDR template includes a barcode region located between two splicing regions, at least a portion of a first splicing region can be homologous to a first portion of a target site of the gene located on a first side of the DSB and at least a portion of the second splicing region can be homologous to a second portion of the target site located on a second side of the DSB that is situated opposite the DSB to the first side. Homology directed repair can be used to insert the first HDR template into the target site of the gene.

In various implementations, the target site of the gene can be a region that is naturally occurring in the gene. In other implementations, the target site can be inserted into the gene through HDR. That is, a HDR template that includes a sequence of the target site can be inserted into the gene before the first HDR template including the barcode region is inserted into the gene.

At 1106, the process 1100 includes removing the first HDR template from an RNA precursor using an enzyme to produce a second HDR template. In particular implementations, expression of the gene can take place in response to one or more signals. The one or more signals can be related to an environment of gene. For example, the one or more signals can be related to a temperature, a pH, the presence of a protein, the presence of an enzyme, or combinations thereof. As the gene is expressed, an RNA precursor can be formed before RNA, such as mRNA, is produced that can be utilized to form a protein or other product encoded by the gene. The RNA precursor can include a 5' UTR, a 3' UTR, and a coding region that includes introns and exons. The introns and the first HDR template can be removed from the RNA precursor by spliceosomes that recognize splicing sequences within the RNA precursor and make cuts within the various splicing sequences.

The action of an enzyme to cut the first HDR template at the first splicing region can produce the second HDR template, which includes the barcode region and at least a portion of the first splicing region since some amount of the first splicing region can be left behind after the cut made by the enzyme. Additionally, when the first HDR template includes a second splicing region, the second HDR template can include at least a portion of the second splicing region.

The sequence of the second HDR template can be designed such that the second HDR template remains viable in the environment for a specified period of time. In some implementations, the sequence of the second homologous template can be designed using one or more algorithms implemented by a computing device and relying on knowledge available to one of ordinary skill in the art. For example, the one or more algorithms can utilize knowledge of one of ordinary skill in the art regarding the viability of introns in certain environments and generate a sequence for the second homologous template that is likely to remain viable in an environment for the specified period of time.

At 1108, the process 1100 includes inserting the second HDR template into a section of an additional polynucleotide using homology directed repair to produce a modified double stranded polynucleotide. The second HDR template can be inserted into a section of the additional polynucleotide by bringing the second HDR template in contact with the additional polynucleotide. The section of the additional polynucleotide that the second HDR template is inserted into can be a target site that includes a cut site. A DSB can be created at the cut site using an enzyme, such as a nuclease. The additional double stranded polynucleotide can include genomic DNA or artificial DNA. Also, in some cases, the additional double stranded polynucleotide can include linear DNA or circular DNA before the insertion of the second HDR template into the target site.

In particular implementations, the second HDR template can include a first portion that is homologous to a first section of the target site of the additional double stranded polynucleotide that is on one side of the DSB and a second portion that is homologous to a second section of the target site that is on the other side of the DSB. In some cases, the first portion of the second HDR template can include at least part of the first splicing region. In various implementations, the first portion of the second HDR template can also include a portion of the sequence of the barcode region. In situations where the second HDR template is formed using only a single splicing region, the second portion of the second HDR template can be comprised of a portion of the sequence of the barcode region. In examples where the second HDR template is formed using two splicing regions, the second portion of the second HDR template can be comprised of a portion of a second splicing region. Additionally, in some cases where the second HDR template is formed using two splicing regions, the second portion of the second HDR template can be comprised of a portion of the second splicing region and a portion of the barcode region.

In some cases, the additional double stranded polynucleotide can include multiple target sites. A first target site can be utilized to insert the second HDR template into the additional double stranded polynucleotide. Additionally, a second target site can be utilized to insert sequences corresponding to other indicators into the additional double stranded polynucleotide. For example, a second target site can be utilized to insert a timing indicator into the additional double stranded polynucleotide. To illustrate, a signal associated with a particular time can be generated and cause an enzyme to create a DSB at the second target site. Also, a HDR template that corresponds to the timing event can be brought into contact with the second target site and be inserted into the additional double stranded polynucleotide using HDR. In this way, a timing related to the insertion of the second homologous template into the additional double stranded polynucleotide can be recorded in the additional double stranded polynucleotide. The insertion of timing indicators into the additional double stranded polynucleotide can be performed according to the techniques described in Applicant's patent application entitled "Timing of Logged Molecular Events" and which is incorporated by reference herein in its entirety.

At 1110, the process 1100 includes sequencing the modified double stranded polynucleotide to produce sequencing data. The sequencing of the modified double stranded polynucleotide can be performed by any polynucleotide sequencing technique known to those of skill in the art. The sequencing data can include information indicating the nucleotides present at the various positions of the modified double stranded polynucleotide.

At 1112, the process 1100 includes determining that the gene has been expressed based at least partly on identifying the barcode sequence in the sequencing data. In particular, the sequencing data can be compared with a record of the barcode sequence. In response to determining that the modified double stranded polynucleotide includes the barcode sequence or includes substantially all of the barcode sequence based on the comparison, the expression of the gene can be identified. This is because insertion of the barcode sequence into the additional double stranded polynucleotide occurs a result of the expression of the gene through the gene expression making the second HDR template including the barcode sequence available to be added to the additional double stranded polynucleotide.

Figure 12:
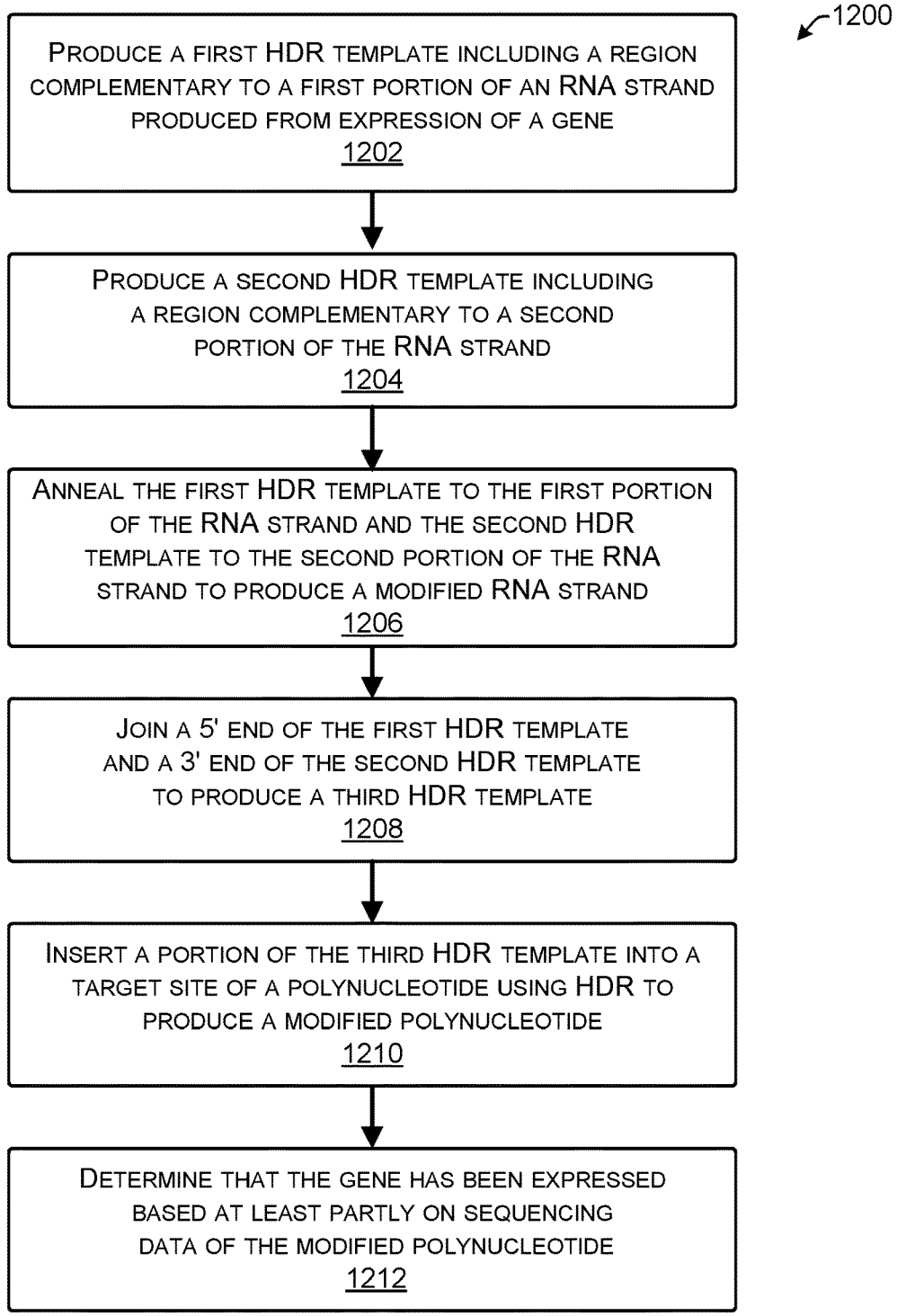
FIG. 12 shows an additional illustrative process for identifying the expression of a gene by sequencing DNA that includes a barcode sequence corresponding to the gene

FIG. 12 shows an additional illustrative process 1200 for identifying the expression of a gene by sequencing DNA that includes a barcode sequence corresponding to the gene.

At 1202, the process 1200 includes producing a first HDR template including a region complementary to a first portion an RNA strand produced from the expression of the gene. In some cases, the RNA can include mRNA that is produced during the expression of the gene. The first HDR template can include a portion that is a first part of a barcode sequence that can be utilized to identify the gene. The first part of the barcode sequence can correspond to a section of the first HDR template that is complementary to a first portion of the RNA strand. In this way, the portion of the first HDR template corresponding to the first part of the barcode sequence can joined to the first portion of the RNA strand. Additionally, the first HDR template can include other useful sequences. For example, the first HDR template can include a target region that can be utilized as an insertion region in an HDR operation. Further, the first HDR template can include a region that is homologous to a portion of an insertion site of a polynucleotide that is utilized in an HDR process.

At 1204, the process 1200 can produce a second HDR template including a region complementary to a second portion of the RNA strand. The second HDR template can include a portion that is a second part of a barcode sequence that can be utilized to identify the gene. The second part of the barcode sequence can be a section of the second HDR template that is complementary to a second portion of the RNA strand. In this way, the portion of the second HDR template corresponding to the second part of the barcode sequence can joined to the second portion of the RNA strand. Additionally, the second HDR template can include other useful sequences. For example, the second HDR template can include a target region that can be utilized as an insertion region in an HDR operation. Further, the second HDR template can include a region that is homologous to a portion of an insertion site of a polynucleotide that is utilized in an HDR process.

At 1206, the process 1200 includes annealing the first HDR template to the first portion of the RNA strand and the second HDR template to the second portion of the RNA strand to produce a modified RNA strand. In particular, the section of the first HDR template complementary to the first portion of the RNA strand can be annealed, while the section of the second HDR template complementary to the second portion of the RNA strand can be annealed.

At 1208, the process 1200 includes joining a 5' end of the first HDR template to a 3' end of the second HDR template to produce a third HDR template. In various implementations, the first portion of the RNA strand and the second portion of the RNA strand can be adjacent to each other. Accordingly, when a section of the first HDR template and a section of the second HDR template are annealed to respective portions of the RNA strand, the 5' end of the first HDR template and the 3' end of the second HDR template can be proximate to one another. A ligase can then be utilized to join the 5' end of the first HDR template and the 3' end of the second HDR template. In some cases, an RNA ligase can be utilized, while in other situations, a DNA ligase can be utilized. In some illustrative examples, a ligase used to join the 5' end of the first HDR template to the 3' end of the second HDR template can include a T4 RNA ligase, such as T4 RNA Ligase 1 or T4 RNA Ligase 2, *Deinoccus radiodurans* RNA ligase, bacteriophage T4 DNA ligase.

At 1210, the process 1200 includes inserting a portion of the third HDR template into a target site of a polynucleotide using homology directed repair to produce a modified double stranded polynucleotide. The portion of the third HDR template can be inserted into a section of the polynucleotide by bringing the third HDR template in contact with the polynucleotide. In particular, the portions of the third HDR template that are complementary to target site of the polynucleotide can be contacted. The section of the polynucleotide that the third HDR template is inserted into can be a target site that includes a cut site. A DSB can be created at the cut site using an enzyme, such as a nuclease. The polynucleotide can include genomic DNA or artificial DNA. Also, in some cases, the polynucleotide can include linear DNA or circular DNA before the insertion of the third HDR template into the target site.

In particular implementations, to design the sequence of the third HDR template, RNA sequences produced during the translation of a particular gene can be analyzed and certain regions of the mRNA can be determined that uniquely identify the gene. A portion of an mRNA sequence that uniquely identifies the gene can be from 10 nucleotides to 120 nucleotides, from 20 nucleotides to 100 nucleotides, or 25 nucleotides to 80 nucleotides. The first HDR template and the second HDR template can be designed such that a portion of the first HDR template is complementary to a first part of the unique RNA sequence and a portion of the second HDR template is complementary to a second part of the unique RNA sequence. In this way, when joined in the third HDR template, a portion of the first HDR template and a portion of the second HDR template can comprise a complete barcode sequence that identifies RNA that is produced during expression of the gene.

Further, an additional portion of the first HDR template can be designed to be complementary to a first portion of an insertion site of a polynucleotide and an additional portion of the second HDR template can be designed to be complementary to a second portion of an insertion site of the polynucleotide. In this way, the portions of the first HDR template and the second HDR template that are complementary to the insertion site can be joined to the polynucleotide, which enables the barcode sequence to be inserted into the polynucleotide at the insertion site using HDR.

The first HDR template, the second HDR template, and the third HDR template can also be designed with respect to their viability in an environment. In certain situations, the environment can include a cell subjected to a set of conditions, such as a temperature range, a pH, and the like. Additionally, the first HDR template, the second HDR template, and the third HDR template can be designed with respect to the strength of the attachment to the RNA strand and the polynucleotide utilized in the HDR operation. In this way, the third HDR template can be separated from the RNA strand after portions of the first HDR template and the second HDR template that are complementary to the target site of the polynucleotide are joined to the polynucleotide.

In an illustrative example, the RNA strand can be mRNA having a sequence -A1-A2-A3-A4-, where A1 and A4 can be sequences of hundreds or thousands of nucleotides and A2 and A3 are sequences that include from 10 nt to 40 nt. A2 and A3 can together comprise a barcode sequence for a gene that produces the mRNA during expression. Additionally, the first HDR template can have a sequence X-A2' and the second HDR template can have a sequence A3'-YY-X with the third HDR template having the sequence X-A2'-A3'-YY-X. In this example, X is a sequence that is complementary to a portion of an insertion site on a polynucleotide in which the barcode sequence can be inserted. Also, YY is a sequence that can provide an additional insertion site once the third HDR template is inserted into the polynucleotide.

At 1212, the process 1200 includes determining that the gene has been expressed based at least partly on sequencing data of the modified polynucleotide. In particular, the modified polynucleotide can be sequenced to produce sequencing data and the sequencing data can be analyzed. That is, the sequencing data can be compared to the barcode sequence and, upon determining that a portion of the sequence data corresponds to the barcode sequence, a determination can be made that the gene has been expressed. This is because insertion of the barcode sequence into the polynucleotide occurs a result of the production of the RNA strand that binds the third HDR template during the expression of the gene.

Furthermore, although the process 1200 has been described with respect to ligation of the 5' end of the first HDR template and the 3' end of the second HDR template to produce the third HDR template for subsequent insertion into the target site of the polynucleotide, other methods can be utilized to produce the third HDR template. For example, the RNA strand can enable the first HDR template and the second HDR template to serve as sequence and ligation independent cloning (SLIC) templates during insertion of the barcode sequence into the polynucleotide.

Illustrative System and Computing Devices

Figure 13:
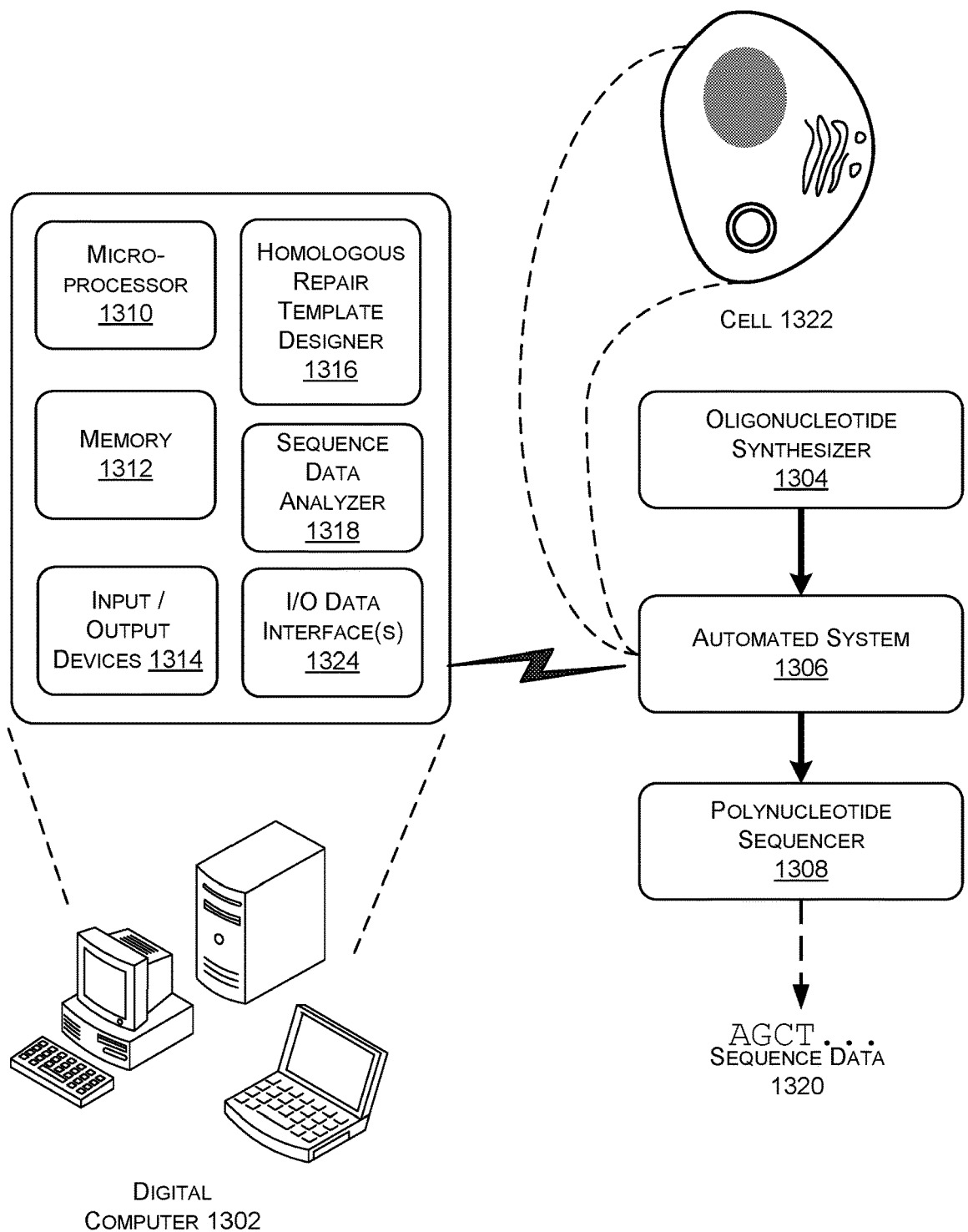
FIG. 13 shows a system for designing barcode sequences and utilizing the barcode sequences to identify the expression of a gene.

FIG. 13 shows a system 1300 for designing barcode sequences and utilizing the barcode sequences to identify the expression of a gene. The architecture may include any of a digital computer 1302, an oligonucleotide synthesizer 1304, an automated system 1306, and/or a polynucleotide sequencer 1308. The architecture 1300 may also include other components besides those discussed herein.

As used herein, "digital computer" means a computing device including at least one hardware microprocessor 1310 and memory 1312 capable of storing information in a binary format. The digital computer 1302 may be a supercomputer, a server, a desktop computer, a notebook computer, a tablet computer, a game console, a mobile computer, a smartphone, or the like. The hardware microprocessor 1310 may be implemented in any suitable type of processor such as a single core processor, a multicore processor, a central processing unit (CPU), a graphical processing unit (GPU), or the like. The memory 1312 may include removable storage, non-removable storage, local storage, and/or remote storage to provide storage of computer readable instructions, data structures, program modules, and other data. The memory 1312 may be implemented as computer-readable media. Computer-readable media includes, at least, two types of media, namely computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer readable instructions, data structures, program modules, or other data in a modulated data signal, such as a carrier wave, or other transmission mechanism. As defined herein, computer-readable storage media and communications media are mutually exclusive.

The digital computer 1302 may also include one or more input/output devices(s) 1314 such as a keyboard, a pointing device, a touchscreen, a microphone, a camera, a display, a speaker, a printer, and the like.

An HDR template designer 1316 may be included as part of the digital computer 1302, for example, as instructions stored in the memory 1312. The HDR template designer 1316 may design HDR templates based on sequences of target sites, sequences of dsDNA molecules, enzyme recognition sites, etc. In one implementation, the HDR template designer 1316 may design HDR templates to avoid cross talk between different signal recording pathways. The HDR template designer 1316 may also compare percent similarity and hybridization conditions for potential HDR templates as well as portions of the HDR templates. For example, the HDR template designer 1316 may design HDR templates to avoid the formation of hairpins as well as to prevent or minimize annealing between HDR templates. The HDR template designer 1316 may also design HDR templates to maximize a difference between the 3'-end sequence, 5'-end sequence, and/or middle sequence. For example, the difference may be G: C content and the HDR template designer 1316 may design sequences with a preference for increasing the G:C content difference between the end sequences and the middle sequence. The HDR template designer 1316 can also generate barcode sequences and splicing sequences to include in HDR templates. In some cases, a table indicating the individual barcode sequences that correspond to each gene can be stored in the memory 1312 and utilized to determine that a gene has been expressed after analyzing the sequence data 1320.

A sequence data analyzer 1318 may analyze sequence data 1320 generated by the polynucleotide sequencer 1308. The sequence data analyzer 1318 may be implemented as instructions stored in the memory 1312. Thus, sequence data 1320 may be provided to the sequence data analyzer 1318 which analyzes the sequence data 1320 to identify any barcode sequences included in the sequence data. The sequence data analyzer 1318 may also identify which signals were detected by a cell 1322 and may identify timing indicators or barcode sequences included in the DNA of the cell 1322. Depending on the design of the cell 1322, the sequence data analyzer 1318 may also identify a signal strength, relative signal strength, order of different signals, signal duration, timing of signals, or other characteristic of one or more signals represented in the sequence data 1320. As used herein, "cell" includes biological cells, minimal cells, artificial cells, and synthetic cells.

In order to manipulate the DNA and potentially RNA that makes up the HDR templates and dsDNA, the digital computer 1302 may communicate with other devices through one or more I/O data interfaces 1324. The I/O data interface(s) 1324 can exchange instructions and data with other devices such as the oligonucleotide synthesizer 1304, the automated system 1306, and the polynucleotide sequencer 1308.

The oligonucleotide synthesizer 1304 chemically synthesizes oligonucleotides based on instructions received as electronic data. The synthesized oligonucleotides may be used as HDR templates, as dsDNA molecules that provide target sites, as plasmids, vectors, or other components. Thus, in some implementations, the sequence of nucleotides which is provided to the oligonucleotide synthesizer 1304 may come from the HDR template designer 1316.

A number of methods for DNA synthesis and commercial oligonucleotide synthesizers are available. Methods for DNA synthesis include solid-phase phosphoramidite synthesis, microchip-based oligonucleotide synthesis, ligation-mediated assembly, PCR-mediated assembly, and the like. For example, such synthesis can be performed using an ABI 394 DNA Synthesizer (Applied Biosystems, Foster City, Calif.) in 0.2 µmol scale followed by standard cleavage and deprotection protocol, e.g., using 28% aqueous ammonia or a 3:1 solution of ammonia in methanol. One having ordinary skill in the art can select other cleaving agents, such as methylamine, to be used instead of, or in addition to, ammonia, if desired.

The term "oligonucleotide" as used herein is defined as a molecule including two or more nucleotides. Oligonucleotides include probes and primers. Oligonucleotides used as probes or primers may also include nucleotide analogues such as phosphorothioates, alkylphosphorothioates, peptide nucleic acids, or intercalating agents. The introduction of these modifications may be advantageous in order to positively influence characteristics such as hybridization kinetics, reversibility of the hybrid-formation, stability of the oligonucleotide molecules, and the like.

The automated system 1306 may include any type of robotics, automation, or other system for automating one or more manipulations that may be performed on the dsDNA with the enzymes and/or the HDR templates. The automated system 1306 may be used in conjunction with manual operations such that the totality of operations needed to be performed to practice the techniques of this disclosure are done so in a hybrid manner in which some are performed by the automated system 1306 and others manually.

In one implementation, the automated system 1306 may include a microfluidics system. An illustrative microfluidics system may be configured to move small volumes of liquid according to techniques well-understood by those of ordinary skill in the art. As used herein, the automated system 1306 may include other equipment for manipulating DNA beyond that expressly shown in FIG. 13 such as, for example, a thermocycler.

The automated system 1306 may include a cell-free system that can be implemented in part by microfluidics. The cell-free system may also be implemented as an artificial cell or a minimal cell. As used herein the term "cell" encompasses natural cells, artificial cells, and minimal cells unless context clearly indicates otherwise. The automated system 1306 may include one or more natural cells such as a cell in culture. A culture of cells in the automated system 1306 may be manipulated by an automated cell culture system. An artificial cell or minimal cell is an engineered particle that mimics one or many functions of a biological cell. Artificial cells are biological or polymeric membranes which enclose biologically active materials. As such, nanoparticles, liposomes, polymersomes, microcapsules, detergent micelles, and a number of other particles may be considered artificial cells. Micro-encapsulation allows for metabolism within the membrane, exchange of small molecules and prevention of passage of large substances across it. Membranes for artificial cells can be made of simple polymers, crosslinked proteins, lipid membranes or polymer-lipid complexes. Further, membranes can be engineered to present surface proteins such as albumin, antigens, Na/K-ATPase carriers, or pores such as ion channels. Commonly used materials for the production of membranes include hydrogel polymers such as alginate, cellulose and thermoplastic polymers such as hydroxyethyl methacrylate-methyl methacrylate (HEMA-MMA), poly-acrylonitrile-polyvinyl chloride (PAN-PVC), as well as variations of the above-mentioned materials.

Minimal cells, also known as proto-cells, are cells that help all the minimum requirements for life. Minimal cells may be created by a top-down approach that knocks out genes in a single-celled organism until a minimal set of genes necessary for life are identified. *Mycoplasma mycoides, E. coli*, and *Saccharomyces cerevisiae*, are examples of organisms that may be modified to create minimal cells. One of ordinary skill in the art will recognize multiple techniques for generating minimal cells.

The cell-free system includes components for DNA replication and repair such as nucleotides, DNA polymerase, and DNA ligase. The cell-free system will also include dsDNA that includes at least one initial target site for creating a DSB. The dsDNA may be present in the vector that includes one or more operons. The cell-free system will also include buffers to maintain pH and ion availability. Furthermore, the cell-free system may also include the enzymes used for creating DSBs in dsDNA and the HDR templates used for repairing dsDNA. Some cell-free systems may include genes encoding the enzymes and HDR templates. To prevent enzymes from remaining when their respective cutting functions are no longer desired, the cell-free system may include proteolytic enzymes that specifically break down nucleases.

In a cell-free system, particular components may be added when needed either by moving volumes of liquid together with microfluidics or by increasing the expression of gene products that leads to synthesis of enzymes, HDR templates, etc.

The automated system 1306 may include a structure, such as at least one chamber, which holds one or more DNA molecules. The chamber may be implemented as any type of mechanical, biological, or chemical arrangement which holds a volume of liquid, including DNA, to a physical location. For example, a single flat surface having a droplet present thereon, with the droplet held by surface tension of the liquid, even though not fully enclosed within a container, is one implementation of a chamber.

The automated system 1306 may perform many types of manipulations on DNA molecules. For example, the automated system 1306 may be configured to move a volume of liquid from one chamber to another chamber in response to a series of instructions from the I/O data interface 1324.

The polynucleotide sequencer 1308 may sequence DNA molecules using any technique for sequencing polynucleotides known to those skilled in the art including classic dideoxy sequencing reactions (Sanger method), sequencing by synthesis using reversibly terminated labeled nucleotides, pyrosequencing, nanopore sequencing, SOLiD sequencing, chemical-sensitive field effect transistor (chemFET) sequencing, and ion semiconductor sequencing. The polynucleotide sequencer 1308 may be configured to sequence all or part of a dsDNA molecule modified according to any of the techniques described above and provide the sequence data 1320 to the digital computer 1302.

The cell 1322 may be prepared for sequencing by extracting nucleic acids according to standard methods in the art. For example, DNA from a cell can be isolated using various lytic enzymes, chemical solutions, or extracted by nucleic acid binding resins following instructions provided by a manufacturer. DNA contained in extracted sample may be detected by amplification procedures such as PCR or hybridization assays according to methods widely known in the art. Furthermore, RNA can be detected and analyzed using techniques, such as single molecule fluorescent in situ hybridization (smFISH) techniques.

The sequence data 1320 generated by sequencing can be sent from the polynucleotide sequencer 1308 to the digital computer 1302 for analysis by the sequence data analyzer 1318, and also for presentation on an output device 1314.

Illustrative Site-Specific Nucleases

Restriction enzymes (restriction endonucleases) are present in many species and are capable of sequence-specific binding to DNA (at a target or recognition site), and cleaving DNA at or near the site of binding. Over 3000 restriction enzymes have been studied in detail, and more than 600 of these are available commercially. Naturally occurring restriction endonucleases are categorized into four groups (Types I, II III, and IV) based on their composition and enzyme cofactor requirements, the nature of their target site, and the position of their DNA cleavage site relative to the target site. All types of enzymes recognize specific short DNA sequences and carry out the endonucleolytic cleavage of DNA to give specific fragments with terminal 5'-phosphates. One type of restriction enzyme, Type II enzymes, cleave within or at short specific distances from a recognition site; most require magnesium; single function (restriction) enzymes independent of methylase. Type II enzymes form homodimers, with recognition sites that are usually undivided and palindromic and 4-8 nucleotides in length. They recognize and cleave DNA at the same site, and they do not use ATP or AdoMet for their activity—they usually require only $Mg^{2+}$ as a cofactor. Common type II restriction enzymes include HhaI, HindIII, NotI, EcoRI, and BglI. Restriction enzymes may cut dsDNA in a way that leaves either blunt ends or sticky ends. Protocols for creating a DSB in dsDNA with restriction enzymes are well known to those skilled in the art. Restriction digest is a common molecular biology technique and is typically performed using the reagents and protocols provided in a commercially available restriction digest kit. Examples of companies that provide restriction digest kits include New England Bio-Labs, Promega, Sigma-Aldrich, and Thermo Fisher Scientific. Each of these companies provides restriction digest protocols on their website.

Homing endonucleases (HEs), which are also known as meganucleases, are a collection of double-stranded DNases that have large, asymmetric recognition sites (12-40 nt) and coding sequences that are usually embedded in either introns or inteins. Introns are spliced out of precursor RNAs, while inteins are spliced out of precursor proteins. They catalyze the hydrolysis of genomic DNA within the cells that synthesize them, but do so at few, or even a single, location(s) per genome. HE recognition sites are extremely rare. For example, an 18 nt recognition sequence will occur only once in every $7 \times 10^{10}$ nucleotides of random sequence. This is equivalent to only one site in 20 mammalian-sized genomes. However, unlike restriction endonucleases, HEs tolerate some sequence degeneracy within their recognition sequence. Thus, single base changes do not abolish cleavage but reduce its efficiency to variable extents. As a result, their observed sequence specificity is typically in the range of 10-12 nt. Examples of suitable protocols using HEs may be found in Flick, K et al., *DNA Binding in Cleavage by the Nuclear Introns-Encoded Homing Endonuclease I-Ppol*, 394 Nature 96 (1998) and Chevalier, B. et al., *Design, Activity, and Structure of a Highly Specific Artificial Endonuclease*, 10 Molecular Cell 895 (2002).

Zinc finger nucleases (ZFNs) are synthetic proteins consisting of an engineered zinc finger DNA-binding domain fused to the cleavage domain of the FokI restriction endonuclease. ZFNs can be used to induce DSBs in specific DNA sequences and thereby promote site-specific homologous recombination and targeted manipulation of genomic loci in a variety of different cell types. The introduction of a DSB into dsDNA may enhance the efficiency of recombination with an exogenously introduced HDR template. ZFNs consist of a DNA-binding zinc finger domain (composed of three to six fingers) covalently linked to the non-specific DNA cleavage domain of the bacterial FokI restriction endonuclease. ZFNs can bind as dimers to their target DNA sites, with each monomer using its zinc finger domain to recognize a half-site. Dimerization of ZFNs is mediated by the FokI cleavage domain which cleaves within a five or six nucleotide "spacer" sequence that separates the two inverted "half sites." Because the DNA-binding specificities of zinc finger domains can in principle be re-engineered using one of various methods, customized ZFNs can be constructed to target nearly any DNA sequence. One of ordinary skill in the art will know how to design and use ZFNs to create DSBs in dsDNA at a desired target site. Some suitable protocols are available in Philipsborn, A. et al., *Microcontact printing of axon guidance molecules for generation of graded patterns,* 1 Nature Protocols 1322 (2006); John Young and Richard Harland, *Targeted Gene Disruption with Engineered Zinc Finger Nucleases (ZFNs),* 917 Xenopus Protocols 129 (2012), and Hansen, K. et al. *Genome Editing with CompoZr Custom Zinc Finger Nucleases (ZFNs),* 64 J. Vis. Exp. 3304 (2012).

TALENs are restriction enzymes that can be engineered to cut specific sequences of DNA. They are made by fusing a TAL effector DNA-binding domain to a DNA cleavage domain (i.e., a nuclease which cuts DNA strands). Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ. The DNA binding domain contains a repeated highly conserved 33-34 amino acid sequence with divergent $12^{th}$ and $13^{th}$ amino acids. These two positions, referred to as the Repeat Variable Diresidue (RVD), are highly variable and show a strong correlation with specific nucleotide recognition. This straightforward relationship between amino acid sequence and DNA recognition has allowed for the engineering of specific DNA-binding domains by selecting a combination of repeat segments containing the appropriate RVDs. Notably, slight changes in the RVD and the incorporation of "nonconventional" RVD sequences can improve targeting specificity. One of ordinary skill in the art will know how to design and use TALENs to create DSBs in dsDNA at a desired target site. Some suitable protocols are available in Hermann, M. et al., *Mouse Genome Engineering Using Designer Nucleases,* 86 J. Vis. Exp. 50930 (2014) and Sakuma, T. et al., *Efficient TALEN Construction and Evaluation Methods for Human Cell and Animal Applications,* 18(4) Genes Cells 315 (2013).

In the CRISPR/Cas nuclease system, the CRISPR locus, encodes RNA components of the system, and the Cas (CRISPR-associated) locus, encodes proteins. CRISPR loci in microbial hosts contain a combination of CRISPR-associated (Cas) genes as well as non-coding RNA elements capable of programming the specificity of the CRISPR-mediated polynucleotide cleavage.

The Type II CRISPR is one of the most well characterized systems and carries out targeted double-stranded breaks in four sequential steps. First, two non-coding RNAs, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. In engineered CRISPR/Cas9 systems, gRNA also called single-guide RNA ("sgRNA") may replace crRNA and tracrRNA with a single RNA construct that includes the protospacer element and a linker loop sequence. Standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). In the context of this disclosure, a guanine (G) is considered complementary to a uracil (U), and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary. Use of gRNA may simplify the components needed to use CRISPR/Cas9 for genome editing. The Cas9 species of different organisms have different PAM sequences. For example, *Streptococcus pyogenes* (Sp) has a PAM sequence of 5'-NGG-3', *Staphylococcus aureus* (Sa) has a PAM sequence of 5'-NGRRT-3' or 5'-NGRRN-3', *Neisseria meningitidis* (NM) has a PAM sequence of 5'-NNNNGATT-3', *Streptococcus thermophilus* (St) has a PAM sequence of 5'-NNAGAAW-3', *Treponema denticola* (Td) has a PAM sequence of 5'-NAAAAC-3'.

Finally, Cas9 mediates cleavage of target DNA to create a DSB within the protospacer. Activity of the CRISPR/Cas system in nature comprises three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien polynucleotide. The alien polynucleotides come from viruses attaching the bacterial cell. Thus, in the bacterial cell, several of the so-called 'Cas' proteins are involved with the natural function of the CRISPR/Cas system and serve roles in functions such as insertion of the alien DNA, etc.

CRISPR may also function with nucleases other than Cas9. Two genes from the Cpf1 family contain a RuvC-like endonuclease domain, but they lack Cas9's second HNH endonuclease domain. Cpf1 cleaves DNA in a staggered pattern and requires only one RNA rather than the two (tracrRNA and crRNA) needed by Cas9 for cleavage. Cpf1's preferred PAM is 5'-TTN, differing from that of Cas9 (3'-NGG) in both genomic location and GC-content. Mature crRNAs for Cpf1-mediated cleavage are 42-44 nucleotides in length, about the same size as Cas9's, but with the direct repeat preceding the spacer rather than following it. The Cpf1 crRNA is also much simpler in structure than Cas9's; only a short stem-loop structure in the direct repeat region is necessary for cleavage of a target. Cpf1 also does not require an additional tracrRNA. Whereas Cas9 generates blunt ends 3 nt upstream of the PAM site, Cpf1 cleaves in a staggered fashion, creating a five nucleotide 5' overhang 18-23 nt away from the PAM.

Other CRISPR-associated proteins besides Cas9 may be used instead of Cas9. For example, CRISPR-associated protein 1 (Cas1) is one of the two universally conserved proteins found in the CRISPR prokaryotic immune defense system. Cas1 is a metal-dependent DNA-specific endonuclease that produces double-stranded DNA fragments. Cas1 forms a stable complex with the other universally conserved CRISPR-associated protein, Cas2, which is part of spacer acquisition for CRISPR systems.

There are also CRISPR/Cas9 variants that do not use a PAM sequence such as NgAgo. NgAgo functions with a 24-nucleotide ssDNA guide and is believed to cut 8-11 nucleotides from the start of this sequence. The ssDNA is loaded as the protein folds and cannot be swapped to a different guide unless the temperature is increased to non-physiological 55° C. A few nucleotides in the target DNA are removed near the cut site. Techniques for using NgAgo are described in Gao, F. et al., *DNA-guided Genome Editing Using the Natronobacterium Gregoryi Argonaute*, 34 Nature Biotechnology 768 (2016).

DSBs may be formed by making two single-stranded breaks at different locations creating a cut DNA molecule with sticky ends. Single-strand breaks or "nicks" may be formed by modified versions of the Cas9 enzyme containing only one active catalytic domain (called "Cas9 nickase"). Cas9 nickases still bind DNA based on gRNA specificity, but nickases are only capable of cutting one of the DNA strands. Two nickases targeting opposite strands are required to generate a DSB within the target DNA (often referred to as a "double nick" or "dual nickase" CRISPR system). This requirement dramatically increases target specificity, since it is unlikely that two off-target nicks will be generated within close enough proximity to cause a DSB. Techniques for using a dual nickase CRISPR system to create a DSB are described in Ran, et al., *Double Nicking by RNA-Guided CRISPR Cas9 for Enhanced Genome Editing Specificity*, 154 Cell 6:1380 (2013).

In certain embodiments, any of the enzymes described in this disclosure may be a "functional derivative" of a naturally occurring protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of an enzyme or a fragment thereof include but are not limited to mutants, fusions, covalent modifications of the protein or a fragment thereof. The enzyme, or a fragment thereof, as well as derivatives or a fragment thereof, may be obtainable from a cell or synthesized chemically or by a combination of these two procedures. The cell may be a cell that naturally produces the enzyme. A cell that naturally produces enzyme may also be genetically engineered to produce the endogenous enzyme at a higher expression level or to produce the enzyme from an exogenously introduced polynucleotide, which polynucleotide encodes an enzyme that is the same or different from the endogenous enzyme. In some cases, a cell does not naturally produce the enzyme and is genetically engineered to produce the enzyme. The engineering may include adding the polynucleotide encoding the enzyme under the control of a promoter. The promoter may be an inducible promoter that is activated in response to a signal. The promoter may also be blocked by a different signal or molecule.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document, "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause A. A method comprising: producing a first homology directed repair (HDR) template including at least a first splicing region and a barcode region, the first splicing region including a first sequence of nucleotides that is recognized by an enzyme to produce a cut in the first splicing region and the barcode region including a sequence of nucleotides that corresponds to a gene; inserting the first HDR template into a target site of the gene using HDR; splice, using the enzyme, the first HDR template in at least the first splicing region to produce a second HDR template, the second HDR template including a sequence of nucleotides that includes a portion of the first splicing region and the barcode region; inserting the second HDR template into a double stranded polynucleotide using HDR; sequencing the additional double stranded polynucleotide to produce sequencing data; and determining that the gene has been expressed based at least partly on identifying the sequence of nucleotides of the barcode region in the sequencing data.

Clause B. The method of claim A, wherein: the first HDR template includes a second splicing region; the first splicing region is homologous to a first portion of a target site of the gene; and the second splicing region is homologous to a second portion of the target site of the gene.

Clause C. The method of clause A or B, wherein the first HDR template is inserted in the 3' untranslated region of the gene.

Clause D. The method of any one of clauses A-C, wherein the double stranded polynucleotide is at least one of genomic DNA, artificial DNA, circular DNA, or linear DNA.

Clause E. The method of any one of clauses A-D, wherein the enzyme is a spliceosome, and the method further comprises designing the first HDR template such that the first splicing region includes the sequence of nucleotides recognized by the spliceosome and the second HDR template remains viable to perform HDR with the double stranded polynucleotide for a specified period of time.

Clause F. The method of any one of clauses A-E, further comprising: before inserting the first HDR template into the target site, inserting a third HDR template into the gene using HDR, wherein the third HDR template includes the target site.

Clause G. The method of any one of clauses A-F, further comprising: generating data indicating a plurality of barcode sequences, wherein the gene is one of a plurality of genes; and associating individual genes of the plurality of genes with a respective barcode sequence of the plurality of barcode sequences such that each barcode sequence of the plurality of barcode sequences corresponds to a particular gene.

Clause H. The method of any one of clauses A-G, further comprising producing a gene product as a result of the expression of the gene, wherein: the gene product includes a single stranded polynucleotide sequence that includes a first section corresponding to the first splicing region and a second section corresponding to the barcode region.

Clause I. A system comprising: a gene including a double stranded polynucleotide having a target site; an enzyme configured to create a double strand break in the double stranded polynucleotide of the gene at a cut site in the target site; and a HDR template including at least a first splicing region and a barcode sequence corresponding to the gene; wherein the HDR template is inserted into the target site with homology directed repair (HDR) at the cut site after the enzyme creates a break at the cut site.

Clause J. The system of clause I, wherein the system comprises a single eukaryotic cell or a single prokaryotic cell.

Clause K. The system of clause I or J, further comprising an additional double stranded polynucleotide including an additional target site.

Clause L. The system of clause K, wherein: at least a portion of the first HDR template is removed from the double stranded polynucleotide of the gene using at least one spliceosome to produce a second HDR template that includes at least the barcode sequence and a portion of the first splicing region.

Clause M. The system of any one of clauses I-L, wherein expression of the gene produces an RNA precursor that includes a single stranded polynucleotide including: a first sequence that corresponds to the first splicing region; a second sequence that corresponds to the barcode sequence; a 3' untranslated region (UTR) and a 5' UTR; and a coding region that includes an intron and a exon.

Clause N. The system of clause M, wherein the intron included in the RNA precursor includes the HDR template.

Clause O. The system of clause M, wherein the 3' UTR includes the first sequence and the second sequence.

Clause P. A system comprising: a gene; a double stranded polynucleotide including a target site; a homology directed repair (HDR) template including a barcode region having a sequence of nucleotides that corresponds to the gene; and an enzyme configured to create a double strand break in the double stranded polynucleotide at the target site; wherein the HDR template is inserted into the double stranded polynucleotide by HDR to produce a modified double stranded polynucleotide.

Clause Q. The system of clause P, wherein: the modified double stranded polynucleotide includes an additional target site; the system further comprises an additional HDR template; and the additional HDR template is inserted into the additional target site via HDR.

Clause R. The system of clause Q, wherein: the system further comprising a first gene encoding the HDR template and a second gene encoding the additional HDR template; expression of the first gene causes the HDR template to become available for insertion into the target site; and expression of the second gene causes the additional HDR template to become available for insertion into the additional target site.

Clause S. The system of clause R, wherein: the second gene is expressed in response to a signal that occurs at a particular time; and analysis of a sequence of the modified double stranded polynucleotide indicates a period of time that the first gene was expressed based at least partly on the presence of the additional HDR template in the sequence of the modified double stranded polynucleotide.

Clause T. The system of any one of clauses P-S, further comprising: an additional gene that includes an additional HDR template having a sequence that includes the sequence of nucleotides of the barcode region and at least one splicing region; and an additional enzyme to remove at least a portion of the additional HDR template to create the HDR template and make the HDR template available for insertion into the double stranded polynucleotide Clause U. A method comprising: producing a first homology directed repair (HDR) template including a region complementary to a first portion of an RNA strand, wherein the RNA strand is produced from expression of a gene; producing a second HDR template including a region complementary to a second portion of the RNA strand; annealing the first HDR template to the first portion of the RNA strand and the second HDR template to the second portion of the RND strand to produce a modified RNA strand; joining a 5' end of the first HDR template and a 3' end of the second HDR template to produce a third HDR template; inserting the third HDR template into a target site of a polynucleotide using HDR to produce a modified polynucleotide; and determining that the gene has been expressed based at least partly ono sequencing data of the modified polynucleotide.

Clause V. The method of clause U, wherein the RNA strand is messenger RNA (mRNA) produced during the expression of the gene.

Clause W. The method of Clause U or V, wherein the third HDR template is annealed to the RNA strand as the portion of the third HDR template is being inserted into the target site.

Clause X. The method of Clause U or V, wherein the third HDR template is separated from the RNA strand as the portion of the third HDR template is being inserted into the target site.

Clause Y. A system comprising: a gene; a first homology directed repair (HDR) template including a first portion of a barcode sequence; and a second HDR template including a second portion of a barcode sequence; wherein the gene produces an RNA strand during the expression of the gene and a first region of the first HDR template anneals to a complementary first region of the RNA strand and a second region of the second HDR template anneals to a complementary second region of the RNA strand.

Clause Z. The system of clause Y, wherein a hybridized product of the first HDR template, the second HDR template, and the RNA strand forms a template for a third HDR template.

Clause AA. The system of clause Y or Z, wherein the first region of the RNA strand is adjacent to the second region of the RNA strand.

Clause BB. The system of any one of clauses Y-AA, wherein a 5' end of the first HDR template is joined to a 3' end of the second HDR template.

Clause CC. The system of any one of clauses Y-BB, further comprising a polynucleotide include a target region.

Clause DD. The system of clause CC, wherein the first HDR template includes a first sequence separate from the first region that is complementary to a first portion of the target region and the second HDR template includes a second sequence separate from the second region that is complementary to a second portion of the target region.

Clause EE. The system of clause DD, further comprising an enzyme to create a double strand break (DSB) at a cut site of the target region of the polynucleotide; and wherein the barcode sequence is inserted into the polynucleotide at the cut site to produce a modified polynucleotide using HDR.

Conclusion

The terms "a," "an," "the" and similar referents used in the context of describing the invention (especially in the context of the following claims) are to be construed to cover both the singular and the plural, unless otherwise indicated herein or clearly contradicted by context. The term "based on" is to be construed to cover both exclusive and nonexclusive relationships. For example, "A is based on B" means that A is based at least in part on B and may be based wholly on B. By "about" is meant a quantity, level, value, number, frequency, percentage, dimension, size, amount, weight or length that varies by as much as 10, 9, 8, 7, 6, 5, 4, 3, 2 or 1% to a reference quantity, level, value, number, frequency, percentage, dimension, size, amount, weight or length.

All methods described herein can be performed in any suitable order unless otherwise indicated herein or otherwise clearly contradicted by context. The use of all examples and exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

Furthermore, references have been made to publications, patents and/or patent applications (collectively "references") throughout this specification. Each of the cited references is individually incorporated herein by reference for their particular cited teachings as well as for all that they disclose.

The invention claimed is:

1. A system that creates a record of gene expression, the system comprising:
- a double stranded polynucleotide comprising a target site and a gene encoding a first homology directed repair (HDR) template, wherein the target site is not located in the gene;
- an enzyme configured to create a double strand break in the double stranded polynucleotide at a cut site in the target site; and
- the first HDR template including a first sequence complementary to a first subsequence of the target site, a second sequence complementary to a second subsequence of the target site, and a barcode sequence that uniquely identifies the gene;
- wherein the first HDR template is configured to add the barcode sequence into the target site with HDR at the cut site after the enzyme creates a break at the cut site and wherein a sequence of the gene when expressed encodes an RNA precursor that includes a single stranded polynucleotide including:
  - a first sequence that corresponds to a first splicing region;
  - a second sequence that corresponds to the barcode sequence;
  - a 3' untranslated region (UTR) and a 5' UTR; and
  - a coding region that includes an intron and an exon.

2. The system of claim 1, wherein the system comprises a single eukaryotic cell or a single prokaryotic cell.

3. The system of claim 1, further comprising an additional double stranded polynucleotide including an additional target site.

4. The system of claim 3, wherein the first HDR template includes a first splicing region, wherein the additional target site is complementary to at least a portion of a second HDR template that includes at least the barcode sequence and a portion of the first splicing region, the second HDR template generated by at least one spliceosome removing at least a portion of the first HDR template from the gene.

5. The system of claim 1, wherein the intron included in the RNA precursor includes the HDR template.

6. The system of claim 1, wherein the 3' UTR includes the first sequence and the second sequence.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: X1 example

<400> SEQUENCE: 1
tagccgtatc gagcatcgat g                                             21

<210> SEQ ID NO 2
<211> LENGTH: 11
<212> TYPE: DNA
<213> ORGANISM: Artificial Sequence
<220> FEATURE:
<223> OTHER INFORMATION: X2 example
<220> FEATURE:
<221> NAME/KEY: misc_feature
<222> LOCATION: (4)..(7)
<223> OTHER INFORMATION: n is a, c, g, or t

<400> SEQUENCE: 2
cgcnnnngat t                                                        11

<210> SEQ ID NO 3
<211> LENGTH: 21
<212> TYPE: DNA
<213> ORGANISM: Artificial Sequence
<220> FEATURE:
<223> OTHER INFORMATION: Y1 example

<400> SEQUENCE: 3
gatcgatgga ctctgcatct a                                             21

<210> SEQ ID NO 4
<211> LENGTH: 11
<212> TYPE: DNA
<213> ORGANISM: Artificial Sequence
```

```
<220> FEATURE:
<223> OTHER INFORMATION: Y2 example
<220> FEATURE:
<221> NAME/KEY: misc_feature
<222> LOCATION: (4)..(7)
<223> OTHER INFORMATION: n is a, c, g, or t

<400> SEQUENCE: 4
tcgnnnngat t                                                              11

<210> SEQ ID NO 5
<211> LENGTH: 21
<212> TYPE: DNA
<213> ORGANISM: Artificial Sequence
<220> FEATURE:
<223> OTHER INFORMATION: Z1 example

<400> SEQUENCE: 5
cgggacgatc gatcgggcta g                                                   21

<210> SEQ ID NO 6
<211> LENGTH: 11
<212> TYPE: DNA
<213> ORGANISM: Artificial Sequence
<220> FEATURE:
<223> OTHER INFORMATION: Z2 example
<220> FEATURE:
<221> NAME/KEY: misc_feature
<222> LOCATION: (4)..(7)
<223> OTHER INFORMATION: n is a, c, g, or t

<400> SEQUENCE: 6
actnnnngat t                                                              11

<210> SEQ ID NO 7
<211> LENGTH: 64
<212> TYPE: DNA
<213> ORGANISM: Artificial Sequence
<220> FEATURE:
<223> OTHER INFORMATION: Homology directed repair sequences of X1Y1Y2X2
<220> FEATURE:
<221> NAME/KEY: misc_feature
<222> LOCATION: (46)..(49)
<223> OTHER INFORMATION: n is a, c, g, or t
<220> FEATURE:
<221> NAME/KEY: misc_feature
<222> LOCATION: (57)..(60)
<223> OTHER INFORMATION: n is a, c, g, or t

<400> SEQUENCE: 7
tagccgtatc gagcatcgat ggatcgatgg actctgcatc tatcgnnnng attcgcnnnn         60
gatt                                                                      64

<210> SEQ ID NO 8
<211> LENGTH: 64
<212> TYPE: DNA
<213> ORGANISM: Artificial Sequence
<220> FEATURE:
<223> OTHER INFORMATION: Homology directed repair sequences Y1X1X2Y2
<220> FEATURE:
<221> NAME/KEY: misc_feature
<222> LOCATION: (46)..(49)
<223> OTHER INFORMATION: n is a, c, g, or t
<220> FEATURE:
<221> NAME/KEY: misc_feature
<222> LOCATION: (57)..(60)
<223> OTHER INFORMATION: n is a, c, g, or t
```

-continued

```
<400> SEQUENCE: 8
gatcgatgga ctctgcatct atagccgtat cgagcatcga tgcgcnnnng atttcgnnnn    60
gatt                                                                 64
```